United States Patent
Dicks et al.

(10) Patent No.: US 7,951,385 B2
(45) Date of Patent: May 31, 2011

(54) PROBIOTIC STRAIN AND ANTIMICROBIAL PEPTIDE DERIVED THEREFROM

(75) Inventors: Leon Milner Theodore Dicks, Matieland (ZA); Svetoslav Dimitrov Todorov, Belogratchik (BG); Hendriette Knoetze, Matieland (ZA); Marelize Brink, Matieland (ZA)

(73) Assignee: Cipla Medpro Research and Development (Pty) Ltd., Bellville (ZA)

( * ) Notice: Subject to any disclaimer, the term of this patent is extended or adjusted under 35 U.S.C. 154(b) by 0 days.

(21) Appl. No.: 12/302,067

(22) PCT Filed: May 25, 2007

(86) PCT No.: PCT/IB2007/051982
§ 371 (c)(1),
(2), (4) Date: Aug. 10, 2009

(87) PCT Pub. No.: WO2007/138538
PCT Pub. Date: Dec. 6, 2007

(65) Prior Publication Data
US 2009/0297482 A1     Dec. 3, 2009

(30) Foreign Application Priority Data
May 28, 2006  (ZA) .................................. 2006/04035

(51) Int. Cl.
*A61K 39/02*     (2006.01)
(52) U.S. Cl. ..................... 424/234.1; 424/93.1; 435/243; 435/252.1
(58) Field of Classification Search .......................... None
See application file for complete search history.

(56) References Cited

U.S. PATENT DOCUMENTS

| 6,878,373 B2 | 4/2005 | Keeton et al. |
| 6,919,080 B2 | 7/2005 | Tokunaga et al. |
| 6,919,427 B1 | 7/2005 | Mao et al. |
| 6,929,793 B2 | 8/2005 | Spivey-Krobath et al. |
| 6,960,341 B2 | 11/2005 | Viscomi et al. |

FOREIGN PATENT DOCUMENTS

| JP | 2003 339377 | 12/2003 |
| WO | WO 03/035681 | 5/2003 |

OTHER PUBLICATIONS

Kawato Shinichi et al:"Biochemical and genetic characterization of mundticin KS, an antilisterial peptide produced by *Enterococcus mundtii* NFRI 7393", Aug. 2002, vol. 68 No. 8, pp. 3830-3840, Applied and Environmental Microbiology.
Saavedra Lucila et al: "Enhancement of the enterocin CRL35 activity by a synthetic peptide derived from the NH2-terminal sequence" Jul. 2004, vol. 48, No. 7, pp. 2778-2781, Antimicrobial Agents and Chemotherapy.
Todorov S D et al: "An antibacterial and antiviral peptide produced by *Enterococcus mundtii* ST4V isolated from soya beans" Jun. 2005, vol. 25, No. 6 pp. 508-513, International Journal of Antimicrobial Agents, Amsterdam, NL.
Zendo T et al: "Identification and production of a bacteriocin from *Enterococcus mundtii* QU 2 isolated from soybean" 2005, vol. 99, No. 5, pp. 1181-1190, Journal of Applied Microbiology.
De Kwaadsteniet et al: "Characterization of a 3944 Da bacteriocin, produced by *Enterococcus mundtii* ST15, with activity against Gram-positive and Gram-negative bacteria" Dec. 15, 2005, vol. 105, No. 3, International Journal of Food Microbiology, Elsevier Science Publishers, Amsterdam, NL.
Van Reenen, et al. "Isolation, purification and partial characterization of plantaricin 423, a bacteriocin produced by *Lactobacillus plantarum*." 1998, pp. 1131-1137, 84, *J. Appl. Microbiol.*
Verellen, et al "Fermentation optimization of plantaricin 423, a bacteriocin produced by *Lactobacillus plantarum* 423" 1998, pp. 174-179, 86, *J. Ferment. Bioeng.*
Nel, et al, "Effect of bacteriocins pediocin PD-1, plantaricin 423, and Nisin on biofilms of *Oenococcus oeni* on a stainless steel surface." 2002, pp. 191-196, 53, *Am. J. Enol. Viticult.*
Van Reenen, et al,. "Characterization and heterologous expression of a class IIa bacteriocin, plantaricin 423 from *Lactobacillus plantarum* 423, in *Saccharomyces cerevisiae*." 2002, 29-40, 81, *Int. J. Food Microbiol.*
Brink, M., S.D. Todorov, M. Senekal and L.M.T. Dicks. 2006. The effect of prebiotics on the production of antimicrobial compounds, resistance to growth at low pH and in the presence of bile, and adhesion of probiotic cells to intestinal mucus. *J. Appl. Microbiol.* 100: 813-820.
Mare, L., G.M. Wolfaardt, L.M.T. Dicks. 2006. Adhesion of *Lactobacillus plantarum* 423 and *Lactobacillus salivarius* 241 to the intestinal tract of piglets, as recorded with fluorescent in situ hybridization (FISH), and production of plantaricin 423 by cells colonized to the ileum. *J. Appl. Microbiol.* 100: 838-845.
Powell, J., Todorov, S.D., Van Reenen, C.A., Dicks, L.M.T., Witthuhn, C. 2006. Growth inhibition of *Enterococcus mundtii* in kefir by in situ production of bacteriocin ST8KF. *Lait.* 86: 401-405.
Van Reenen, C.A., Van Zyl, W.H., Dicks L.M.T. 2006. Expression of the immunity protein of plantaricin 423, produced by *Lactobacillus plantarum* 423, and analysis of the plasmid encoding the bacteriocin. *Applied and Environmental Microbiology.* 72: 7644-7651.
Van Reenen, C.A. and Dicks, L.M.T 1996 Evaluation of numerical analysis of random amplified polymorphic DNA (RAPD)-PCT as a method to differentiate *Lactobacillus plantarum* and *lactobacillus pentosus. Curr Mictrobiol.* 32:183-187.

(Continued)

Primary Examiner — Jennifer E Graser
(74) Attorney, Agent, or Firm — Stites & Harbison PLLC; B. Aaron Schulman; Stephen J. Weyer

(57) ABSTRACT

The invention relates to a strain of *Enterococcus mundtii* having probiotic qualities. The strain of *E. mundtii* (ST4SA) produces an antimicrobial peptide which exhibits antimicrobial activity against a broad range of bacteria. The invention also provides an isolated nucleotide sequence which codes for the antimicrobial peptide (peptide ST4SA). Another aspect of the invention relates to a process for the production of a peptide of the invention which comprises cultivating *Enterococcus mundtii* strain ST4SA in a nutrient medium under micro-aerophilic conditions at a temperature of between 100 C. and 45° C., until a recoverable quantity of said peptide is produced, and recovering said peptide. The isolated peptide of the invention may be used as an antimicrobial agent in a liquid formulation or a gel formulation as a topical treatment and may also be used as an antimicrobial agent following encapsulation in a polymer.

3 Claims, 25 Drawing Sheets

OTHER PUBLICATIONS

Dicks, LMT., F.D. Mellett and L.C. Hoffman 2003 Use of bacteriocin-producing starter cultures of *Lactobacillus plantarum* and *Lactobacillus curvatus* in production of ostrich meat salami. *Meat Science* 66:703-708.

Bauer, et al "Control of malolactic fermentation in wine." 2004, pp. 74-88, 25, *S.A. J Enol. Vitic.*.

Bauer, et al,. "Mode of action of lipid II-targeting lantibiotics.", 2005, pp. 201-216, 101, *Int. J. Food Microbiol.*

M. Granger, S.D. Todorov, M.K.A. Mathews, L.M.T. Dicks. 2005. Growth of *Enterococcus mundtii* in medium filtrate and purification of bacteriocin ST15 by cation exchange chromatography. *Journal of Basic Microbiol.* 45: 419-425.

Brink, M., S.D. Todorov, M. Senekal and L.M.T. Dicks. 2006. The effect of prebiotics on the production of antimicrobial compounds, resistance to growth at low pH and in the presence of bile, and adhesion of probiotic cells to intestinal mucus. *J. Appl. Microbiol.* 100: 813-820.

Todorov, S.D and L.M.T. Dicks. 2006 Medium components effecting bacteriocin production by two strains of *Lactobacillus plantarum* ST414BZ and ST664BZ isolated from boza *Biologia* 61:3:269-274.

Powell, J., Witthuhn, C., Todorov, S.D., Dicks, L.M.T., 2006. Characterization of bacteriocin ST8KF produced by a kefir isolate *Lactobacillus plantarum* ST8KF. *Int Dairy Journal* 17: 190-198.

SEQUENCE LISTING OF E. MUNDTII POLYNUCLEOTIDES AND POLYPEPTIDES

SEQ. ID. NO. 11
**Polynucleotide encoding *Enterococcus mundtii* (ATCC PTA-7278) antimicrobial peptide ST4SA**

ATGTCACAAGTAGTAGGTGGAAAATACTACGGTAATGGAGTCTCATGTAATAAAAAAGGGTGCAGTGTTGATTGGGGAAAAGCTATTGGCATTATTG
GAAATAATTCCGCTGCCAATTTAGCTACTGGTGGAGCAGCTGGTTGGAAAAGTTAA

SEQ. ID. NO. 12
**Polypeptide encoded by *Enterococcus mundtii* (ATCC PTA-7278) antimicrobial peptide ST4SA**

MSQVVGGKYYGNGVSCNKKGCSVDWGKAIGIIGNNSAANLATGGAAGWKS

SEQ. ID. NO. 13
**Polynucleotide encoding *Enterococcus mundtii* ST4SA (ATCC PTA-7278) ABC transporter gene**

ATGCAGATGATTTTAAATAATTTTCATTCATGGATTTCAGTGGAAGTTTTAAGAGACTTAACTGAAACCGATTCTGAACGTACCTGTGCATTAGGTA
TAGTTAACGGATTTGCTAAATTAGGAATAAATTGTGAAGCCTATAAAGCTAATAGTGATGTATGGAAAGAAAATGAGTTCAATTATCCCGTAATTGC
TAATATAGTAACGAATAATCAATTTCTTCATTATTGTATTGTATATGCTGTGAAAAAAGAGAAATTGTTAATAGCTGACCCTGCGATTGGAAAATAC
AAAGAATCAATAGAAAAGTTCAACAACAAATGGACTGGTGTTATTTTAGTTGCTGAAAAGACTCCTGATTTCCAACCCATAAATAATACAAAAAAAA
GTTTTTTTTCTTCAATAAGTTTATTAAAAGATCAATATAAAAAAATTTTATTGGTGATATTATCTTCATTAATAATAACAATTATAGGAATACTATC
AAGTTACTATTTTAGAATTTTTAATAGATTGGTTACTTCCTGAAAAAGACTTTTTAAATCTATTTATGATATCAATTAGCTATATCATAGGCATCTTT
ATAACAAGTATATTTCAAATTACCAGAAGATATAATTTAGAAAAGCTAGGACAAGATGTAGGTAGAAGCATTTTATTTAAATATTTAGAACATATTT
TCATTTTACCAGCTTCCTTTTTTTCTAAAAGAAAAACTGGAGATATTGTCTCTAGATTTTCCGATGCTAATAAAATTATAGAAGCTTTAGCTAGCTT
TACTATATCTATTTTTTTACATTTAAGTTCAGTCATTGTTGTGGGGATTATATTGATCAATATTAATAAACAATTATTTTTAATAACGTTAAGTTCT
ATTCCATTTTATATACTAATTATATTAGGATCAAATAAAAAAATGAGTCGATTAAACGGAGAAGACATGCAAACAAATTCAATAGTTGATTCTAATT
CTATTGAAGGATTAAACGGAATATATACTATAAAAGCACTTTGTAGTGAGAATAAGATTGTAAATCAAATATATAGAAGTTTAAATAAATTTTTCGA
TGTATCACTAAAGAGAAATATGTATGATTCTATAATTCAAAATTTAAAAATTTTGGTTTCTCCTTTTAACCTCGGCTTTTCTATTATGGCTTGGTTCG
TATTATGTTATCAATGGAGAAATTACAATAGGAGAACTAATAACTTTCAATTCATTATCTATATTTTTTCTACACCTCTACAAAATATAATAAATC
TACAAGAAAAATTCCAAAAAGCACAAGTTGCAAATAATCGGCTTAACGATGTATTTTCTATAAATAATGAAAATAAAGACAAGTTTATTCATTTGGC
TAAATTAACTGAAAAAGCAACGATTACATTTCAAAATGTATATTTTAGTTATTCTACTAAATATCCTAATGTGTTAGATAATATGAGTTTTTCTCTA
CCTGTGAGTAAAAATATAGGAATAAAAGGTGATAGTGGTGCTGGGAAATCAACTTTAGCACAACTTCTAGCTGGATTTTACTCTCCAGATAATGGAA
GAATTGTATAAAGCAGCAAAATATTGAAAATATTAATAGAAAAGATTTACGTAAGTTGATTACCTATGTGCCTCAAGAATCTTTTATTATGAGTGG
AACTATTAAAGACAATTTATTTTTAGGTTTAGAAAGTATTCCTGATCAACAAGAACTCGAAAAAGTACTGAAAGATACTTGTTTATCCAGTTATATT
ACTGCGCCTCCTCTAGGACTTGATACGTATCTAGAAGAAATGGTGCGAATTTATCAGGTGGTCAAAAGCAAAGAATTGCTTTAGCAAGAGTTTTAT
TATTAGGAAGTAAAATTTTATTATTAGATGAAGCTACGAGTGCTCTAGATTCTAAAACTGAAATGCTGATTTTAGAAAAATTATTAAACTACCCTAA
TAAGTCAATCATTATGATATCTCATAATGATAAATTAATACACAAGTGTGACTTAATCATTGATTTAGACCAAAGCCATTCATAA

SEQ. ID. NO. 14
**Polypeptide encoded by *Enterococcus mundtii* ST4SA (ATCC PTA-7278) ABC transporter gene**

MQMILNNFHSWISVEVLRDLTETDSEGTCALGIVNGFAKLGINCEAYKANSDVWKENEFNYPVIANIVTNNQFLHYCIVYGVKKEKLLIADPAIGKY
KESIEKFNNKWTGVILVAEKTPDFQPINNTKKSFFSSISLLKDQYKKILLVILSSLITTIGILSSYYFRILIDWLLPEKDFLNLFMISISYIIGIF
ITSIFEITRRYNLEKLGQDVGRSILFKYLEHIFILPASFFSKRKTGDTVSRFSDANKIIEALASFTISIFLDLSSVIVVGIIITNINKQLFLITLSS
IPFYILIILGSNKKMSRLNGEEMQTNSIVDSNFIEGLNGIYIIKALCSENKIVNQIYRSLNKFFDVSLKRNMYDSIIONLKILVSLLTSAFVLWLGS
YYVINGEITIGELTTFNSLSIFFSTPLQKIINLQEKFQKAQVANNRLNDVFSIKNENKDKFIHLAKLTEKATITFENVYFSYSTKYPNVLDNMSFSL
PVSKNIGIKGDSGAGKSTLAQLLAGFYSPDNGRICTNFQNIENINRKDLRKLITYVPQESFIMSGTIKDNLFTGLRSIPDEQELEKVLKDTCLWSYI
TAPPLGLDTYLEENGANLSGGQKQRIALARVLLLGSKILLLDEATSALDSKTEMLILEKLLKYPNKSIIMISHNDKLIDKCDLIIDLDERDS

SEQ. ID. NO. 15
**Polynucleotide encoding *Enterococcus mundtii* ST4SA (ATCC PTA-7278) immunity gene**

ATGAGTAATTTAAAGTGGTTTTCTGGTGGAGACGATCGACGTAAAAAAGCAGAAGTGATTATTACTGAATTATTAGATGATTTAGAGATAGATCTTG
GAAATGAATCTCTTCGAAAAGTATTAGGCTCCTATCTTGAAAAGTTGAAAAATGAACGAACTTCAGTTCCATTAGTTTTAAGTCGTATGAATATAGA
GATATCTAATGCAATAAAAAAAGACGGTGTATCGTTAAATGAAAATCAATCTAAAAAATTAAAAGAACTCATATCTATATCTAATATTAGATATGGA
TATTAG

SEQ. ID. NO. 16
**Polypeptide encoded by *Enterococcus mundtii* ST4SA immunity gene**

MSNLKWFSGGDDRRKKAEVIITELLDDLEIDLGNESLRKVLGSYLEKLKNECTSVPLVLSRMNIEISNAIKDGVSLNENQSKELKELISISNIRYG
Y

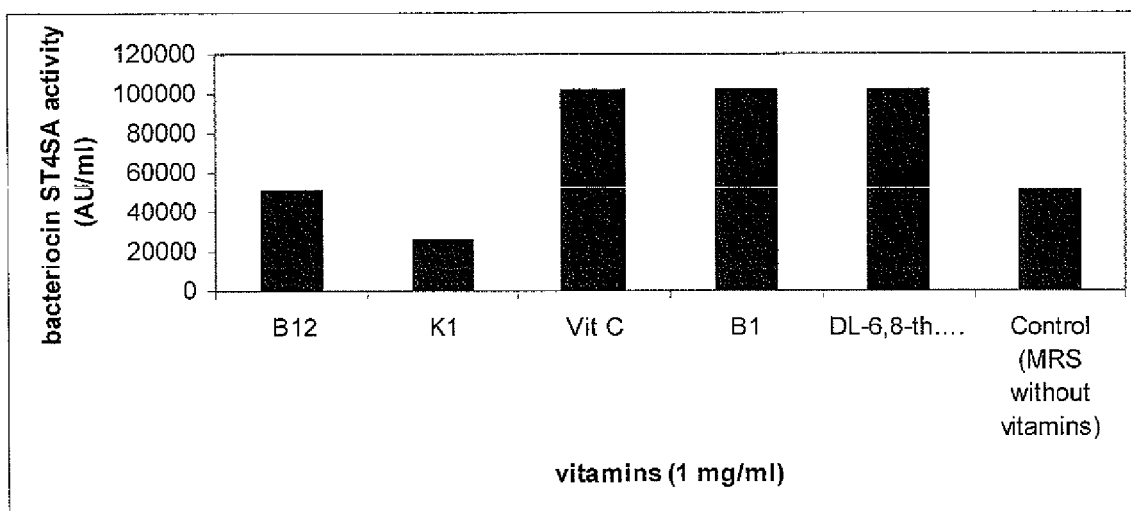
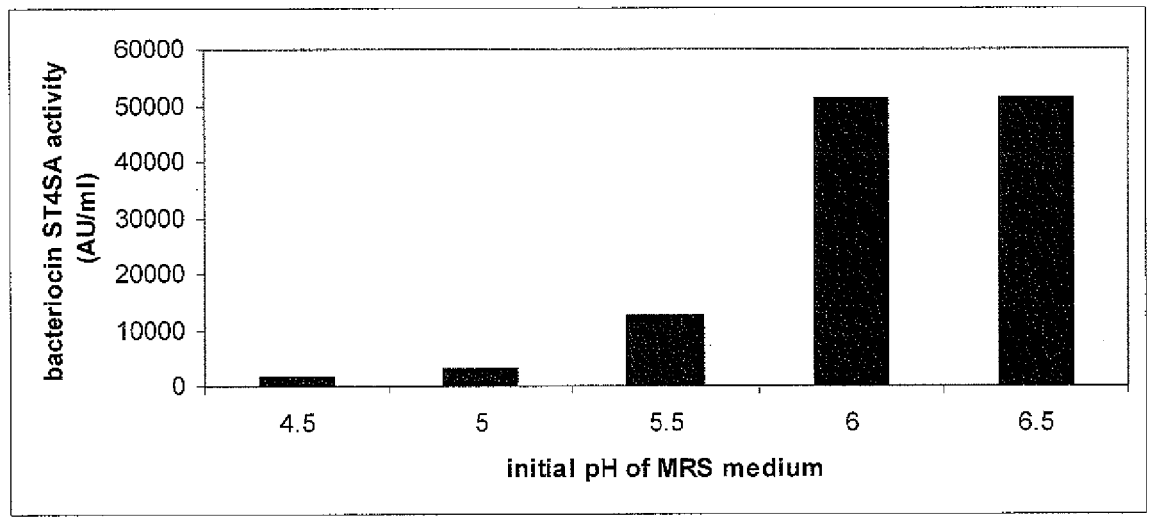
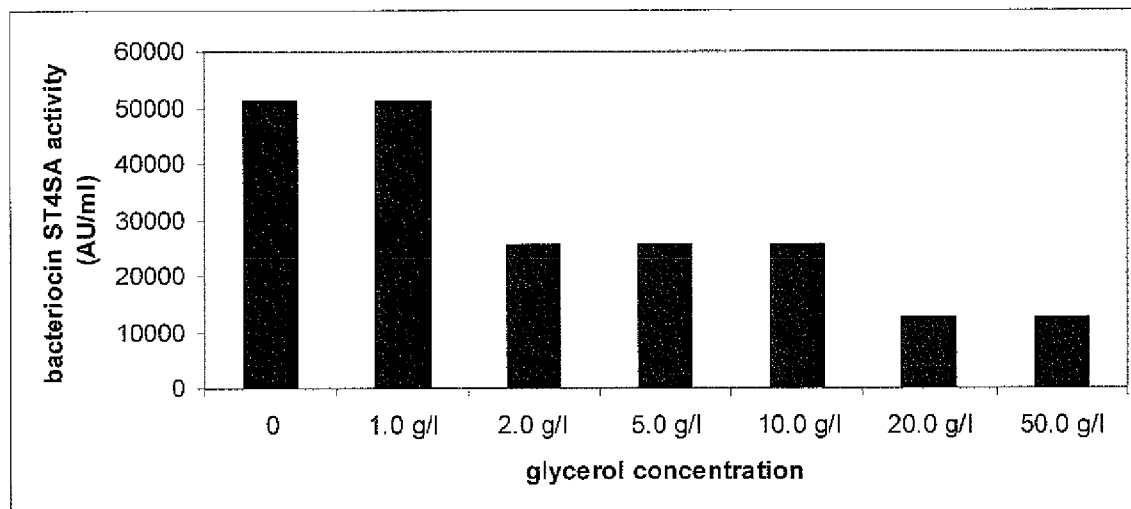
Fig. 9A. Influence of growth medium components on peptide ST4 production

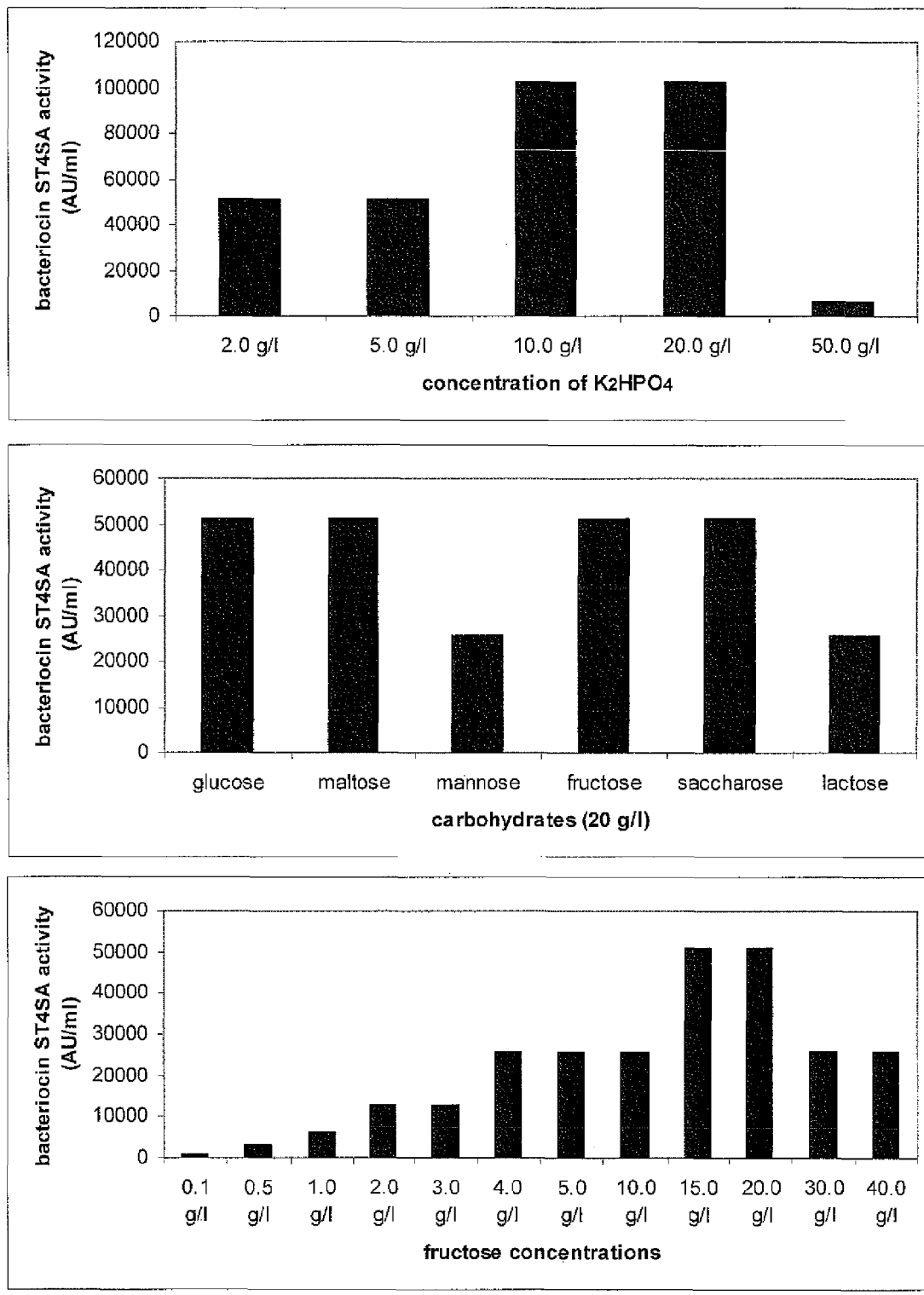
Fig. 9B. Influence of growth medium components on peptide ST4 production

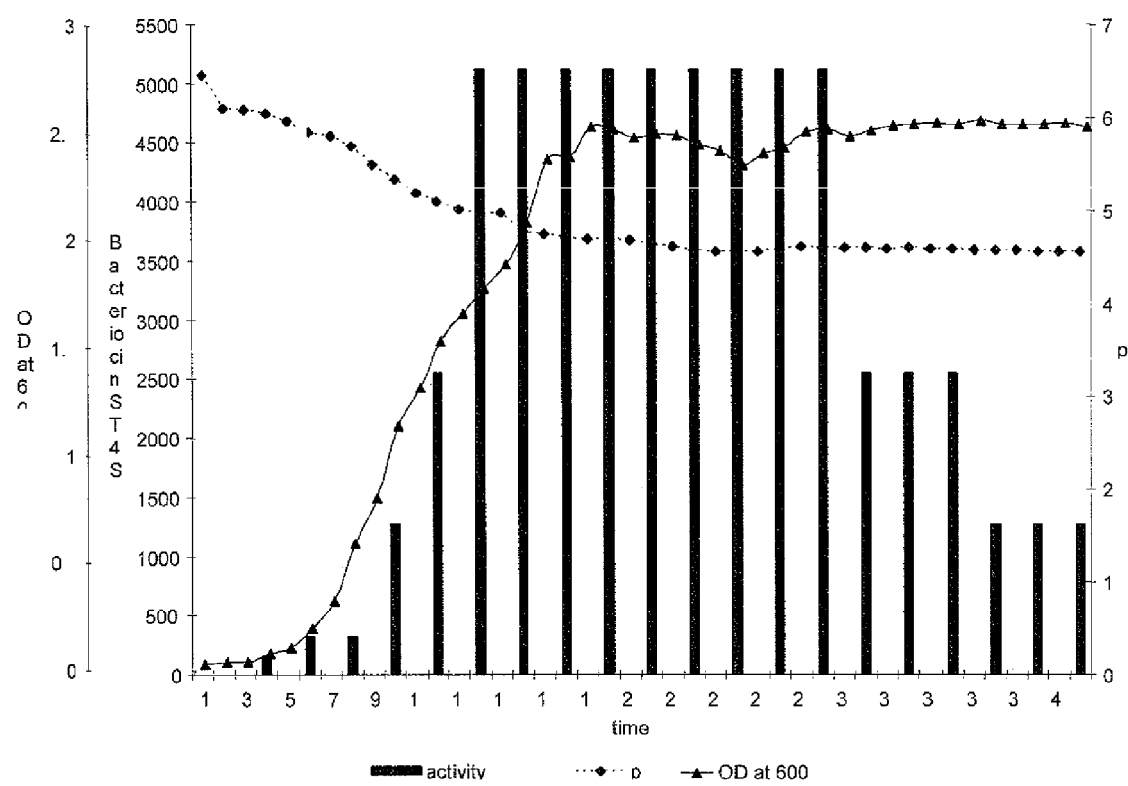
Fig. 10. Production of peptide ST4SA in MRS broth.

SEQUENCE LISTING

<160> NUMBER OF SEQ ID NOS: 20

<210> SEQ ID NO 1
<211> LENGTH: 14
<212> TYPE: DNA
<213> ORGANISM: ENTEROCOCCUS MUNDTII ST4SA

<400> SEQUENCE: 1

```
aacgagcgca accc                                                    14

<210> SEQ ID NO 2
<211> LENGTH: 16
<212> TYPE: DNA
<213> ORGANISM: ENTEROCOCCUS MUNDTII ST4SA

<400> SEQUENCE: 2
gacgggcggt gtgtac                                                  16

<210> SEQ ID NO 3
<211> LENGTH: 26
<212> TYPE: DNA
<213> ORGANISM: ENTEROCOCCUS MUNDTII ST4SA

<400> SEQUENCE: 3
tgagagaagg tttaagtttt gaagaa                                       26

<210> SEQ ID NO 4
<211> LENGTH: 21
<212> TYPE: DNA
<213> ORGANISM: ENTEROCOCCUS MUNDTII ST4SA

<400> SEQUENCE: 4
tccactgaaa tccatgaatg a                                            21

<210> SEQ ID NO 5
<211> LENGTH: 20
<212> TYPE: DNA
<213> ORGANISM: ENTEROCOCCUS MUNDTII ST4SA

<400> SEQUENCE: 5
tgatggattt cagtggaagt                                              20

<210> SEQ ID NO 6
<211> LENGTH: 20
<212> TYPE: DNA
<213> ORGANISM: ENTEROCOCCUS MUNDTII ST4SA

<400> SEQUENCE: 6
atctcttctc cgtttaatcg                                              20

<210> SEQ ID NO 7
<211> LENGTH: 20
<212> TYPE: DNA
<213> ORGANISM: ENTEROCOCCUS MUNDTII ST4SA

<400> SEQUENCE: 7
gtcattgttg tggggattat                                              20

<210> SEQ ID NO 8
<211> LENGTH: 20
<212> TYPE: DNA
<213> ORGANISM: ENTEROCOCCUS MUNDTII ST4SA

<400> SEQUENCE: 8
tctagatacg tatcaagtcc                                              20

<210> SEQ ID NO 9
<211> LENGTH: 20
<212> TYPE: DNA
<213> ORGANISM: ENTEROCOCCUS MUNDTII ST4SA

<400> SEQUENCE: 9
```

```
ttcctgatga acaagaactc                                              20

<210> SEQ ID NO 10
<211> LENGTH: 20
<212> TYPE: DNA
<213> ORGANISM: ENTEROCOCCUS MUNDTII ST4SA

<400> SEQUENCE: 10
gtccccacaa ccaataacta                                              20

<210> SEQ ID NO 11
<211> LENGTH: 153
<212> TYPE: DNA
<213> ORGANISM: ENTEROCOCCUS MUNDTII ST4SA

<400> SEQUENCE: 11
atgtcacaag tagtaggtgg aaaatactac ggtaatggag tctcatgtaa taaaaaaggg   60
tgcagtgttg attggggaaa agctattggc attattggaa ataattctgc tgcgaattta  120
gctactggtg gagcagctgg ttggaaaagt taa                               153

<210> SEQ ID NO 12
<211> LENGTH: 50
<212> TYPE: PRT
<213> ORGANISM: ENTEROCOCCUS MUNDTII ST4SA

<400> SEQUENCE: 12

Met Ser Gln Val Val Gly Gly Lys Tyr Tyr Gly Asn Gly Val Ser Cys
1               5                   10                  15

Asn Lys Lys Gly Cys Ser Val Asp Trp Gly Lys Ala Ile Gly Ile Ile
            20                  25                  30

Gly Asn Asn Ser Ala Ala Asn Leu Ala Thr Gly Gly Ala Ala Gly Trp
        35                  40                  45

Lys Ser
    50

<210> SEQ ID NO 13
<211> LENGTH: 2025
<212> TYPE: DNA
<213> ORGANISM: ENTEROCOCCUS MUNDTII ST4SA

<400> SEQUENCE: 13
atgcagatga tttaaataa ttttcattca tggatttcag tggaagtttt aagagactta    60
actgaaaccg attctgaagg tacctgtgca ttaggtatag ttaacggatt tgctaaatta  120
ggaataaatt gtgaagccta taagctaat agtgatgtat ggaaagaaaa tgagttcaat   180
tatcccgtaa ttgctaatat agtaacgaat aatcaatttc ttcattattg tattgtatat  240
ggtgtgaaaa aagagaaatt gttaatagct gaccctgcga ttggaaaata caagaatca   300 atagaaaagt tcaacaacaa atggactggt gttatttag ttgctgaaaa gactcctgat   360
ttccaaccca taataatac aaaaaaaagt tttttttctt caataagttt attaaaagat   420
caatataaaa aaattttatt ggtgatatta tcttcattaa taataacaat tataggaata  480
ctatcaagtt actattttag aatttttaata gattggttac ttcctgaaaa agacttttta  540
aatctattta tgatatcaat tagctatatc ataggcattt ttataacaag tatatttgaa  600
attaccagaa gatataattt agaaaagcta ggacaagatg taggtagaag catttatttt  660
aaatatttag aacatatttt catttttacca gcttcctttt tttctaaaag aaaaactgga  720
gatattgtct ctagattttc tgatgctaat aaaattatag aagctttagc tagctttact  780
```

```
atatctattt ttttagattt aagttcagtc attgttgtgg ggattatatt gatcaatatt      840
aataaacaat tatttttaat aacgttaagt tctattccat tttatatact aattatatta      900
ggatcaaata aaaaaatgag tcgattaaac ggagaagaga tgcaaacaaa ttcaatagtt      960
gattctaatt ttattgaagg attaaacgga atatatacta taaaagcact ttgtagtgag     1020
aataagattg taaatcaaat atatagaagt ttaaataaat tttttgatgt atcactaaag     1080
agaaatatgt atgattctat aattcaaaat ttaaaaattt tggtttctct tttaacctcg     1140
gcttttgtat tatggcttgg ttcgtattat gttatcaatg gagaaattac aataggagaa     1200
ctaataactt tcaattcatt atctatattt ttttctacac ctctacaaaa tataataaat     1260
ctacaagaaa aattccaaaa agcacaagtt gcaataatc ggcttaacga tgtattttct     1320
ataaataatg aaaataaaga caagtttatt catttggcta aattaactga aaaagcaacg     1380 attcatttg aaaatgtata ttttagttat tctactaaat atcctaatgt gttagataat     1440
atgagttttt ctctacctgt gagtaaaaat ataggaataa aaggtgatag tggtgctggg     1500
aaatcaactt tagcacaact tctagctgga ttttactctc cagataatgg aagaatttgt     1560
ataaatgagc aaaatattga aaatattaat agaaaagatt tacgtaagtt gattacctat     1620
gtgcctcaag aatcttttat tatgagtgga actattaaag acaatttatt tttaggttta     1680
gaaagtattc ctgatgaaca agaactcgaa aaagtactga aagatacttg tttatggagt     1740
tatattactg cgcctcctct aggacttgat acgtatctag aagaaatgg tgcgaattta     1800 tcaggtggtc aaaagcaaag aattgcttta gcaagagttt tattattagg aagtaaaatt     1860
ttattattag atgaagctac gagtgctcta gattctaaaa ctgaaatgct gatttttagaa     1920 aaattattaa agtaccctaa taagtcaatc attatgatat ctcataatga taaattaata     1980
gacaagtgtg acttaatcat tgatttagac gaaagggatt cataa                    2025
```

<210> SEQ ID NO 14
<211> LENGTH: 674
<212> TYPE: PRT
<213> ORGANISM: ENTEROCOCCUS MUNDTII ST4SA

<400> SEQUENCE: 14

```
Met Gln Met Ile Leu Asn Asn Phe His Ser Trp Ile Ser Val Glu Val
1               5                   10                  15

Leu Arg Asp Leu Thr Glu Thr Asp Ser Glu Gly Thr Cys Ala Leu Gly
            20                  25                  30

Ile Val Asn Gly Phe Ala Lys Leu Gly Ile Asn Cys Glu Ala Tyr Lys
        35                  40                  45

Ala Asn Ser Asp Val Trp Lys Glu Asn Glu Phe Asn Tyr Pro Val Ile
    50                  55                  60

Ala Asn Ile Val Thr Asn Asn Gln Phe Leu His Tyr Cys Ile Val Tyr
65                  70                  75                  80

Gly Val Lys Lys Glu Lys Leu Leu Ile Ala Asp Pro Ala Ile Gly Lys
                85                  90                  95

Tyr Lys Glu Ser Ile Glu Lys Phe Asn Asn Lys Trp Thr Gly Val Ile
            100                 105                 110

Leu Val Ala Glu Lys Thr Pro Asp Phe Gln Pro Ile Asn Asn Thr Lys
        115                 120                 125

Lys Ser Phe Phe Ser Ser Ile Ser Leu Leu Lys Asp Gln Tyr Lys Lys
    130                 135                 140

Ile Leu Leu Val Ile Leu Ser Ser Leu Ile Ile Thr Ile Ile Gly Ile
145                 150                 155                 160
```

```
Leu Ser Ser Tyr Tyr Phe Arg Ile Leu Ile Asp Trp Leu Leu Pro Glu
                165                 170                 175

Lys Asp Phe Leu Asn Leu Phe Met Ile Ser Ile Ser Tyr Ile Ile Gly
            180                 185                 190

Ile Phe Ile Thr Ser Ile Phe Glu Ile Thr Arg Arg Tyr Asn Leu Glu
                195                 200                 205

Lys Leu Gly Gln Asp Val Gly Arg Ser Ile Leu Phe Lys Tyr Leu Glu
        210                 215                 220

His Ile Phe Ile Leu Pro Ala Ser Phe Phe Ser Lys Arg Lys Thr Gly
225                 230                 235                 240

Asp Ile Val Ser Arg Phe Ser Asp Ala Asn Lys Ile Ile Glu Ala Leu
                245                 250                 255

Ala Ser Phe Thr Ile Ser Ile Phe Leu Asp Leu Ser Ser Val Ile Val
                260                 265                 270

Val Gly Ile Ile Leu Ile Asn Ile Asn Lys Gln Leu Phe Leu Ile Thr
            275                 280                 285

Leu Ser Ser Ile Pro Phe Tyr Ile Leu Ile Leu Gly Ser Asn Lys
            290                 295                 300

Lys Met Ser Arg Leu Asn Gly Glu Glu Met Gln Thr Asn Ser Ile Val
305                 310                 315                 320

Asp Ser Asn Phe Ile Glu Gly Leu Asn Gly Ile Tyr Thr Ile Lys Ala
                325                 330                 335

Leu Cys Ser Glu Asn Lys Ile Val Asn Gln Ile Tyr Arg Ser Leu Asn
                340                 345                 350

Lys Phe Phe Asp Val Ser Leu Lys Arg Asn Met Tyr Asp Ser Ile Ile
            355                 360                 365

Gln Asn Leu Lys Ile Leu Val Ser Leu Leu Thr Ser Ala Phe Val Leu
    370                 375                 380

Trp Leu Gly Ser Tyr Tyr Val Ile Asn Gly Glu Ile Thr Ile Gly Glu
385                 390                 395                 400

Leu Ile Thr Phe Asn Ser Leu Ser Ile Phe Phe Ser Thr Pro Leu Gln
                405                 410                 415

Asn Ile Ile Asn Leu Gln Glu Lys Phe Gln Lys Ala Gln Val Ala Asn
            420                 425                 430

Asn Arg Leu Asn Asp Val Phe Ser Ile Asn Asn Glu Asn Lys Asp Lys
                435                 440                 445

Phe Ile His Leu Ala Lys Leu Thr Glu Lys Ala Thr Ile Thr Phe Glu
            450                 455                 460

Asn Val Tyr Phe Ser Tyr Ser Thr Lys Tyr Pro Asn Val Leu Asp Asn
465                 470                 475                 480

Met Ser Phe Ser Leu Pro Val Ser Lys Asn Ile Gly Ile Lys Gly Asp
                485                 490                 495

Ser Gly Ala Gly Lys Ser Thr Leu Ala Gln Leu Leu Ala Gly Phe Tyr
        500                 505                 510

Ser Pro Asp Asn Gly Arg Ile Cys Ile Asn Glu Gln Asn Ile Glu Asn
            515                 520                 525

Ile Asn Arg Lys Asp Leu Arg Lys Leu Ile Thr Tyr Val Pro Gln Glu
            530                 535                 540

Ser Phe Ile Met Ser Gly Thr Ile Lys Asp Asn Leu Phe Leu Gly Leu
545                 550                 555                 560

Glu Ser Ile Pro Asp Glu Gln Glu Leu Glu Lys Val Leu Lys Asp Thr
                565                 570                 575

Cys Leu Trp Ser Tyr Ile Thr Ala Pro Pro Leu Gly Leu Asp Thr Tyr
```

```
                    580              585              590
Leu Glu Glu Asn Gly Ala Asn Leu Ser Gly Gly Gln Lys Gln Arg Ile
            595                 600                 605

Ala Leu Ala Arg Val Leu Leu Leu Gly Ser Lys Ile Leu Leu Leu Asp
        610                 615                 620

Glu Ala Thr Ser Ala Leu Asp Ser Lys Thr Glu Met Leu Ile Leu Glu
625                 630                 635                 640

Lys Leu Leu Lys Tyr Pro Asn Lys Ser Ile Ile Met Ile Ser His Asn
            645                 650                 655

Asp Lys Leu Ile Asp Lys Cys Asp Leu Ile Ile Asp Leu Asp Glu Arg
        660                 665                 670

Asp Ser

<210> SEQ ID NO 15
<211> LENGTH: 297
<212> TYPE: DNA
<213> ORGANISM: ENTEROCOCCUS MUNDTII ST4SA

<400> SEQUENCE: 15
atgagtaatt taaagtggtt ttctggtgga gacgatcgac gtaaaaaagc agaagtgatt     60
attactgaat tattagatga tttagagata gatcttggaa atgaatctct tcgaaaagta    120
ttaggctcct atcttgaaaa gttgaaaaat gaaggaactt cagttccatt agtttttaagt   180 cgtatgaata tagagatatc taatgcaata aaaaaagacg gtgtatcgtt aaatgaaaat    240
caatctaaaa aattaaaaga actcatatct atatctaata ttagatatgg atattag      297

<210> SEQ ID NO 16
<211> LENGTH: 98
<212> TYPE: PRT
<213> ORGANISM: ENTEROCOCCUS MUNDTII ST4SA

<400> SEQUENCE: 16

Met Ser Asn Leu Lys Trp Phe Ser Gly Gly Asp Asp Arg Arg Lys Lys
1               5                   10                  15

Ala Glu Val Ile Ile Thr Glu Leu Leu Asp Asp Leu Glu Ile Asp Leu
            20                  25                  30

Gly Asn Glu Ser Leu Arg Lys Val Leu Gly Ser Tyr Leu Glu Lys Leu
        35                  40                  45

Lys Asn Glu Gly Thr Ser Val Pro Leu Val Leu Ser Arg Met Asn Ile
    50                  55                  60

Glu Ile Ser Asn Ala Ile Lys Lys Asp Gly Val Ser Leu Asn Glu Asn
65                  70                  75                  80

Gln Ser Lys Lys Leu Lys Glu Leu Ile Ser Ile Ser Asn Ile Arg Tyr
                85                  90                  95

Gly Tyr

<210> SEQ ID NO 17
<211> LENGTH: 29
<212> TYPE: PRT
<213> ORGANISM: ENTEROCOCCUS MUNDTII ST4SA

<400> SEQUENCE: 17

Lys Tyr Tyr Gly Asn Gly Val Ser Cys Asn Lys Lys Gly Cys Ser Val
1               5                   10                  15

Asp Trp Gly Lys Ala Ile Gly Ile Ile Gly Asn Asn Ser
            20                  25
```

```
<210> SEQ ID NO 18
<211> LENGTH: 24
<212> TYPE: PRT
<213> ORGANISM: ENTEROCOCCUS MUNDTII ST4SA

<400> SEQUENCE: 18

Lys Ala Ile Gly Leu Leu Gly Asn Asn Ser Ala Ala Asn Leu Ala Thr
1               5                   10                  15

Gly Gly Ala Ala Gly Trp Lys Ser
            20

<210> SEQ ID NO 19
<211> LENGTH: 87
<212> TYPE: DNA
<213> ORGANISM: Enterococcus mundtii

<400> SEQUENCE: 19
aaatactacg gtaatggagt ctcatgtaat aaaaaagggt gcagtgttga ttggggaaaa      60
gctattggca ttattggaaa taattct                                         87

<210> SEQ ID NO 20
<211> LENGTH: 72
<212> TYPE: DNA
<213> ORGANISM: Enterococcus mundtii

<400> SEQUENCE: 20
aaagctattg gcattattgg aaataattct gctgcgaatt tagctactgg tggagcagct      60
ggttggaaaa gt                                                         72
```

PROBIOTIC STRAIN AND ANTIMICROBIAL PEPTIDE DERIVED THEREFROM

FIELD OF THE INVENTION

THIS INVENTION relates to a peptide obtained from a strain of *Enterococcus mundtii* and to a probiotic composition of a strain of *Enterococcus mundtii*. More particularly, the invention relates to a peptide obtained from a strain of *Enterococcus mundtii*, the gene coding for the peptide and various applications of the strain which produces the peptide and the peptide itself.

BACKGROUND TO THE INVENTION

Lactic acid bacteria play an important role in maintaining the balance of normal gastro-intestinal microflora. Diet, stress, microbial infection and intestinal diseases disturb the microbial balance, which often leads to a decrease in the number of viable lactic acid bacteria (especially lactobacilli and bifidobacteria) in the intestinal tract. The subsequent uncontrolled proliferation of pathogenic bacteria then leads to diarrhea and other clinical disorders such as cancer, inflammatory disease and ulcerative colitis.

One of the key properties of probiotic lactic acid bacteria is the adhesion of cells to epithelial cells or intestinal mucus. This requires strong interaction between receptor molecules on epithelial cells and bacterial surfaces. Adhesion of probiotic cells prevent the adhesion of pathogens and stimulate the immune system. The latter is achieved by interacting with mucosal membranes, which in turn sensitises the lymphoids. Another important characteristic of probiotics is survival at low pH and high bile salts.

Certain strains of bifidobacteria, lactobacilli and enterococci associated with the intestines of humans and animals are known to produce bacteriocins (antimicrobial peptides). The role of these peptides, and their significance in controlling the proliferation of pathogenic bacteria in the intestinal tract, is uncertain. However, as concluded from recent reports on bacteriocins active against Gram-negative bacteria, there may be renewed interest in these peptides and their interaction with intestinal pathogens. Many of the latter bacteriocins are produced by lactic acid bacteria normally present in the intestinal tract, viz. the *Lactobacillus acidophilus*-group, *Lactobacillus reuteri*, *Lactobacillus casei*, *Lactobacillus fermentum*, *Lactobacillus plantarum*, *Lactobacilsus pentosus*, *Lactobacillus paracasei* subsp. *paracasei* and *Enterococcus faecalis*.

The invention describes a strain of *Enterococcus mundtii* that resists intestinal stress conditions (e.g. low pH, bile salts, salts, pancreatic enzymes) and produces a broad-spectrum antibacterial peptide (peptide ST4SA).

BRIEF DESCRIPTION OF THE INVENTION

According to one aspect of the present invention there is provided an isolated peptide from the bacterium *Enterococcus mundtii*, said peptide having the following amino acid sequence:

(SEQ. ID. NO. 12)
MSQVVGGKYYGNGVSCNKKGCSVDWGKAIGIIGNNSAANLATGGAAGWK
S;

a fragment thereof having antimicrobial activity;
muteins and derivatives thereof having antimicrobial activity;
covalently bound bridge constructs thereof having antimicrobial activity; or
sequences having more than about 95% homology, preferably more than 85% homology, most preferably more than about 75% homology to said amino acid sequence, having antimicrobial activity.

According to another aspect of the present invention there is provided an isolated nucleotide sequence which codes for peptide ST4SA of the bacterium *Enterococcus mundtii*.

The isolated nucleotide sequence may comprise the following nucleotide sequence:

(SEQ. ID. NO. 11)
ATGTCACAAGTAGTAGGTGGAAAATACTACGGTAATGGAGTCTCATGTAA

TAAAAAAGGGTGCAGTGTTGATTGGGGAAAAGCTATTGGCATTATTGGAA

ATAATTCTGCTGCGAATTTAGCTACTGGTGGAGCAGCTGGTTGGAAAAG

T;

the complement thereof;
a fragment thereof capable of producing, following expression thereof, a peptide having antimicrobial activity; or
nucleotide sequences which hybridize under strict hybridization conditions thereto.

Strict hybridization conditions correspond to a wash of 2×SSC, 0.1% SDS, at 50° C.

The nucleotide sequence may be included in a vector, such as an expression vector or transfer vector in the form of a plasmid. The vector may include nucleic acid sequences encoding selection attributes, such as antibiotic resistance selection attributes, or other marker genes. Accordingly, the invention extends to a recombinant plasmid adapted for transformation of a microbial host cell, said plasmid comprising a plasmid vector into which a nucleotide sequence which codes for the antimicrobial peptide of the invention has been inserted.

The cell may be a prokaryotic or a eukaryotic cell, such as a bacterial cell or yeast cell. The nucleotide sequence may be incorporated transiently or constitutively into the genome of the cell. Accordingly, the invention extends to a transformed microbial cell which includes a recombinant plasmid, said plasmid comprising a plasmid vector into which a nucleotide sequence which codes for the antimicrobial peptide of the invention has been inserted.

According to a further aspect of the invention there is provided an isolated peptide from the bacterium *Enterococcus mundtii*, the peptide having antimicrobial activity.

The bacterium *Enterococcus mundtii* which produces the isolated peptide identified above has been deposited with the ATCC, 10801 University Boulevard, Manassas, Va. 20110, on Dec. 13, 2005, under the assigned number PTA-7278, in accordance with the Budapest Treaty deposit requirements. All restrictions upon public access to the deposit will be removed and sample replaced if viable samples cannot be dispersed by the depository, as necessary, upon allowance of the present application. The specific strain of the bacterium *Enterococcus mundtii* that produces the isolated peptide identified above has been designated as strain ST4SA. Accordingly, the invention extends to a substantially pure culture of *Enterococcus mundtii* strain ST4SA deposited with the ATCC under the assigned number PTA-7278, said culture capable of producing peptide ST4SA in a recoverable quantity upon fermentation in a nutrient medium containing assimilable sources of carbon, nitrogen, and inorganic substances.

Another aspect of the invention relates to a process for the production of a peptide of the invention which comprises cultivating *Enterococcus mundtii* strain ST4SA in a nutrient medium under micro-aerophilic conditions at a temperature of between 10° C. and 45° C., until a recoverable quantity of said peptide is produced, and recovering said peptide. Preferably the cultivation occurs at a temperature of about 37° C.

The nutrient medium may be selected from any one or more of the group including: corn steep liquor; cheese whey powder; MRS broth; yeast extract; and molasses. Preferably, the nutrient medium is MRS broth at pH 6 to 6.5.

The isolated peptide of the invention may be used as an antimicrobial agent in a liquid formulation or a gel formulation as a topical treatment for, for example, ear infections, such as mid-ear infections, and also throat, eye, or skin infections. The liquid formulation may also be for use as a liquid supplement to meals. The peptide may also further be used as an antimicrobial agent in a spray for treatment of, for example, sinus infections, sinusitis, tonsillitis, throat infections or rhinitis. The peptide may also be in the form of a lyophilized powder.

The isolated peptide may also be used as an antimicrobial agent following encapsulation in a polymer. The invention extends, according to another aspect thereof, to a polymer having incorporated therein an antimicrobial amount of peptide ST4SA. This polymer may then be used in a formulation for topical treatment of infections such as, for example, skin infections, or may be used for incorporation in implants or medical devices such as, for example, ear grommets, catheters, ostomy tubes and pouches, stents, suture material, hygiene products such as feminine hygiene products, contact lenses, contact lens solution, or for incorporation in wound dressings. The encapsulation of the antimicrobial peptide in the polymer leads to a slow release of the antimicrobial peptide and an extended period of treatment of a microbial infection.

The isolated peptide may be included in a concentration of 100 000 AU/ml (Arbitrary Units) to 300 000 AU/ml of polymer, preferably about 200 000 AU/ml of polymer.

The peptide further may be used as an antimicrobial agent by being incorporated into ointment, lotion, or cream formulations. These ointment, lotion, or cream formulations may be used to treat infections. The peptide may also further be used as an antimicrobial agent by being incorporated into liquid formulations such as, for example, contact lens rinsing fluid, or it may be incorporated into the contact lenses themselves. Accordingly, the invention provides, as another aspect thereof, an antimicrobial ointment, lotion, or cream containing an antimicrobial peptide of the invention.

In another form of the invention the peptide may be used as an antimicrobial agent by being incorporated into packaging material such as, for example, plastic, for use in the manufacture of aseptic packaging.

In an even further form of the invention the peptide may be used as part of a broad-spectrum probiotic of the bacterium *Enterococcus mundtii* in a tablet form or in a capsule form or it may be in an edible form such as, for example, a sweet or chewing gum.

According to a further aspect of the invention there is provided a probiotic composition including a biologically pure culture comprising a therapeutically effective concentration of *Enterococcus mundtii* strain ST4SA. The strain may be included in a concentration of about $10^6$ to $10^9$, preferably about $10^8$ viable cells (cfu) per ml of probiotic composition.

In one form of the invention the probiotic composition may be used to reduce pathogenic bacteria in an animal or a human.

In another form of the invention the probiotic composition may be used to reduce pathogenic viruses in an animal or a human.

The probiotic composition may be in the form of a powder, a liquid, a gel, a tablet, or may be incorporated into a foodstuff. The probiotic composition in a liquid form may be used as a liquid supplement to meals. The strain may be included in a concentration of about $10^6$ to $10^9$, preferably about $10^8$ viable cells (cfu) per ml of liquid supplement.

The probiotic composition may be administered to an animal or human at a final concentration of between $10^3$ and $10^6$ cfu/ml, preferably between $10^5$ and $10^6$ cfu/ml, most preferably about $3 \times 10^5$ cfu/ml.

According to another aspect of the invention there is provided a method of treating a bacterial infection condition in an animal or human, the method including the step of exposing an infected area of the animal or human to a substance or composition selected from the group comprising any one or more of:

a pharmaceutically effective amount of the *Enterococcus mundtii* strain of the invention; and a pharmaceutically effective amount of the antimicrobial peptide of the invention.

Accordingly, the invention extends also to use of a therapeutically effective amount of the *Enterococcus mundtii* strain of the invention in the manufacture of a medicament for use in a method of treating a bacterial infection in an animal or human.

The method may include the step of exposing bacterial species to the antimicrobial peptide of the invention at a concentration of 100 000 to 300 000 AU/ml, preferably about 200 000 AU/ml.

The invention extends also to use of a therapeutically effective amount of the antimicrobial peptide of the invention in the manufacture of a medicament for use in a method of treating a bacterial infection in an animal or human.

The invention further provides a substance or composition for use in a method of treating a bacterial infection in an animal or human, said substance or composition comprising the *Enterococcus mundtii* strain of the invention, and said method comprising administering a therapeutically effective amount of the substance or composition to the animal or human.

The invention further provides a substance or composition for use in a method of treating a bacterial infection in an animal or human, said substance or composition comprising the antimicrobial peptide of the invention, and said method comprising administering a therapeutically effective amount of the substance or composition to the animal or human.

The bacterial infection may be an infection caused by any one or more of: *Acinetobacter baumanii*; *Bacillus cereus*; *Clostridium tyrobutyricum*; *Enterobacter cloacae*; *Escherichia coli*; *Klebsiella pneumoniae*; *Listeria innocua*; *Pseudomonas aruginosa*; *Staphylococcus aureus*; *Staphylococcus carnosus*; *Streptococcus caprinus*; *Streptococcus (Enterococcus) faecalis*; or *Streptococcus pneumoniae*.

According to a still further aspect of the invention there is provided a method of inhibiting growth of bacterial species, the method including the step of exposing bacterial species to an effective amount of the antimicrobial peptide of the invention. The bacterial species may be selected from the group including:

*Acinetobacter baumanii*; *Bacillus cereus*; *Clostridium tyrobutyricum*; *Enterobacter cloacae*; *Escherichia coli*; *Klebsiella pneumoniae*; *Listeria innocua*; *Pseudomonas aruginosa*; *Staphylococcus aureus*; *Staphylococcus carno-* sus; *Streptococcus caprinus*; *Streptococcus (Enterococcus) faecalis*; and *Streptococcus pneumoniae*.

The method may include the step of exposing bacterial species to the antimicrobial peptide of the invention at a concentration of 100 000 to 300 000 AU/ml, preferably about 200 000 AU/ml.

According to one aspect of the present invention there is provided an isolated transporter peptide from the bacterium *Enterococcus mundtii*, said peptide having the amino acid sequence of SEQ. ID. NO. 14:
- a fragment thereof;
- muteins and derivatives thereof; or
- sequences having more than about 90% homology, preferably more than 80% homology, most preferably more than about 70% homology to said amino acid sequence, having antimicrobial activity.

According to another aspect of the present invention there is provided an isolated nucleotide sequence which codes for ST4SA transporter peptide of the bacterium *Enterococcus mundtii*. The isolated nucleotide sequence may comprise the nucleotide sequence of SEQ. ID. NO. 13;
- the complement thereof;
- a fragment thereof; or
- nucleotide sequences which hybridize under strict hybridization conditions thereto.

According to one aspect of the present invention there is provided an isolated immunity peptide from the bacterium *Enterococcus mundtii*, said peptide having the amino acid sequence of SEQ. ID. NO. 16:
- a fragment thereof;
- muteins and derivatives thereof; or
- sequences having more than about 90% homology, preferably more than 80% homology, most preferably more than about 70% homology to said amino acid sequence, having antimicrobial activity.

According to another aspect of the present invention there is provided an isolated nucleotide sequence which codes for ST4SA immunity/adhesion peptide of the bacterium *Enterococcus mundtii*. The isolated nucleotide sequence may comprise the nucleotide sequence of SEQ. ID. NO. 15;
- the complement thereof
- a fragment thereof; or
- nucleotide sequences which hybridize under strict hybridization conditions thereto.

The invention extends, according to another aspect thereof, to a primer selected from the group consisting of SEQ. ID. NO. 1 to SEQ. ID. NO. 10. Accordingly, the invention extends also to a primer pair selected from the following group:
- primer pair comprising SEQ. ID. NO. 1 and SEQ. ID. NO. 2;
- primer pair comprising SEQ. ID. NO. 3 and SEQ. ID. NO. 4;
- primer pair comprising SEQ. ID. NO. 5 and SEQ. ID. NO. 6;
- primer pair comprising SEQ. ID. NO. 7 and SEQ. ID. NO. 8; and
- primer pair comprising SEQ. ID. NO. 9 and SEQ. ID. NO. 10.

The invention extends also to the use of the primer pair of SEQ. ID. NO. 1 and SEQ. ID. NO. 2 in the identification of *Enterococcus mundtii*.

BRIEF DESCRIPTION OF THE DRAWINGS

For a better understanding of the present invention, and to show how the same may be carried into effect, reference will now be made, by way of example only, to the accompanying drawings and tables in which;

FIG. 8 is a DNA sequence of the peptide ST4SA structural gene (A), transporter gene (B) and immunity gene (C);

FIGS. 9A and 9B show the influence of growth medium components on peptide ST4 production;

FIG. 10 is a graphic presentation of the production of peptide ST4SA in MRS broth;

Figure 1:
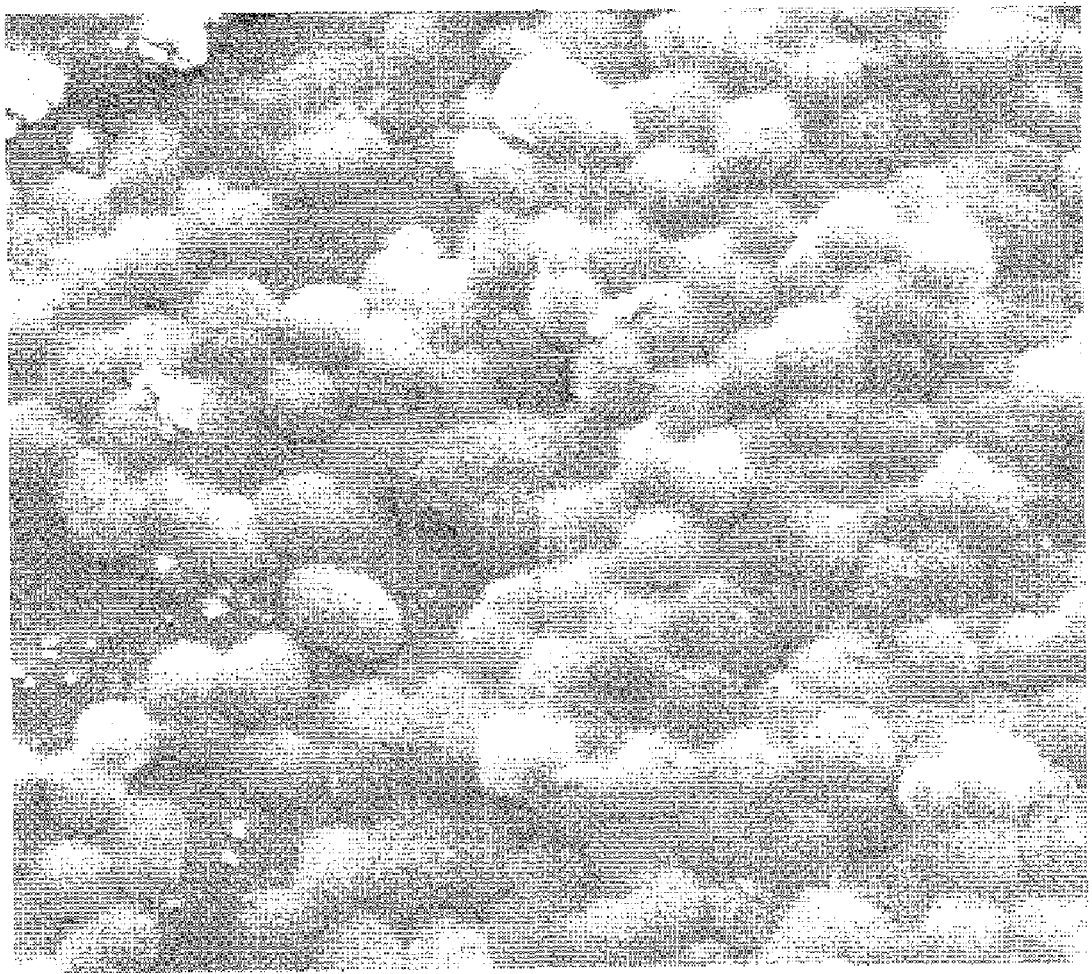
FIG. 1 is an image of cell morphology of *Enterococcus mundtii* strain ST4SA as observed by SEM (scanning electron microscopy)

Table 1 shows phenotypic characteristics of strain ST4SA (sugar fermentation reactions);

Table 2 shows differential characteristics of strain ST4SA;

Table 3 shows the effect of enzymes, temperature, pH and detergents on peptide ST4SA;

Table 4 shows an activity spectrum of peptide ST4SA;

Table 5 shows activity of peptide ST4SA on paper disks;

Table 6 shows the comparison of the activity of peptide ST4SA to commonly used antibiotics;

Table 7 shows adhesion of peptide ST4SA to pathogens;

Table 8 shows extracellular DNA recorded after treatment of pathogens with peptide ST4SA;

Table 9 shows β-galactosidase activity recorded after the treatment of pathogens with peptide ST4SA;

Table 10 shows operation of the GIM (computerized);

Table 11 shows survival of strain ST4SA and production of peptide ST4SA in the GIM—Listeria monocytogenes was used as target organism (pathogen). The values are an average of three trials. The nutrients used were NAN Pelargon (Nestlé) and MRS (De Man Rogosa medium, Biolab), respectively;

Table 12 shows antibiotic resistance of strain ST4SA;

Table 13 shows growth of strain ST4SA in the presence of different concentrations of Trimethoprim-sulfamethoxazole (TMP-SMX) and Metronidazole;

Table 14 shows virulence factors that were assayed;

Table 15 shows the adhesion of strain ST4SA to Caco-2 cell lines by plate counting (control);

Table 16 shows competitive exclusion of strain ST4SA and L. monocytogenes;

Table 17 shows weight figures for rats administered strain ST4SA, Lactovita or unsupplemented water;

Table 18 shows β-glucuronidase activity in faecal samples of male Wistar rats during a (A) 107 day Lactovita study and (B) a 50 day strain ST4SA study. Values are mM ρ-nitrophenol released per 2 hours. Standard error values are shown in parenthesis;

Table 19 shows the purification of peptide ST4SA in MRSf (MRS filtrate) medium;

Table 20 shows results for pure CSL, molasses and CWp tested as growth media for peptide ST4SA production;

Table 21 shows a full factorial design (FFD) with CSL and CWp as components to determine which media had the most significant effect on peptide ST4SA production;

Table 22 shows the results of CSL supplemented with MRS components for ST4SA activity optimization;

Table 23 shows high and low concentrations of MRS components and CSL;

Table 24 shows the $2^{10-5}$ FrFD design;

Table 25 shows an analysis of Variance Table for a $2^{10-5}$ FrFD design;

Table 26 shows a $2^2$ FFD with 3 centre points for determination of CSL and YE concentrations;

Table 27 shows the uptake of carbon during fermentation;

Table 28 shows the results of resistance testing of E. mundtii ST4 against antibiotics and anti-inflammatory drugs;

Table 29 shows the effect of antibiotics and anti-inflammatory medicaments on adhesion of ST4SA to Caco-2 cells;

DETAILED DESCRIPTION OF THE INVENTION

The invention describes a strain of the bacterium Enterococcus mundtii that resists intestinal stress conditions (e.g. low pH, bile salts, salts, pancreatic enzymes) and produces a broad-spectrum antibacterial peptide, namely peptide ST4SA. The strain of Enterococcus mundtii which produces the peptide ST4SA has been deposited with the ATCC (American Type Culture Collection) and the assigned number is PTA-7278. Activity has been observed against a large number of Gram-positive and Gram-negative bacteria, most of these isolated from middle-ear infections and the intestine. Examples of bacteria inhibited are as follows: Acinetobacter baumanii, Bacillus cereus, Clostridium tyrobutyricum, Enterobacter cloacae, Escherichia coli, Klebsiella pneumoniae, Listeria innocua, Pseudomonas aruginosa, Staphylococcus aureus, Staphylococcus carnosus, Streptococcus caprinus, Streptococcus (Enterococcus) faecalis, Streptococcus pneumoniae, and a number of clinical strains of unidentified Gram-positive and Gram-negative bacteria isolated from infected middle-ear fluid samples. This is a large spectrum of activity, specifically against such a variety of human pathogens.

A number of broad-spectrum antibacterial peptides with activity against Gram-negative bacteria have been described, e.g. pentocin 35d produced by Lactobacillus pentosus, bacteriocin ST151 BR produced by Lactobacillus pentosus ST151 BR, a bacteriocin produced by Lactobacillus paracasei subsp. paracasei, thermophylin produced by Streptococcus termophylus, peptide AS-48 produced by Enterococcus faecalis, a bacteriocin produced by Lactococcus lactis KCA2386 and enterocin CRL35 produced by Enterococcus faecium. However, the activity spectrum of these peptides are much narrower than that recorded for peptide ST4SA, as may be seen from the species sensitive to peptide ST4SA listed above. The broad spectrum of activity, especially against pathogenic bacteria, renders peptide ST4SA ideal for the control of bacterial infections, especially middle-ear infections (since the peptide is active against a large variety of middle-ear pathogens), as well as pathogens involved in secondary wound infections (the peptide inhibits the growth of a number of these pathogens). Pathogens isolated from infected middle-ear fluid were Acinetobacter baumanii, Escherichia coli, Klebsiella pneumoniae, Pseudomonas aruginosa, Staphylococcus aureus, Staphylococcus carnosus, Streptococcus pneumoniae, and a number of unidentified Gram-positive and Gram-negative bacteria.

Materials and Methods

Isolation of Strain ST4SA and Identification to Species Level

Soy bean extract; obtained from soy beans that have been immersed in sterile distilled water for 4 h, was serially diluted and plated onto MRS Agar (Biolab), Biolab Diagnostics, Midrand, SA), supplemented with 50 mg/l Natamycin (Delvocid®, Gist-brocades, B.V., Delft, The Netherlands) to prevent fungal growth. The plates were incubated at 30° C. and 37° C. for two days.

Colonies were at random selected from plates with between 50 and 300 cfu (colony forming units) and screened for antimicrobial activity by overlaying them with a second layer of MRS Agar, supplemented with Delvocid® (50 mg/l). The plates were incubated at 30° C. and 37° C. for 48 h, in an anaerobic flask (Oxoid, New Hampshire, England) in the presence of a Gas Generation Kit (Oxoid). The colonies were covered with a third layer (ca. 10 ml) semi-solid (1.0% agar, w/v) BHI medium (Merck, Darmstadt, Germany), supplemented with 1 ml active growing cells (ca. $10^6$ cfu/ml) of *Lactobacillus casei, Enterococcus faecalis, Staphylococcus aureus, Pseudomonas aeruginosa, Klebsiella pneumoniae, Streptococcus pneumoniae* and *Staphylococcus aureus*, respectively. The plates were incubated at 37° C. for 24 h.

One of the colonies inhibited the largest variety of pathogens included in the test panel (Table 4) was re-inoculated into MRS broth (Biolab), followed by re-streaking to obtain pure cultures. The isolate was designated strain ST4SA. Antimicrobial activity was confirmed by using the agar-spot test method.

The cell morphology of strain ST4SA was studied by scanning electron microscopy (SEM) (see FIG. 1). Ten ml of an early-exponential phase ($OD_{600nm}$=0.2) culture of strain ST4SA was harvested by centrifugation and washed five times with sterile distilled water (3 000×g, 10 min, 4° C.). The pellet was resuspended in 500 μl sterile MilliQ water (Waters, Millipore) and then subjected to microscopy.

Further identification was accomplished by physiological (Table 2) and biochemical characteristics. Pigment formation was tested on Tryptic Soy Broth (Merck). Test for motility was also done. Sugar fermentation reactions (Table 1) were recorded by using the API 50 CHL and API 20 Strep test strips (Biomérieux, Marcy-l'Etiole, France) and compared with reactions listed for enterococci.

TABLE 1

| Compound/Derivative | *E. mundtii* ST4SA fermentation |
|---|---|
| Control | |
| Glycerol | + |
| Erythritol | |
| D-arabinose | |
| L-arabinose | ++ |
| Ribose | +++ |
| D-xylose | ++ |
| L-xylose | |
| Adonitol | |
| Methyl-xyloside | |
| Galactose | ++ |
| D-glucose | +++ |
| D-fructose | +++ |
| D-mannose | ++ |
| L-sorbose | |
| Rhamnose | ++ |
| Dulcitol | |
| Inositol | |
| Mannitol | ++ |
| Sorbitol | ++ |
| Methyl-D-mannoside | ++ |
| Methyl-D-glucoside | |
| Acetyl glucosamine | ++ |
| Amygdaline | +++ |
| Arbutine | +++ |
| Esculine | +++ |
| Salicine | +++ |
| Cellobiose | +++ |
| Maltose | +++ |
| Lactose | +++ |
| Melibiose | ++ |
| Saccharose | +++ |
| Trehalose | ++ |
| Inuline | |
| Melezitose | |
| D-raffinose | |
| Amidon | + |
| Glycogen | |

TABLE 1-continued

| Compound/Derivative | *E. mundtii* ST4SA fermentation |
|---|---|
| Xylitol | |
| B Gentiobiose | +++ |
| D-turanose | |
| D-lyxose | |
| D-tagatose | |
| D-fucose | |
| L-fucose | |
| D-arabitol | |
| L-arabitol | |
| Gluconate | |
| 2 ceto-gluconate | |
| 5 ceto-gluconate | |

TABLE 2

| Characteristic | Strain ST4SA |
|---|---|
| $CO_2$ from glucose | − |
| Growth at 10° C. | + |
| Growth at 45° C. | + |
| Growth in 6.5% NaCl | + |
| Growth in 18% NaCl | − |
| Growth at pH 4.4 | + |
| Growth at pH 9.6 | + |
| Lactic acid configuration | L |

Figure 2:
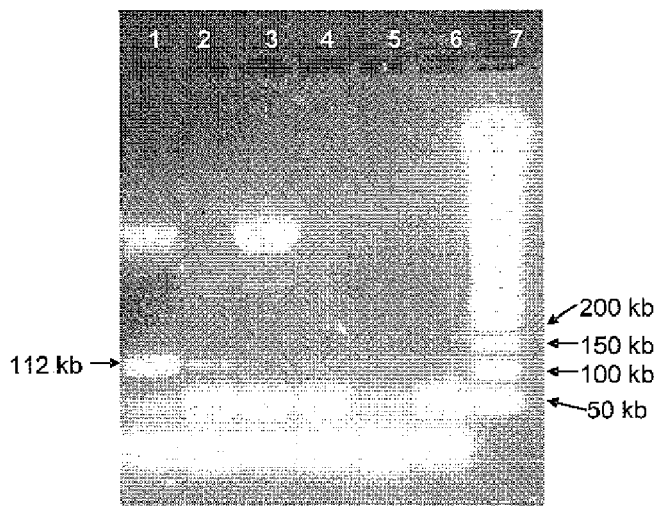
FIG. 2 is a photograph of an agarose gel showing a PCR product (DNA fragment) obtained by using genus-specific primers. A genus-specific DNA band of 112 kb, specific for *Enterococcus*, was obtained.
Figure 3:
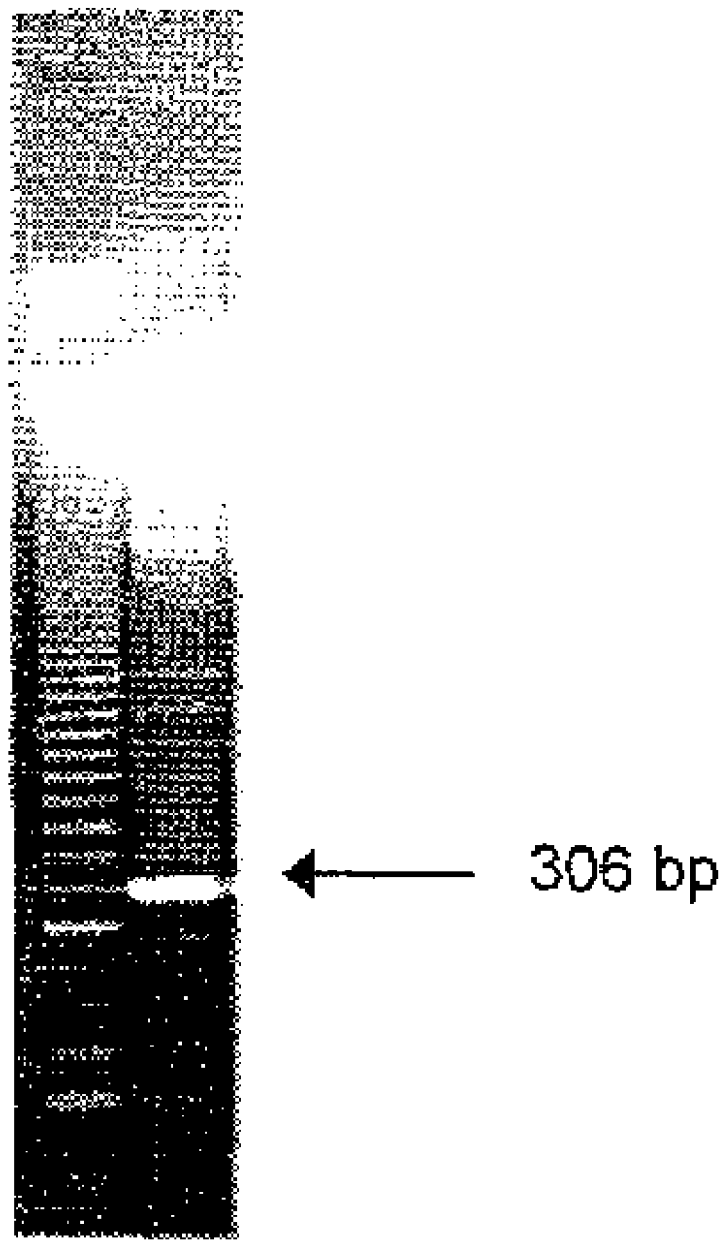
FIG. 3 is a photograph of an agarose gel showing a PCR product (DNA fragment) obtained by using species-specific primers. A species-specific DNA band of 306 bp, specific for *Enterococcus mundtii*, was obtained.

Further identification was by DNA banding patterns generated with primers specific for *Enterococcus* (FIG. 2) and *Enterococcus mundtii* (FIG. 3). A 50 bp DNA fragment (Amersham Bioscience, UK Limited, UK) was used as marker. Primers used to generate the 306 bp fragment (shown in FIG. 3) were designed from suitably conserved regions on 16S rDNA.

SEQ. ID. NO. 1: Forward primer: AACGAGCGCAACCC;

SEQ. ID. NO. 2: Reverse primer: GACGGGCGGTGTGTAC

Sequencing of the DNA fragment revealed 98% homology with conserved 16S rDNA fragments in GenBank.

Expression of Antimicrobial Activity

Antimicrobial activity was expressed as arbitrary units (AU) per ml cell-free supernatant. One AU is defined as the reciprocal of the highest dilution showing a clear zone of growth inhibition and is calculated as follows:

$a^b$×100, where "a" represents the dilution factor and "b" the last dilution that produces an inhibition zone of at least 2 mm in diameter. Activity is expressed per ml by multiplication with 100. *Lactobacillus casei* LHS was used as indicator strain.

Characterization of the Antimicrobial Substance

Strain ST4SA was cultured in MRS broth (Biolab) for 24 and 48 h at 30° C. The cells were harvested (8 000×g, 4° C., 15 min) and the cell-free supernatants adjusted to pH 6.0 with 6M NaOH. One ml of each supernatant was treated with catalase (Boehringer Mannheim) at 0.1 mg/ml (final concentration), Proteinase K (Roche, Indianapolis, Ind., USA), pronase, papain, pepsin and trypsin (Boehringer Mannheim GmbH, Germany), at 1 mg/ml and 0.1 mg/ml (final concentration), respectively. After incubation the enzymes were heat-inactivated (3 min at 100° C.) and tested for antimicrobial activity, as described before. The results are listed in Table 3.

Aliquots of peptide ST4SA were exposed to heat treatments of 30° C., 60° C. and 100° C. for 10, 30 and 90 min, respectively, and 121° C. for 20 min (Table 3). The samples were then tested for antimicrobial activity, as described before.

TABLE 3

| Treatment | Peptide ST4SA |
|---|---|
| Enzymes: | |
| α-amylase | + |
| Proteinase K | − |
| pepsin | − |
| pronase | − |
| pH: | |
| 2.0-12.0 | + |
| Heat: | |
| 30, 60, 100° C. for 10 min | + |
| 30, 60, 100° C. for 30 min | + |
| 30, 60, 100° C. for 90 min | + |
| 121° C. for 20 min | − |
| Detergents (1%): | |
| SDS | + |
| Tween 20, Tween 80 | + |
| urea | + |
| Triton X-100 | + |
| Triton X-114 | − |
| EDTA: | |
| 0.1 mM, 1.0 mM, 2.0 mM | + |

Key: − = no activity; + = activity zones of at least 5 mm in diameter

In a separate experiment, samples of peptide ST4SA were adjusted to pH values ranging from 2-12, incubated at 37° C. for 30 min, neutralised to pH 7, and then tested for antimicrobial activity (Table 3).

Isolation and Purification of Peptide ST4SA

Figure 4:
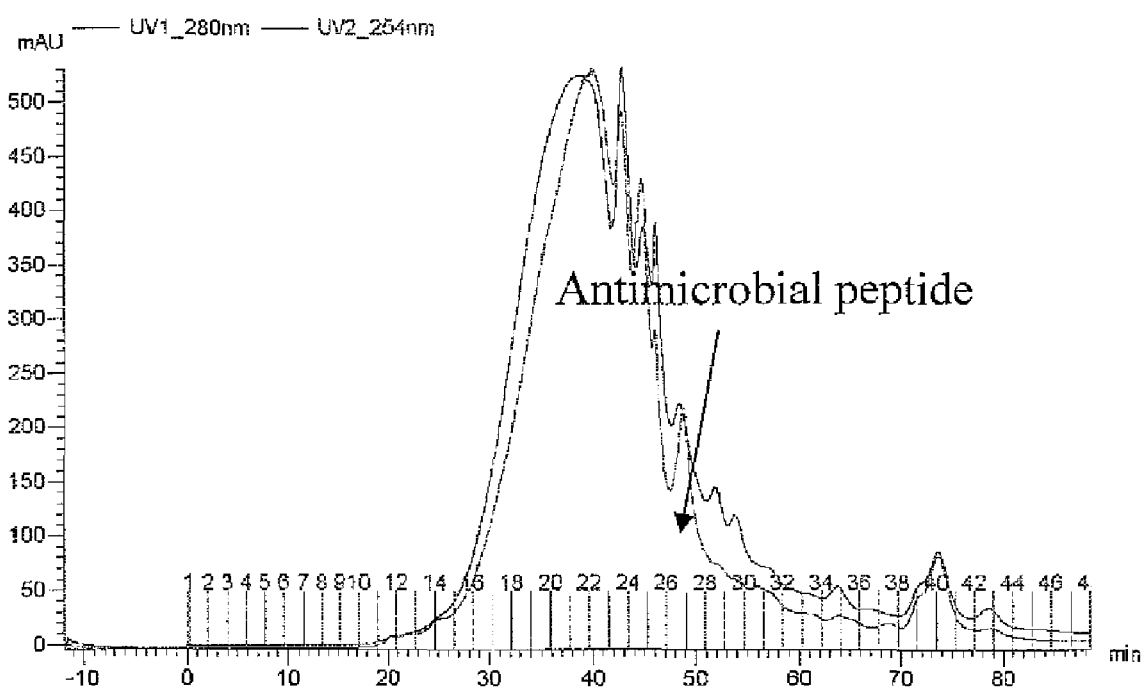
FIG. 4 is a graphic representation of peptide ST4SA separated by gel filtration (AKTA-purifier)

A 24 h-old culture of strain ST4SA was inoculated (2%, v/v, $OD_{600nm}$=8.0) into MRS broth (Biolab). Incubation was at 37° C., without agitation, for 20 h. The cells were harvested (8 000×g, 10 min, 4° C.) and the peptide precipitated from the cell-free supernatant with 80% saturated ammonium sulphate. The precipitate was resuspended in one tenth volume 25 mM ammonium acetate (pH 6.5), desalted against distilled water by using a 1000 Da cut-off dialysis membrane (Spectrum Inc., CA, USA) and loaded on a SepPak C18 column (Water Millipore, Mass., USA). The column was washed with 20% (v/v) iso-propanol in 25 mM ammonium acetate (pH 6.5) and the bacteriocin eluted with 40% iso-propanol in 25 mM ammonium acetate (pH 6.5). After drying under vacuum (Speed-Vac; Savant), the fractions were pooled and dissolved in 50 mM phosphate buffer, pH 6.5. The active fractions were further separated by gel filtration chromatography in a Superdex™ 75 column (Amersham Pharmacia Biotech) linked to an ÄKTApurifier (Amersham) (FIG. 4). Elution of the peptide from the column was with 50 mM phosphate buffer and 400 mM NaCl, pH 6.5. Peptides were detected at 254 nm and 280 nm, respectively. Fractions containing the active peptide were collected, dried under vacuum and stored at −20° C. Activity tests were performed by using the agar spot method.

Size Determination

Strain ST4SA was grown in MRS broth (Biolab) for 20 h at 30° C. The cells were harvested by centrifugation (8 000×g, 10 min, 4° C.) and peptide ST4SA precipitated from the cell-free supernatants with 80% saturated ammonium sulphate. The precipitate was resuspended in one tenth volume 25 mM ammonium acetate (pH 6.5), desalted against distilled water by using a 1000 Da cut-off dialysis membrane (Spectrum Inc., CA, USA) and separated by tricine-SDS-PAGE (FIG. 5A). A low molecular weight marker with sizes ranging from 2.35 to 46 kDa (Amersham International, UK) was used. The gels were fixed and one half overlaid with L. casei LHS ($10^6$ cfu/mL), embedded in Brain Heart Infusion (BHI) agar (Biolab), to determine the position of the active bacteriocin (FIG. 5B).

Cytotoxicity Tests on Peptide ST4SA

To determine if peptide ST4SA has cytotoxic properties, triplicate wells of confluent monolayers of monkey kidney Vero cells were grown in tissue culture plates for 48 h and then exposed to various concentrations of the antimicrobial peptide. After 48 h of incubation, cell viability was tested by treating the cells with tetrazolium salt MTT [3-(4,5-dimethylthiazol-2-gamma-2,5-diphenyl tetrazolium bromide] (Sigma). Production of a blue product (formazan), which forms after cleaving of MTT by succinate dehydrogenase was recorded.

The 50% cytotoxicity level ($CC_{50}$) was defined as the peptide concentration (μg/ml) required to reduce cell viability by 50%. According to the $CC_{50}$ results (cytotoxicity level), no cytotoxicity was recorded, that is, the peptide has zero (0) $CC_{50}$.

Plasmid Isolation

Total DNA was isolated. Plasmid DNA was isolated, after which the DNA was further purified by CsCl density gradient centrifugation. The DNA was separated on an agarose gel (FIG. 6). Lambda DNA digested with EcoRI and HindIII (Promega, Madison, USA) was used as molecular weight marker.

Plasmid Curing

Curing experiments were conducted. Cells of Ent. mundtii ST4SA were incubated in the presence of novobiocin (1-25 μg ml$^{-1}$) for 72 h at 37° C. The culture which grew at the highest concentration of novobiocin was serially diluted with sterile saline and plated out onto MRS agar plates. After overnight incubation at 37° C., the colonies were replica-plated and the original plates overlaid with cells of Enterococcus faecalis LMG 13566. After a further 16 h of incubation at 37° C., the colonies were checked for loss of antimicrobial activity.

Conjugative Transfer Experiments

Filter mating experiments were done. An overnight grown culture (0.25 ml) of Ent. mundtii ST4SA and Ent. faecalis FA2-2 were added to 4.5 ml MRS, mixed and filtered through a 0.45 μm pore-size sterile membrane filter (HAWP, Millipore). The membrane was placed onto a MRS agar plate and incubated overnight at 37° C. The cells were washed from the filter into 1 ml MRS, serially diluted and plated onto MRS agar plates containing 25 μg ml$^{-1}$ fusidic acid, 25 μg ml$^{-1}$ rifampicin and 2000 AU ml$^{-1}$ crude peptide ST4SA. The experiment was repeated with Ent faecalis OGX1 as recipient. In this case the selection was done on plates containing 1 mg ml$^{-1}$ streptomycin and 2000 AU ml$^{-1}$ crude peptide ST4SA. Colonies were selected at random and checked for production of peptide ST4SA and screened for plasmid content, as described before. A colony of conjugated cells of Ent. faecalis OGX1 which contained pST4SA was cultured and the cell-free supernatant was subjected to activity tests, as described before.

Detection of the Genetic Elements Encoding Peptide ST4SA and DNA Sequencing.

Total DNA was isolated. The DNA primers used to amplify the structural gene, transporter gene and immunity gene (listed below) by PCR, were designed based on partial sequences published for other antimicrobial peptides. Sequencing was performed with an ABI Pris™ BigDye™ Terminator Cycle Sequencing Ready Reaction kit on a ABI Prism™ 377 DNA Sequencer (PE Applied Biosystem, Foster City, USA). A database search was performed by using the BLASTN and BLASTX programs of the National Center for Biotechnology Information (NCBI), Bethesda, Md. 20894, USA.

```
Structural gene Primers:
SEQ. ID. NO. 3: SG-a:       TGAGAGAAGGTTTAAGTTTTGAAG
                            AA
                            (forward)
SEQ. ID. NO. 4: SG-b:       TCCACTGAAATCCATGAATGA
                            (reverse)

ABC transporter primers:
SEQ. ID. NO. 5: ABC 1-a:    TGATGGATTTCAGTGGAAGT
                            (forward)
SEQ. ID. NO. 6: ABC 1-b:    ATCTCTTCTCCGTTTAATCG
                            (reverse)

SEQ. ID. NO. 7: ABC2-a:     GTCATTGTTGTGGGGATTAT
                            (forward)
SEQ. ID. NO. 8: ABG2-b:     TCTAGATACGTATCAAGTCC
                            (reverse)

Immunity primers:
SEQ. ID. NO. 9: Immun-a:    TTCCTGATGAACAAGAACTC
                            (forward)
SEQ. ID. NO. 10: Immun-b:   GTCCCCACAACCAATAACTA
                            (reverse)
```

Production of Peptide ST4SA in Different Growth Media and at Different Initial Growth pH values An 18 h-old culture of strain ST4SA was inoculated (2%, v/v) into MRS broth, BHI broth and M17 broth (Merck, Darmstadt, Germany), respectively. Incubation was at 30° C. and 37° C., respectively, without agitation, for 28 h. Samples were taken every hour and examined for bacterial growth (OD at 600 nm), changes in culture pH, and antimicrobial activity (AU/ml) against *L. casei* LHS. The agar-spot test method was used as described before.

In a separate experiment, the effect of initial medium pH on the production of peptide ST4SA was determined. Volumes of 300 ml MRS broth were adjusted to pH 4.5, 5.0, 5.5, 6.0 and 6.5, respectively, with 6 M HCl or 6 M NaOH and then autoclaved (FIG. 9A). Each flask was inoculated with 2% (v/v) of an 18 h-old culture of strain ST4SA and incubated at 30° C. for 20 h without agitation. Changes in culture pH and production of peptide ST4SA, expressed as AU/ml, were determined every hour as described hereinbefore. All experiments were done in triplicate.

Effect of Medium Composition on the Production of Peptide ST4SA

Strain ST4SA was grown in 10 ml MRS broth for 18 h at 30° C., the cells harvested by centrifugation (8000×g, 10 min, 4° C.), and the pellet resuspended in 10 ml sterile peptone water. Four ml of this cell suspension was used to inoculate 200 ml of the following media: (a) MRS broth (De Man, Rogosa and Sharpe), without organic nutrients, supplemented with tryptone (20.0 g/l), meat extract (20.0 g/l), yeast extract (20.0 g/l), tryptone (12.5 g/l) plus meat extract (7.5 g/l), tryptone (12.5 g/l) plus yeast extract (7.5 g/l), meat extract (10.0 g/l) plus yeast extract (10.0 g/l), or a combination of tryptone (10.0 g/l), meat extract (5.0 g/l) and yeast extract (5.0 g/l), respectively; (b) MRS broth (Biolab), i.e. with 20.0 g/l glucose; (c) MRS broth (De Man, Rogosa and Sharpe) without glucose, supplemented with 20.0 g/l fructose, sucrose, lactose, mannose, and maltose, respectively; (d) MRS broth with 0.1-40.0 g/l fructose as sole carbon source; (e) MRS broth (De Man, Rogosa and Sharpe) with 2.0-50.0 g/l $K_2HPO_4$ or 2.0-50.0 g/l $KH_2PO_4$; and (f) MRS broth (De Man, Rogosa and Sharpe) supplemented with 0-50.0 g/l glycerol. In a separate experiment, the vitamins cyanocobalamin (Sigma, St. Louis, Mo.), L-ascorbic acid (BDH Chemicals Ltd, Poole, UK), thiamine (Sigma), DL-6,8-thioctic acid (Sigma) and Vitamin $K_1$ (Fluka Chemie AG, CH-9471 Buchs, Switzerland) were filter-sterilised and added to MRS broth at 1.0 mg/ml (final concentration). Incubation for all tests was at 30° C. for 20 h. Activity levels of peptide ST4SA were determined as described before. All experiments were done in triplicate.

Strain ST4SA was identified as a strain of the genus *Enterococcus*, based on morphology, as shown in FIG. 1, non-motility, absence of pigment formation, and PCR with genus-specific primers (FIG. 2) and species-specific primers (FIG. 3). Further identification to species level was by sugar fermentation patterns as shown in Table 1 and physiological characteristics as shown in Table 2 above.

Peptide ST4SA was inactivated by treatment with proteolytic enzymes (Proteinase K, pepsin, pronase, papain and trypsin), Triton X-114 and after 20 min at 121° C., as can be seen in Table 3. The peptide remained active after treatment for 90 min at 100° C. and when treated with Tween 20, Tween 80, urea, EDTA and Triton X-100 (Table 3). No activity was lost after incubation at pH values ranging from 2.0 to 12.0 (Table 3).

Peptide ST4SA inhibited a large number of Gram-positive and Gram-negative bacteria as shown in Table 4.

TABLE 4

| Organism | Temp.(° C.) | Medium, incubation | Peptide activity |
| --- | --- | --- | --- |
| *Acinetobacter baumanii* AB16 | 37 | BHI, aerobic | + |
| *Bacillus cereus* LMG 13569 | 37 | BHI, aerobic | + |
| *Clostridium tyrobutyricum* LMG 13571 | 30 | RCM, anaerobic | + |
| *Enterobacter cloacae*26 | 37 | BHI | + |
| *Enterococcus faecalis* LMG 13566, E77, E80, E90, E92, FA2, 20, 21 | 37 | MRS, aerobic | + |
| *Escherichia coli* EC1 | 37 | BHI | + |
| *Klebsiela pneumoniae* KP31 | 37 | BHI | + |
| *Lactobacillus acidophilus* LMG 13550 | 37 | MRS, anaerobic | − |
| *Lactobacillus bulgaricus* LMG 13551 | 37 | MRS, anaerobic | − |
| *Lactobacillus casei* LMG 13552 | 37 | MRS, anaerobic | − |
| *Lactobacillus curvatus* LMG 13553 | 30 | MRS, anaerobic | − |
| *Lactobacillus fermentum* LMG 13554 | 37 | MRS, anaerobic | − |
| *Lactobacillus helveticus* LMG 13555 | 42 | MRS, anaerobic | − |
| *Lactobacillus plantarum* LMG 13556 | 37 | MRS, anaerobic | − |
| *Lactobacillus reuteri* LMG 13557 | 37 | MRS, anaerobic | − |
| *Lactobacillus sakei* LMG 13558 | 30 | MRS, anaerobic | + |
| *Leuconostoc mesenteroides* subsp. *cremoris* LMG 13562 | 30 | MRS, anaerobic | − |

TABLE 4-continued

| Organism | Temp.(° C.) | Medium, incubation | Peptide activity |
|---|---|---|---|
| *Listeria innocua* LMG 13568 | 30 | BHI, aerobic | + |
| *Pediococcus pentosaceus* LMG 13560 | 30 | MRS, anaerobic | − |
| *Prop. acidipropionici* LMG 13572 | 32 | GYP, anaerobic | − |
| *Propionibacterium* sp. LMG 13574 | 32 | GYP, anaerobic | + |
| *Pseudomonas aeruginosa* 1, 7 | 37 | BHI, aerobic | + |
| *Staphylococcus aureus* 6, 13, 33-38 | 37 | BHI | + |
| *Staphylococcus carnosus* LMG 13567 | 37 | BHI, aerobic | + |
| *Streptococcus caprinus* TS1, TS2 | 37 | BHI, aerobic | + |
| *Streptococcus pneumoniae* 3, 4, 27, 29 | 37 | BHI, aerobic | + |
| *Streptococcus thermophilus* LMG 13565 | 42 | MRS, anaerobic | − |

Figure 5:
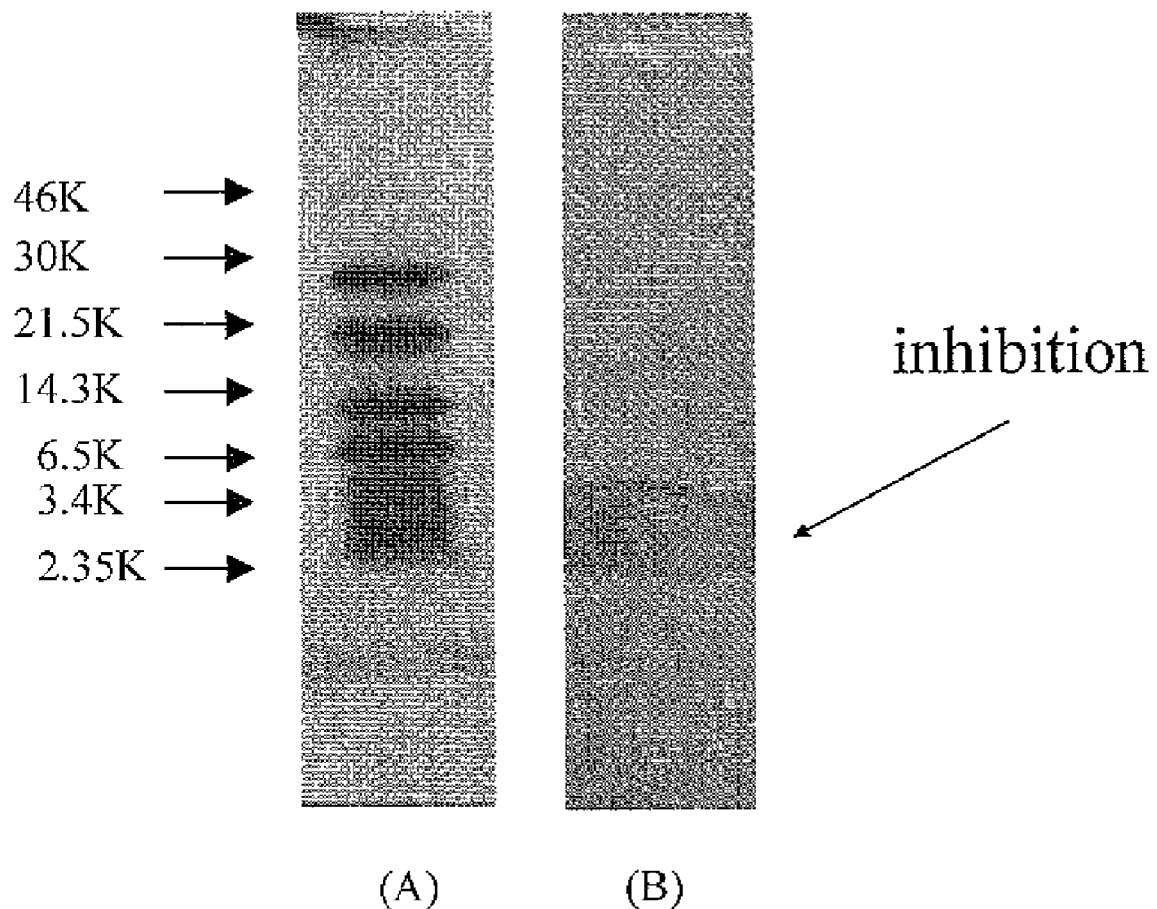
FIG. 5 is a photograph of a SDS-polyacrylamide gel showing the position of peptide ST4SA.

Peptide ST4SA was purified by gel filtration shown in FIG. 4 and is in the range of 3400 Da, as seen from FIGS. 4 and 5. The peptide had no cytotoxicity when tested on Vero cells as described hereinbefore.

Figure 6A:
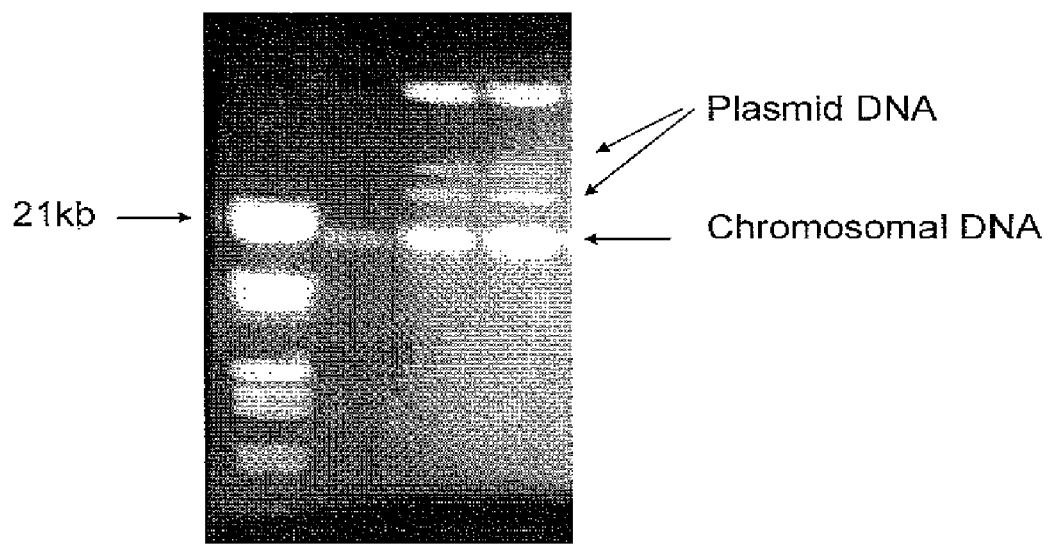
FIG. 6A is a photograph of an agarose gel showing the plasmid profile of *E. mundtii* ST4SA.
Figure 6B:
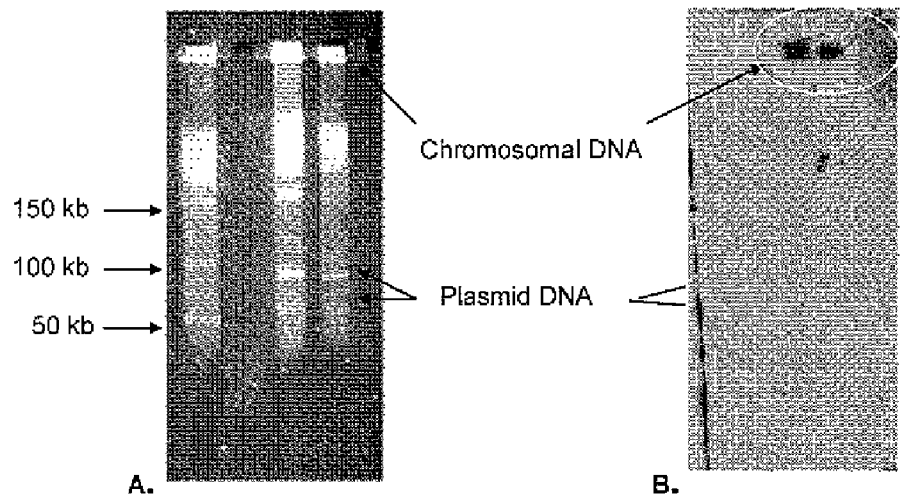
FIG. 6B is a Southern blot showing the location of the structural gene on the chromosome (genome) of strain ST4SA.

Strain ST4SA has two plasmids as shown in FIG. 6A. Curing the strain of these plasmids did not result in loss of antimicrobial activity. Probing of the chromosome and plasmid DNA with a DNA fragment encoding the structural gene showed clear hybridization with the chromosome (genome) (FIG. 6B). This proved that the structural gene encoding peptide ST4SA is located on the genome. Furthermore, conjugation of these plasmids to *E. faecalis* (not shown) did not convert the strain to a peptide ST4SA producer, confirming that the genes encoding peptide ST4 production are located on the genome of strain ST4SA.

Figure 7:
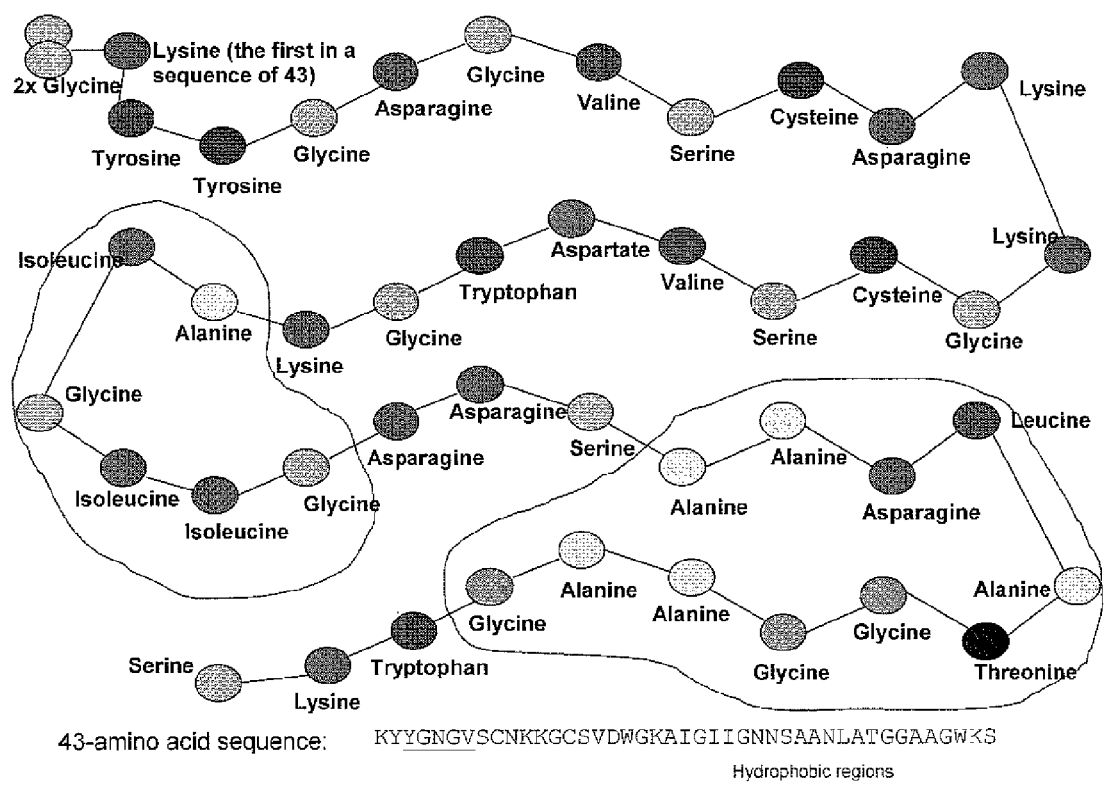
FIG. 7 is a diagrammatic representation of the amino acid sequence of *E. mundtii* peptide ST4SA.

The sequence of peptide ST4SA is indicated in FIG. 7 and the sequence listing and is indexed as SEQ. ID. NO. 12 for the purposes of this invention. The sequence of the transporter and immunity peptides are indexed as SEQ. ID. NOs 14 and 16, respectively, for the purposes of this invention.

The DNA sequences of the structural, transporter and immunity genes are indicated in FIG. 8 and the sequence listing, and are indexed as SEQ. ID. NOs 11, 13 and 15, respectively, for the purposes of this specification.

Production of peptide ST4SA in different growth media is indicated in FIGS. 9A and 9B. The influence of initial growth pH on peptide ST4SA production is indicated in FIG. 9A. From these results, it is evident that peptide ST4SA is optimally produced in MRS broth at an initial pH of 6.0 and 6.5, and is stimulated by the presence of 10-20 g/l $K_2HPO_4$, 15.0-20.0 g/l fructose, or in the presence of vitamins C, $B_1$ and DL-6,8-thioctic acid.

Production of peptide ST4SA is indicated in FIG. 10. Maximal production was recorded after 14 h of growth.

Figure 11:
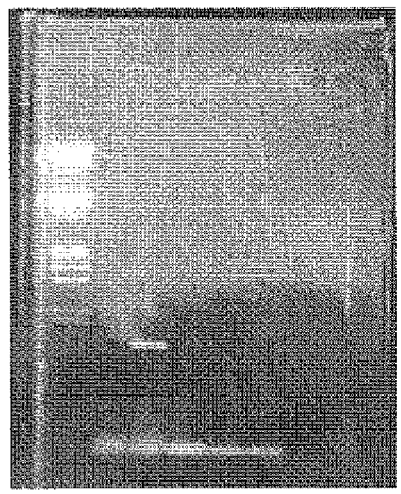
FIG. 11 is a photograph of an agarose gel showing a DNA fragment which may contain the putative adhesion gene.

A DNA fragment containing an adhesion/immunity gene is indicated in FIG. 11, and is indexed as SEQ. ID. NO. 15 for the purposes of this specification.

*Enterococcus mundtii* ST4SA produces a broad-spectrum antimicrobial peptide (peptide ST4SA) with activity against a number of pathogens. The structural gene encoding the leader peptide and propeptide (collectively known as the prepeptide) is located on the genome of strain ST4SA (see FIG. 6B). Only one such gene structure was detected, suggesting that only one peptide is responsible for the broad spectrum of antimicrobial activity. Efforts were made to cure strain ST4SA from its 50 kb and 100 kb plasmids (FIG. 1), but they failed. This suggests that the plasmid may play a major role in rendering immunity to peptide ST4SA, or harbours genes important in key metabolic reactions.

Further evidence that ST4SA is a strain of *Enterococcus mundtii* was obtained by species-specific PCR (polymerase chain reaction) with primers designed from conserved regions on 16S rDNA using:

SEQ. ID. NO. 1: Forward primer: AACGAGCGCAACCC;

SEQ. ID. NO. 2 Reverse primer: GACGGGCGGTGTGTAC.

A 306 base-pair fragment was amplified (shown in FIG. 3). Sequencing of the DNA fragment yielded 98% homology with conserved 16S rDNA fragments in GenBank.

The structural gene (encoding the propeptide ST4SA), the transporter genes and the immunity gene have been sequenced and their respective amino acid sequences translated from the DNA sequences (FIG. 8).

Figure 12:
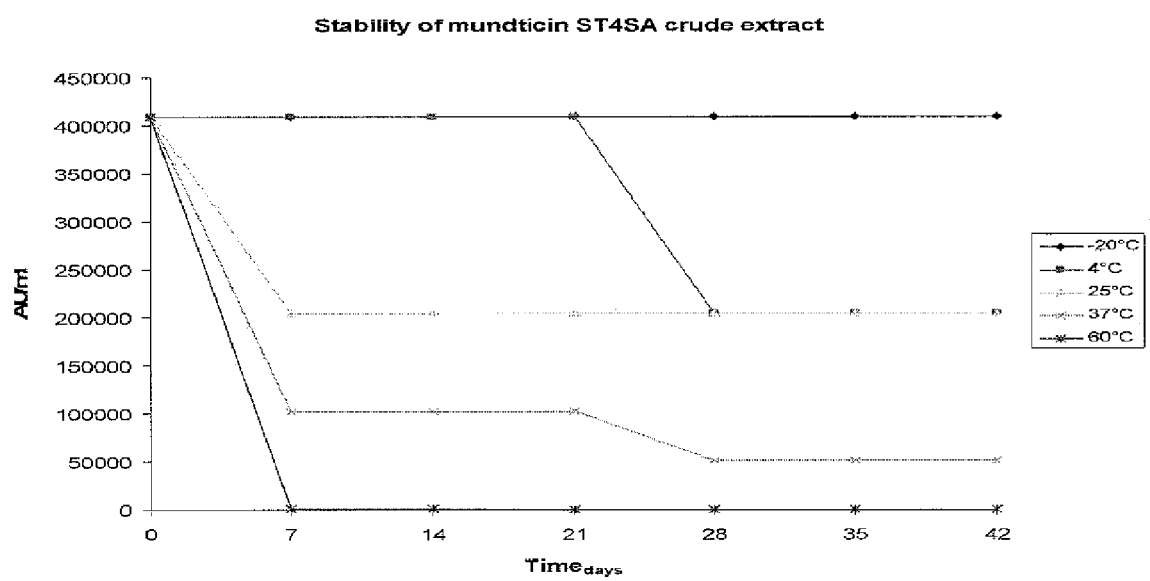
FIG. 12 is a graph showing the stability of peptide ST4SA (crude extract suspended in sterile distilled water) at different temperatures.

The stability of peptide ST4SA, suspended in sterile distilled water, was tested at temperatures ranging from −20° C. to 60° C. over 42 days (FIG. 12). The peptide remained stable at −20° C. for 42 days and for three weeks at 4° C. Stability decreased after one week at 37° C. Peptide ST4SA in powder form did, however, remain stable for 6 months at room temperature (25° C.). Peptide ST4SA will be produced in powder form and marketed as such. Once dissolved in sterile distilled water, peptide ST4SA may be kept for three weeks at 4° C. (see FIG. 12).

Figure 13:
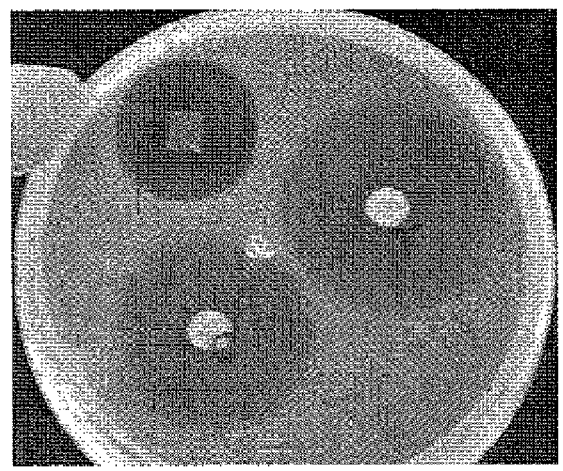
FIG. 13 is a photograph of inhibition zones recorded against *Pseudomonas* sp. on an agar plate.

The activity of peptide ST4SA on paper disks is listed in Table 5. Comparison of activity with antibiotics is listed in Table 6. Activity was tested against a *Pseudomonas* sp. isolated from infected middle-ear fluid. Images of the inhibition zones are shown in FIG. 13.

TABLE 5

Activity of peptide ST4SA on paper disks.

|  | Peptide ST4SA (AU/ml) |
|---|---|
| Freeze dried (AU/ml) | 409600 |
| Paper disk (2 cm × 2 cm; 700 µl) | 286720 |
| Paper disk (0.6 cm diameter) | 20263 |

TABLE 6

Comparison of the activity of peptide ST4SA to commonly used antibiotics.

| Antibiotic | Diameter of inhibition zones (mm) |
|---|---|
| Ampicillin (10 µg) | 24 |
| Bacitracin (10 units) | 10 |
| Chloramphenicol (30 µg) | 28 |
| Erythromycin (15 µg) | No zone |
| Tetracycline (30 µg) | 35 |
| Peptide ST4SA | 25 |

Figure 14:
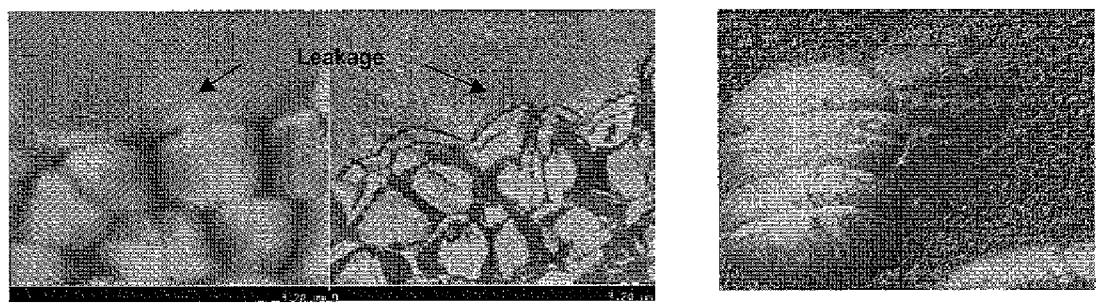
FIG. 14 is a photograph of *Streptococcus pneumoniae* treated with peptide ST4SA (409 600 AU/ml) and leakage of the cytoplasm is indicated by the arrows.
Figure 15:
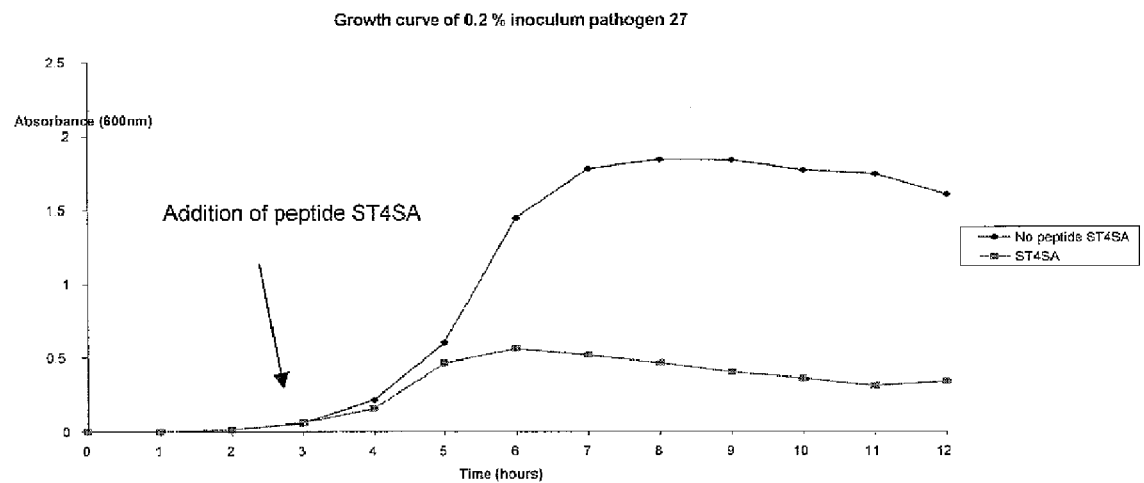
FIG. 15 is a graph showing the growth inhibition of *Streptococcus pneumoniae* (pathogen 27)
Figure 16:
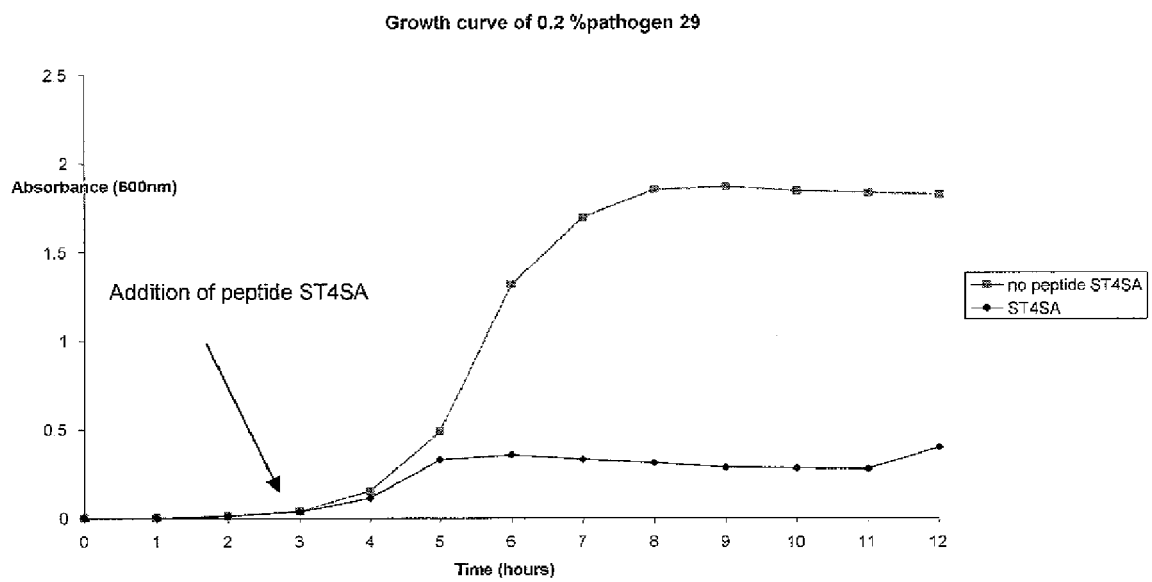
FIG. 16 is a graph showing the growth inhibition of *Streptococcus pneumoniae* (pathogen 29)
Figure 17:
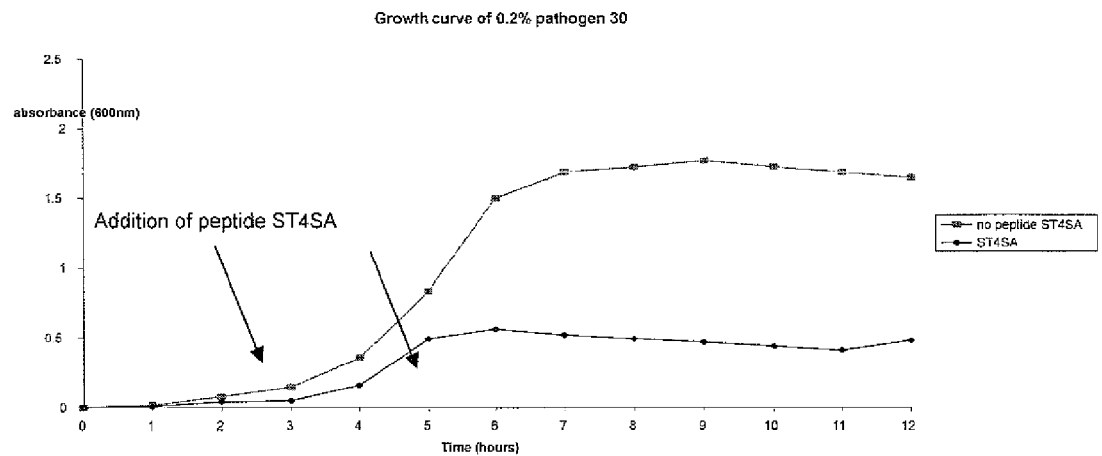
FIG. 17 is a graph showing the growth inhibition of *Klebsiella pneumoniae* (pathogen 30)
Figure 18:
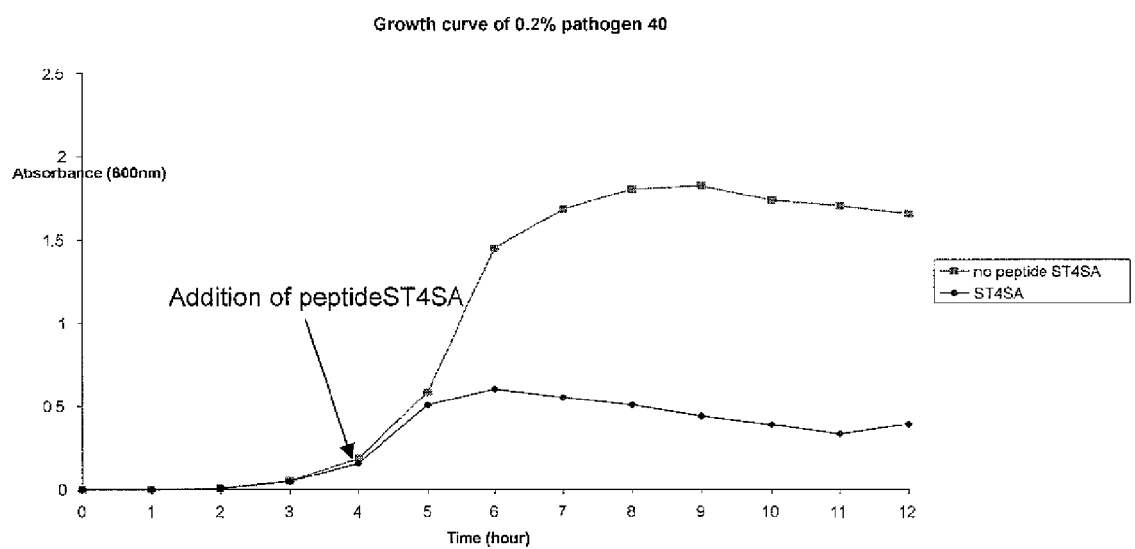
FIG. 18 is a graph showing the growth inhibition of middle ear isolate (pathogen 40)
Figure 19:
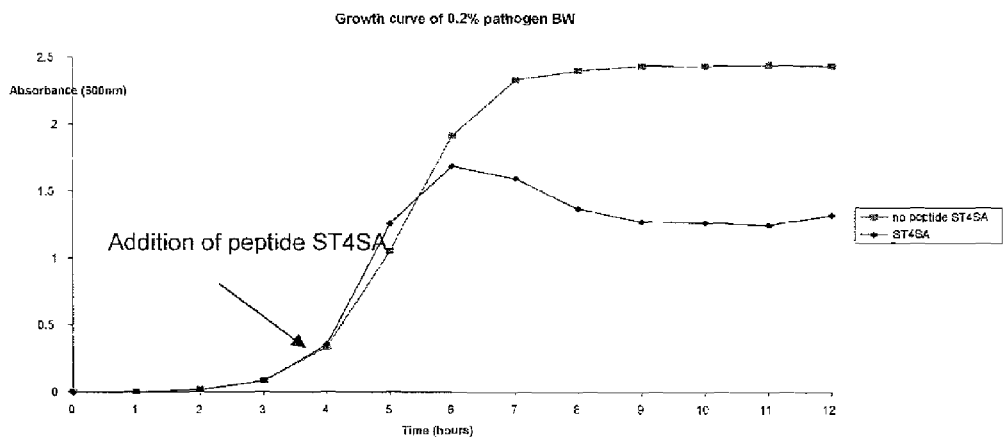
FIG. 19 is a graph showing the growth inhibition of middle ear isolate (pathogen BW)
Figure 20:
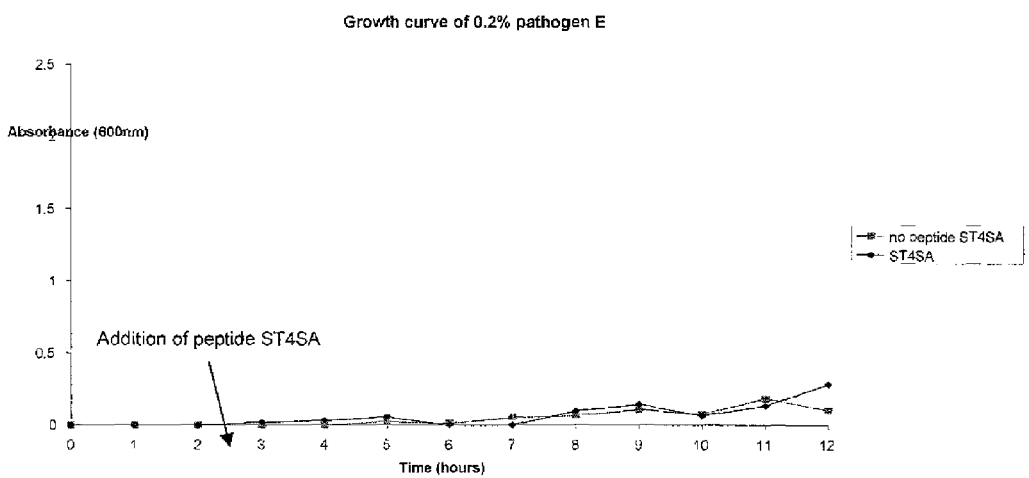
FIG. 20 is a graph showing the growth inhibition of middle ear isolate (pathogen E)
Figure 21:
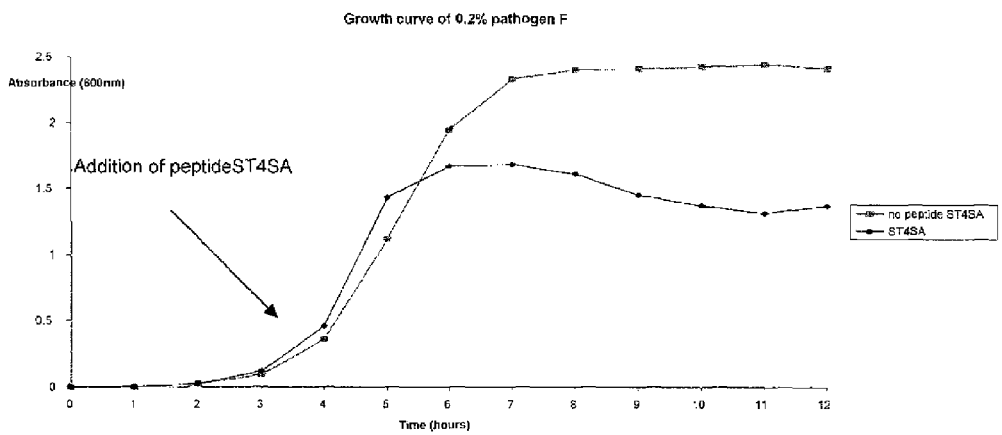
FIG. 21 is a graph showing the growth inhibition of middle ear isolate (pathogen F)
Figure 22:
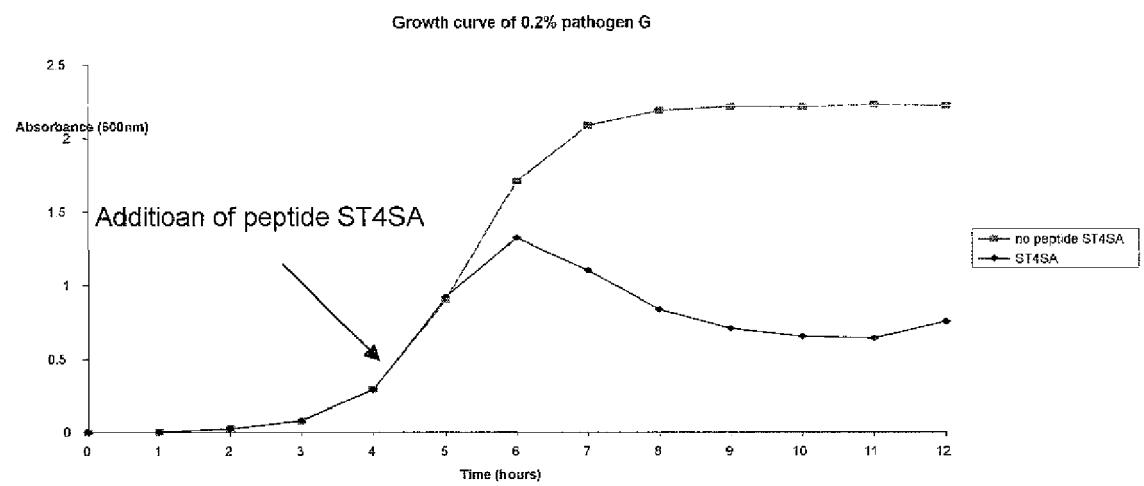
FIG. 22 is a graph showing the growth inhibition of middle ear isolate (pathogen GW)
Figure 23:
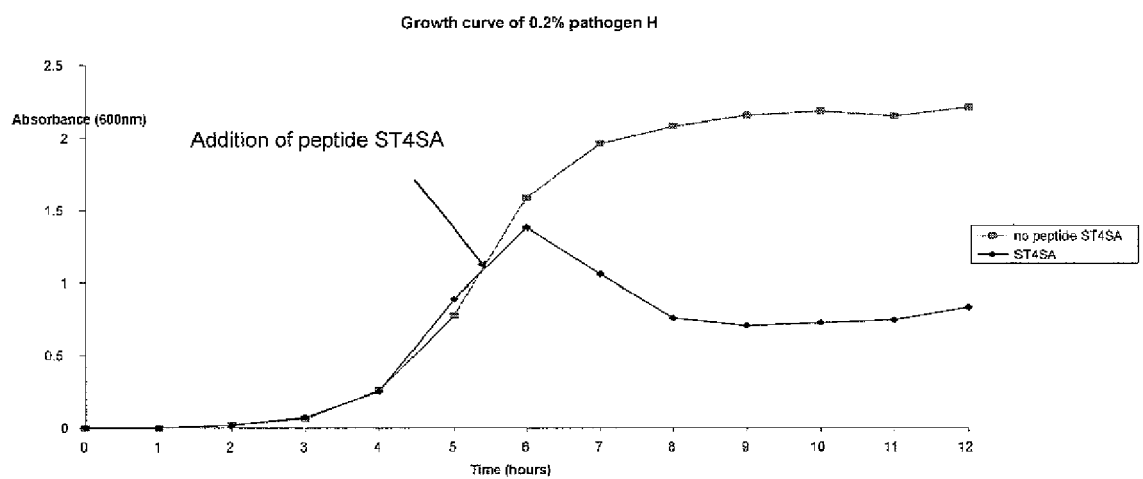
FIG. 23 is a graph showing growth inhibition of middle ear isolate (pathogen HW)

Binding of peptide ST4SA to target cells is important to ensure penetration of the peptide. The ability of peptide ST4SA to adhere to pathogens was studied and the results were expressed as a percentage binding to the pathogens (Table 7). Concluded from these results, at least 75% of peptide ST4SA binds to the pathogens tested. Adhesion of peptide ST4SA to the target cell leads to penetration and disruption of the cell membrane (FIG. 14).

TABLE 7

Adhesion of peptide ST4SA to pathogens.

% Binding of peptide ST4SA to the target cell (pathogen)

| Pathogen | Peptide ST4SA at 6 400 AU/mL | | | | | | Peptide ST4SA at 204 800 AU/ml | | | | | |
|---|---|---|---|---|---|---|---|---|---|---|---|---|
| | 0 | 50 | 75 | 88 | 94 | 100 | 0 | 50 | 75 | 88 | 94 | 100 |
| *Streptococcus pneumoniae* | | | | | | | | | | | | |
| 27 | | | + | | | | | | + | | | |
| 29 | | | + | | | | | | + | | | |
| D | | + | | | | | | | + | | | |
| *Streptococcus pyogenes* | | | | | | | | | | | | |
| 20 | | | | + | | | | | | + | | |
| 21 | | | | + | | | | | | + | | |
| *Pseudomonas auringinosa* | | | | | | | | | | | | |
| E | | | | + | | | | | | + | | |
| *Klebsiella pneumoniae* | | | | | | | | | | | | |
| 30 | | | + | | | | | | + | | | |
| Middle ear isolates (unknown) | | | | | | | | | | | | |
| 13 | | | + | | | | | | + | | | |
| 17 | | | + | | | | | | + | | | |
| 25 | | | | | + | | | | | | + | |
| 40 | | | + | | | | | | | | + | |
| BW | | | + | | | | | | + | | | |
| CW | | + | | | | | | | + | | | |
| DW | | | | | | | | | | | | |
| F | | | + | | | | | | + | | | |
| HW | | + | | | | | | | + | | | |
| I | + | | | | | | | | + | | | |
| J | | + | | | | | | | + | | | |
| GW | | | | + | | | | | + | | | |
| K | | | + | | | | | | | | + | |
| L | | + | | | | | | | + | | | |
| M | | + | | | | | | | + | | | |

Further evidence of cell membrane damage and leakage of cellular constituents was obtained by testing for extracellular DNA and extracellular β-galactosidase activity. The results are shown in Tables 8 and 9, respectively. The results indicate that DNA and α-galactosidase leaked from cells damaged by peptide ST4SA. α-galactosidase leakage was not recorded for all pathogens, due to the fact that not all species have high intracellular levels of this enzyme.

TABLE 8

Extracellular DNA recorded after treatment of pathogens with peptide ST4SA.

| Pathogen | DNA-leakage (O.D. readings at 260 nm) |
|---|---|
| *Streptococcus pneumoniae* | |
| 27 | 1.670 |
| 29 | 1.182 |
| D | 1.160 |
| *Streptococcus pyogenes* | |
| 20 | 0.930 |
| *Pseudomonas auringinosa* | |
| E | 0.187 |
| *Staphylococcus aureus* | |
| 36 | 0.892 |
| *Klebsiella pneumoniae* | |
| 30 | 1.01 |
| Middle ear isolates (unknown) | |
| 40 | 0.801 |
| BW | 1.186 |
| DW | 1.153 |
| F | 1.428 |
| HW | 1.559 |
| GW | 0.751 |
| K | 0.455 |
| L | 0.592 |
| M | 0.326 |
| Control | |
| *Enterococcus* spp. HKLHS | 1.395 |

TABLE 9

| Pathogen | β-galactosidase recorded at $OD_{420}$ |
|---|---|
| *Streptococcus pneumoniae* | |
| 27 | No leakage |
| 29 | No leakage |
| D | No leakage |
| *Streptococcus pyogenes* | |
| 20 | No leakage |
| *Staphylococcus aureus* | |
| 36 | No leakage |
| *Klebsiella pneumoniae* | |
| 30 | No leakage |
| Middle ear isolates (unknown) | |
| 40 | |
| BW | 0.370 |
| DW | 0.293 |
| F | 0.318 |
| HW | 0.235 |
| GW | 0.373 |
| K | No leakage |
| L | No leakage |
| M | No leakage |
| Control | |
| *Enterococcus* spp. HKLHS | No leakage |

Cell lysis of different pathogens after treatment with peptide ST4SA are shown in FIGS. 15 to 23. A 0.2% (v/v) inoculum of an overnight pathogen was inoculated into BHI broth. Peptide ST4SA was added to each pathogen at mid-exponential phase. From the results presented herein (FIGS.

15 to 23), it is clear that peptide ST4SA acted in a bactericidal manner against most pathogens.

Figure 24:
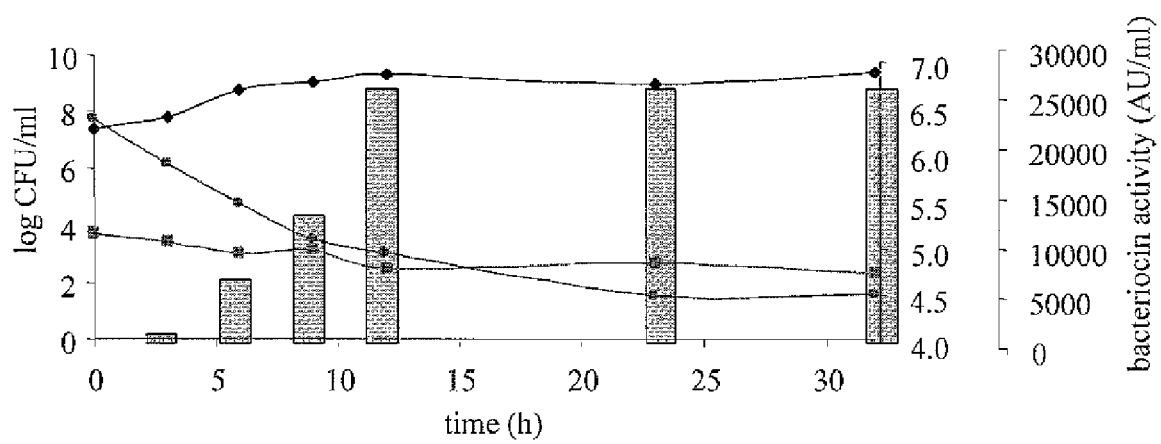
FIG. 24 is a graph showing growth of strain ST4SA in the presence of *Listeria innocua* LMG 13568 and production of peptide ST4SA. Symbols: -♦-=growth of strain ST4SA in the presence of *L. innocua* LMG 13568, -■-=growth inhibition of *L. innocua* LMG 13568; -●-=changes in pH, ▮ =production of peptide ST4SA.

Production of peptide ST4SA was studied in the presence of *Listeria innocua* (FIG. 24). Based on these results, *L. innocua* stimulated strain ST4SA to produce peptide ST4SA, during which *L. innocua* was inhibited.

Enterococcus Mundtii ST4SA as a Probiotic

Figure 25:
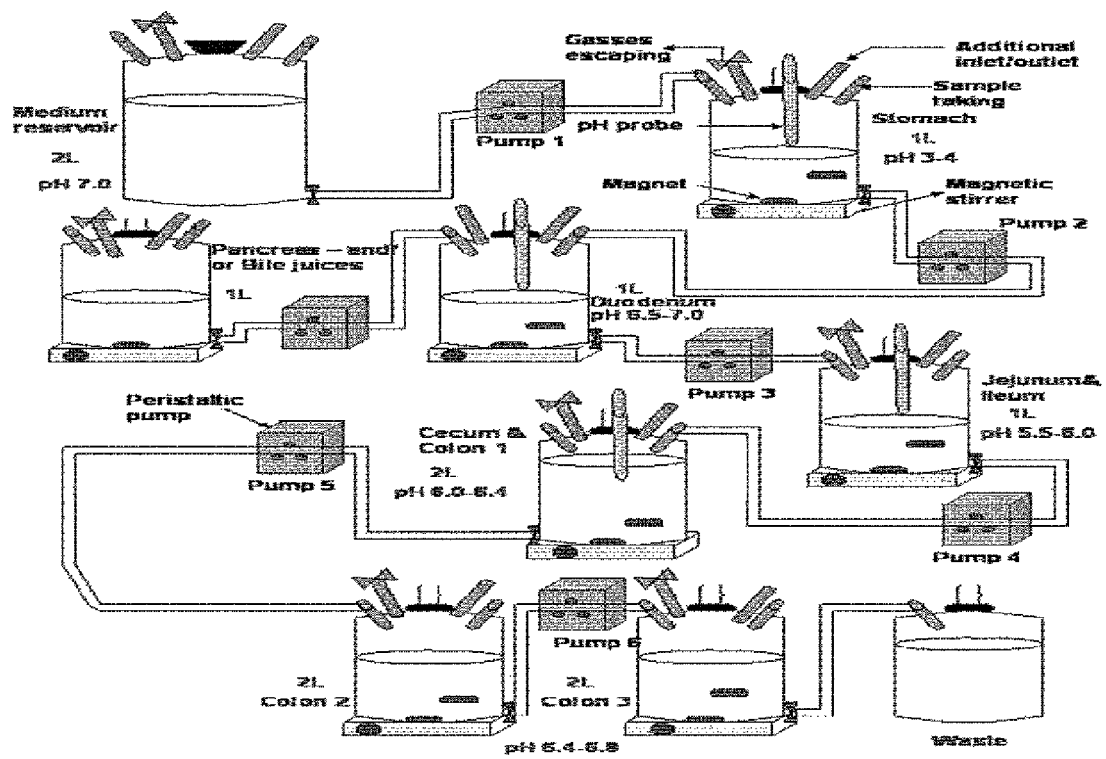
FIG. 25 is a schematic presentation of a gastro-intestinal model (GIM) developed for evaluation of probiotic strain ST4SA.

The survival of *Enterococcus mundtii* ST4SA was evaluated in a computerized gastro-intestinal model (GIM, shown in FIG. 25).

The first vessel in the GIM simulates the stomach, the second vessel the duodenum, vessel number three the jejunum and ileum, and vessel four the colon. Flow of the nutrients was regulated by dedicated software. The pH in the different sections of the GIM was regulated by the peristaltic addition of sterile 1N HCl or 1N NaOH. Each section was fitted with a highly sensitive pH probe, linked to a control unit and computer. The flow rate of nutrients through the GIM was adjusted according to an infant's intestinal tract. Conditions simulating a short digestive tract were chosen to allow greater fluctuation and thus increased stress onto the probiotic. Four infant formulas (Lactogen2, NAN Pelargon, ALL110 and Alfare) were evaluated. Dosage with the probiotic bacterium (ST4SA) was according to prescription, i.e. $10^8$ viable cells (cfu) per ml. The probiotic cells were suspended in saliva. The pancreatic-bile solution contained $NaHCO_3$, pancreatin and oxgall, dissolved in distilled water. The conditions used in the GIM were as summarized in Tables 10 and 11.

TABLE 10

| Time (min.) | pH | Growth medium | Pancreatic-bile solution |
|---|---|---|---|
| 0-4 | | Nutrients pumped into stomach vessel. Dosage with strain ST4SA ($10^8$ cfu/ml) | |
| 4-44 | 5.2 | Incubation in stomach | |
| 44-64 | 4.9 | | |
| 64-108 | 4.5 | | |
| 108-128 | 4.1 | | |
| 128-154 | 3.7 | | |
| 154-156 | | | Pancreatic-bile solution pumped into the duodenum |
| 154-158 | | Stomach contents pumped to duodenum | |
| 158-274 | 6.5 | Incubation in duodenum | |
| 274-280 | | Duodenum contents pumped to jejunum | |
| 280-394 | 6.5 | Incubation in jejunum | |
| 394-401 | | Jejunum contents pumped to ileum | |
| 401-520 | 6.0 | Incubation in ileum | |

TABLE 11

| GIM section | Cfu[a]/ml in NAN Pelargon | Bacteriocin activity (>25 600 AU[b]/ml) | Cfu/ml in MRS broth | Bacteriocin activity (>25 600 AU/ml) |
|---|---|---|---|---|
| Inoculum | $10 \times 10^8$ | + | $6.0 \times 10^7$ | + |
| Stomach | $1.2 \times 10^7$ | + | $3.7 \times 10^7$ | + |
| Duodenum | $2.5 \times 10^6$ | + | $1.0 \times 10^8$ | + |
| Jejunum | $1.0 \times 10^7$ | + | $1.3 \times 10^8$ | + |
| Ileum | $5.0 \times 10^7$ | + | $1.0 \times 10^8$ | + |

[a]Cfu = colony froming units (i.e. number of viable cells)
[b]AU = arbitrary units (thus reflecting antimicrobial activity)

Survival of strain ST4SA against a pathogen was tested by infecting the GIM with *Listeria monocytogenes*. The survival of strain ST4SA and its ability to produce the antimicrobial peptide ST4SA in the GIM was monitored (results shown in Table 12).

TABLE 12

| Antibiotics | ST4 |
|---|---|
| Ampicillin | +++ |
| Bacitracin | ++ |
| Cephazolin | + |
| Chloramphenicol | +++ |
| Ciprofloxzcin | +++ |
| Cd. Sulphonamides | − |
| Cloxacillin | − |
| Erythromycin | +++ |
| Metronidazole | − |
| Methicillin | − |
| Neomycin | − |
| Novobiocin | +++ |
| Nystatin | − |
| Oflaxacin | ++ |
| Oxacillin | − |
| Rifampicin | +++ |
| Tetracyclin | +++ |
| Streptomycin | − |
| Vancomycin | ++ |
| Penicillin | +++ |

Key:
− = no zones (resistance to antibiotic);
+ = inhibition zone, diameter 1 to 11 mm;
++ = inhibition zone, diameter 12 to 16 mm;
+++ = inhibition zone, diameter larger than 17 mm.

As may be concluded from the results presented in Table 12, strain ST4SA survived in all sections of the intestinal tract. Antimicrobial peptide production was in excess of 25 600 AU (arbitrary units) per ml in all sections of the intestinal tract. Growth in NAN Palargon was slightly less optimal than in MRS. However, in both experiments the cell numbers did not decrease by more than one logarithmic cycle (see Table 13).

TABLE 13

| Antibiotic (mg) | Number of viable cells of strain ST4SA |
|---|---|
| Control | $1 \times 10^8$ |
| TMP-SMX 20/100 | $7 \times 10^4$ |
| TMP-SMX 40/200 | $8 \times 10^4$ |
| TMP-SMX 60/300 | $8 \times 10^4$ |
| TMP-SMX 80/400 | $1.8 \times 10^4$ |
| Metronidazole 50 | $1.3 \times 10^4$ |
| Metronidazole 100 | $6 \times 10^4$ |
| Metronidazole 200 | $3 \times 10^4$ |

Resistance of strain ST4SA to various antibiotics has been tested according to standard procedures (antibiotic discs, Oxoid). Concluded from these results, strain ST4SA is resistant to sulphonamides, cloxacillin, metronidazole, methicillin, neomycin, nystatin, oxacillin and streptomycin (Table 13).

Children with HIV/AIDS are treated with Trimethoprim-sulfamethoxazole (TMP-SMX) and/or Metronidazole to prevent diarrhea. NAN Palargon was supplemented with different concentrations of the latter antibiotics and the effect on strain ST4SA determined after 18 h at optimal growth temperature (37° C.).

As may be concluded from the results presented in Table 4, TMP-SMX and Metronidazole decreased the cell numbers of strain ST4SA with four log cycles. However, increased concentrations had no drastic effect on viability.

The Incidence of Virulence Factors in ST4SA

To develop strain ST4SA as a probiotic, it is important to know if there are any virulence factors associated therewith. Primers have been designed for the genes encoding the following virulence factors: Vancomycin resistance (VanA/

VanB); production of gelatinase (Gel); aggregation substance (AS); adhesin of collagen from enterococci (Ace), *enterococcus* surface protein (Esp); haemolysin/bacteriocin (Cyl) and non-cytolysin beta hemolysin genes. The DNA of strain ST4SA amplified with the latter primers indicated that the strain does not have the genes encoding vancomycin resistance, gelatinase activity, an aggregation substance, and collagen adhesion. Based on present results, strain ST4SA is not pathogenic and should not cause allergic reactions when ingested.

As peptide ST4SA has a broad spectrum of antimicrobial activity, acting against a number of Gram-positive and Gram negative bacteria, the mode of action of peptide ST4SA appears to be different from other antimicrobial peptides thus far described for lactic acid bacteria. In addition, the site of recognition on the cell walls of sensitive cells may differ from the usual Lipid II anchor site used by other peptides of which the Applicant is aware (FIG. 26).

Figure 26:
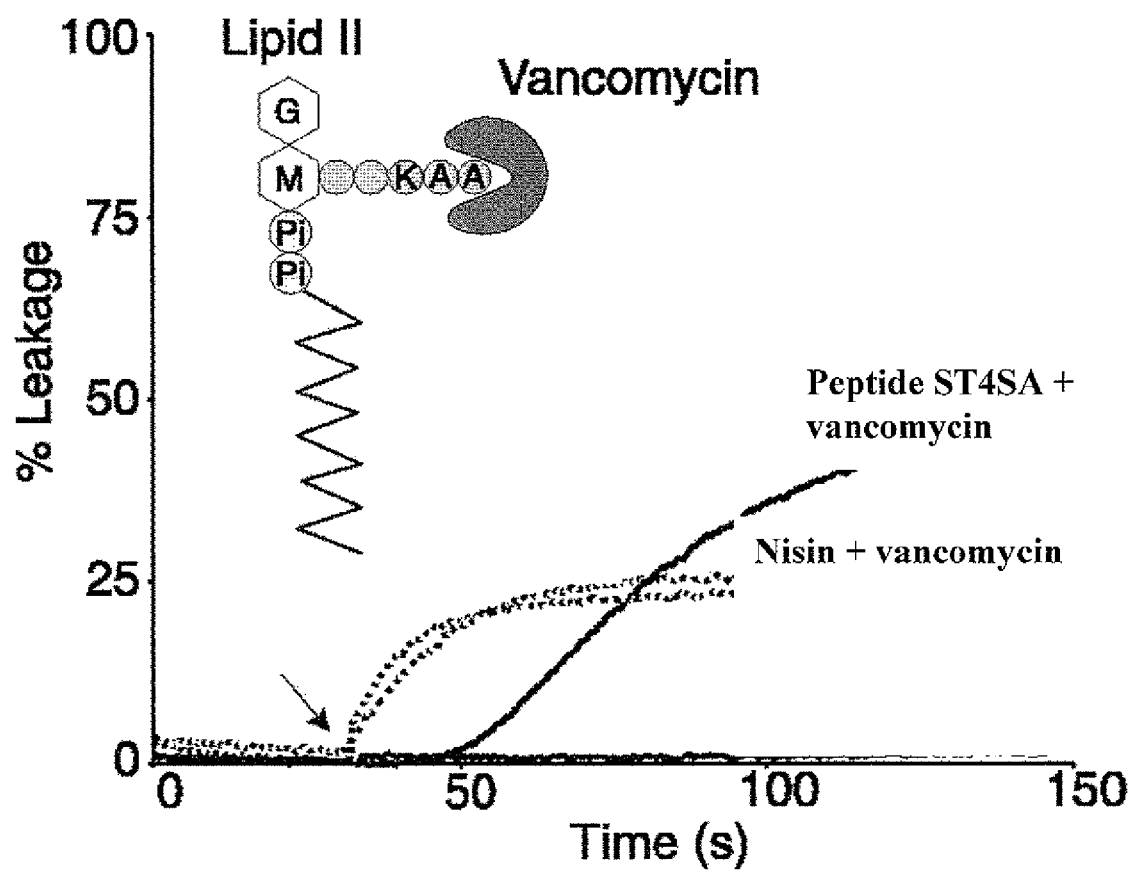
FIG. 26 is a schematic presentation showing blocking of the Lipid II target site with vancomycin and its affect on the mode of action (antimicrobial activity) of peptide ST4SA. % Leakage refers to cytoplasmic leakage, as recorded by increased DNA and β-galactosidase activity levels.

To test this hypothesis, the Lipid II target site of *Lactobacillus sakei* DSM 20017 (sensitive to peptide ST 4SA) was blocked with vancomycin (see schematic presentation, FIG. 26). Vancomycin adheres to the amino acid side chain of the Lipid II molecule, which would, theoretically, prevent peptide ST4SA from binding to the same site (that is if Lipid II acts as receptor). Treatment of target cells (*L. sakei* DSM 20017) with a combination of vancomycin and peptide ST4SA, however, resulted in growth inhibition (leakage of cytoplasm; see FIG. 26), suggesting that target sites other than Lipid II are acting as receptors for peptide ST4SA. The fact that peptide ST4SA binds to more than one anchoring site on the sensitive cell may explain why it has such a broad spectrum of antimicrobial activity (inhibitory to Gram-positive and Gram-negative bacteria). The Applicant is aware of the fact that Nisin (a antibiotic) binds to Lipid II, as shown in FIG. 26 in which treatment of *L. sakei* DSM 20017 with vancomycin prevented the binding of Nisin to the Lipid II target site.

Figure 27:
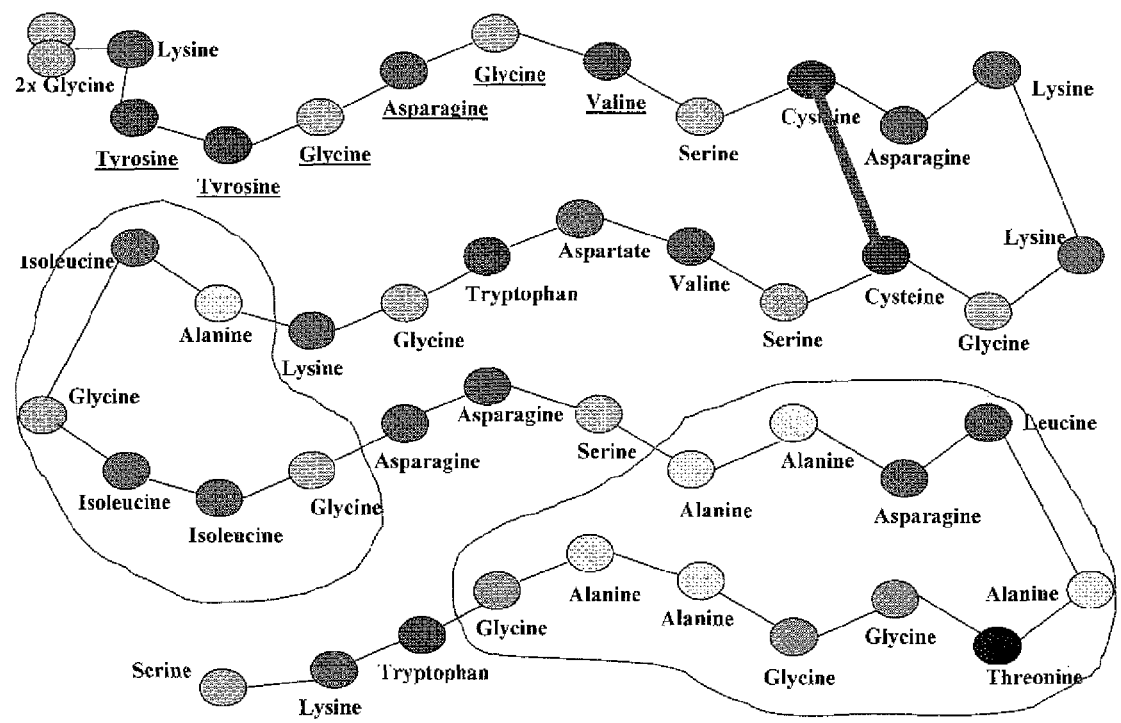
FIG. 27 is a schematic representation of a disulfide bridge that was introduced into the peptide that covalently linked amino acids 9 (cysteine) and 14 (cysteine)

Peptide ST4SA has two hydrophobic regions (FIG. 27) which can intercalate with phospholipid-rich cell membranes after it has formed a reaction with the receptor site on the cell wall. The area between the two hydrophobic regions, more specifically between amino acid 29 (serine) and amino acid 30 (alanine) (FIG. 27) is more flexible than the rest of the structure and may act as a hinge area, which would allow the C-terminal half of the peptide to bend and incorporate itself into the phospholipid-rich cell membrane. To test this hypothesis, the two sections of peptide ST4SA (FIG. 27) were synthesized (listed hereinafter as Fragment 1 and Fragment 2), based on the amino acid sequence deduced from the DNA sequence of the structural gene.

As shown below, Fragment 1 consisted of the first 29 amino acids (from lysine to serine), just before the hinge area (viz. between the serine at position 29 and alanine at position 30). A disulfide bridge was introduced (connecting line, shown below) that covalently linked amino acids 9 (cysteine) and 14 (cysteine), also shown below in the full length peptide sequence:

(SEQ ID NO: 17)

KYYGNGVS<u>C</u>NKKG<u>C</u>SVDWGKAIGIIGNNS.

The disulfide bridge served to stabilize the structure of the peptide. Fragment 1 contained the first hydrophobic region, indicated by the encircled region (six amino acids from position 21 to 26, viz. AIGIIG). This part of the molecule recognizes the receptor on the cell wall of the target (sensitive) organism.

Fragment 2 comprised the last 13 C-terminal amino acids in the second hydrophobic loop downstream of the hinge area, plus the preceding 11 amino acids just before the hinge area (between serine and alanine):

(SEQ ID NO: 18)
Fragment 2:      KAIGIIGNNSAANLATGGAAGWKS

Treatment of sensitive cells with these two fragments of peptide ST4SA indicated that both fragments (sections) of the molecule are needed for antimicrobial activity. It would thus seem that disruption of the cellular membrane is only possible once the N-terminal is anchored to the receptor on the cell surface.

Binding of Peptide ST4SA to Polyethylene (PE)

Binding of peptide ST4SA to polyethylene (PE) was tested. PE film was cut into sections of 5×5 cm and soaked for 1 h in a solution of 60% isopropanol and peptide ST4SA (activity level: 102 400 AU/ml). The PE sections were air-dried (20 min at 60° C.) and assayed for antimicrobial activity by using the standard agar diffusion method. The plates, seeded with *L. sakei* DSM 20017, were incubated for 24 h at 30° C. and examined for zones of growth inhibition.

Peptide ST4SA adsorbed to PE within 60 seconds to produce a film with high antimicrobial activity (large inhibition zones surrounding the PE section). The strength of binding was determined by soaking the peptide-coated PE film in SDS-buffer, followed by electro-eluting peptide ST4SA from the film with a current of 30 mA for 2 h (room temperature, i.e. ca. 25° C.). Samples were taken at regular time intervals and tested for antimicrobial activity. Protein concentrations were determined by using the Bradford method. Electro-eluted film was tested for antimicrobial activity by using the agar diffusion method as before.

Peptide ST4SA adhered strongly, and it would seem irreversibly, to the PE film. Release of peptide ST4SA from the surface of PE was only possible after 1 h with a current of 30 mA. In a challenge study with red meat as model, surface (PE)-bound peptide ST4SA prevented the growth of pathogenic bacteria (*Listeria, Bacillus* and *Staphylococcus*). This suggests that peptide ST4SA is usable in wound dressings to prevent or reduce microbial infections and also finds uses in other medical or aseptic applications such as, for example, implants, ear grommets, catheters, ostomy tubes and pouches, stents, suture material, hygiene products such as feminine hygiene products, contact lenses, contact lens rinsing solutions. The encapsulation of the antimicrobial peptide in the polymer leads to a slow release of the antimicrobial peptide and an extended period of treatment of a microbial infection. Furthermore, strong adherence of peptide ST4SA to PE shows that it acts as a slow-release antimicrobial agent.

Peptide ST4SA binds to more than one receptor site on a microbial cell and is typical of what one would expect from a broad-spectrum antimicrobial agent. The first section of peptide ST4SA (in front of the hinge area) binds to the receptor. The second part (downstream of the hinge area) has a bigger hydrophobic region and intercalates into the cell membrane and distorts the permeability, leading to cell death (visualized by DNA and enzyme leakage). Peptide ST4SA binds to PE in a stable and slow-release fashion and is suited for incorporation into wound dressings.

Development of *Enterococcus mundtii* ST4SA into a Probiotic

The survival of *Enterococcus mundtii* ST4SA was evaluated in a computerized gastro-intestinal model as shown. This phase comprised further in vitro and in vivo evaluation of strain ST4SA as a probiotic. Adhesion to mucus and epithelial cells were studied in vitro with human cell lines. In vivo studies were performed in rats.

The human intestinal cell lines used in the study were from the human colon adenocarcinoma and included Caco-2 cell lines, HT-29 and HT29-MTX (mucus-secreting cells). The cell-lines express morphological and functional differentiation when grown under standard culture conditions and show characteristics of mature enterocytes, which include polarization, a functional brush order and apical intestinal hydrolases.

Adherence of strain ST4SA to host cells is influenced by cell surface carbohydrates, the Efa A protein, the Ace (adhesin of collagen from enterococci) protein and aggregation substance (AS), related to pathogenicity. AS is an adhesin which mediates the formation of cell clumps that allows the highly efficient transfer of the sex pheromone plasmid on which AS is encoded.

In this study, strain ST4SA was screened for virulence traits, bile salt hydrolase (BSH) activity, and the ability to adhere to the human enterocyte-like cell line Caco-2, competitive exclusion while adhering to the Caco-2 cell line, and in the in vitro gastro-intestinal (GIT) model. In addition, cell surface hydrophobicity of ST4SA was determined.

Virulence Factors

The presence of virulence factors, viz. vancomycin resistance (VanA/VanB/VanC1/VanC2/VanC3), production of gelatinase (Gel), aggregation substance (AS), adhesin of collagen from enterococci (Ace), *enterococcus* surface protein (Esp), haemolysin/bacteriocin (Cyl) and non-cytolysin beta hemolysin genes were studied by in vitro tests and/or PCR screening. DNA was extracted from *E. mundtii* ST4 according to standard methods. The primers designed for amplification of the latter genes were as described. The results are shown in Table 14.

Production of Gelatinase

Production of gelatinase was tested on MRS agar containing 30 g gelatin/liter. A clear zone surrounding the colonies after 18 h at 37° C. was considered a positive reaction. No production of gelatinase was detected.

Production of β-Hemolysin

Production of β-hemolysin was indicated by the formation of clear zones surrounding the colonies on blood agar plates. Blood agar plates were prepared using Columbia Blood Agar Base with 5% sheep blood. No production of β-hemolysin was observed.

It is evident that the Applicant has shown that strain ST4SA does not have the genes encoding vancomycin resistance, gelatinase production, production of the endocarditis antigen, forming of cell aggregates, adherence to collagen, and/or production of a surface protein. Genes encoding β-hemolysin activity and non-cytolysin beta hemolysin III were detected. However, the latter two genes are not expressed (no haemolytic activity was observed on blood agar plates—see below)

Determination of Bile-Salt Hydrolytic (BSH) Activity

Strain ST4SA was tested for BSH activity by spotting 10 µl of an overnight culture on MRS agar plates supplemented with 0.5% (w/v) sodium salt of taurodeoxycholic acid (TCDA) and 0.37 g/L $CaCl_2$. Plates were incubated in anaerobic jars for 72 h at 37° C. The formation of precipitation zones were regarded BSH positive.

No bile salt hydrolytic (BSH) activity was observed for strain ST4SA. BSH activity may contribute to resistance of lactic acid bacteria to the toxicity of conjugated bile salts in the duodenum. However, bile salt hydrolase activity and resistance to bile salts are generally accepted as being unrelated.

Determination of Cell Surface Hydrophobicity

An overnight culture of *E. mundtii* ST4SA was washed twice with quarter-strength Ringer's solution (QSRS) and the $OD_{580nm}$ determined. Equal volumes of suspension and n-hexadecane was added together and mixed for 2 min. The phases were allowed to separate at room temperature for 30 min., after which 1 ml of the water-phase was removed and the $OD_{580nm}$ determined. The $OD_{580nm}$ of duplicate assessments was averaged and used to calculate hydrophobicity:

% Hydrophobicity=[($OD_{580nm}$reading1−$OD_{580}$reading2)/$OD_{580nm}$reading1]×100.

Figure 28:
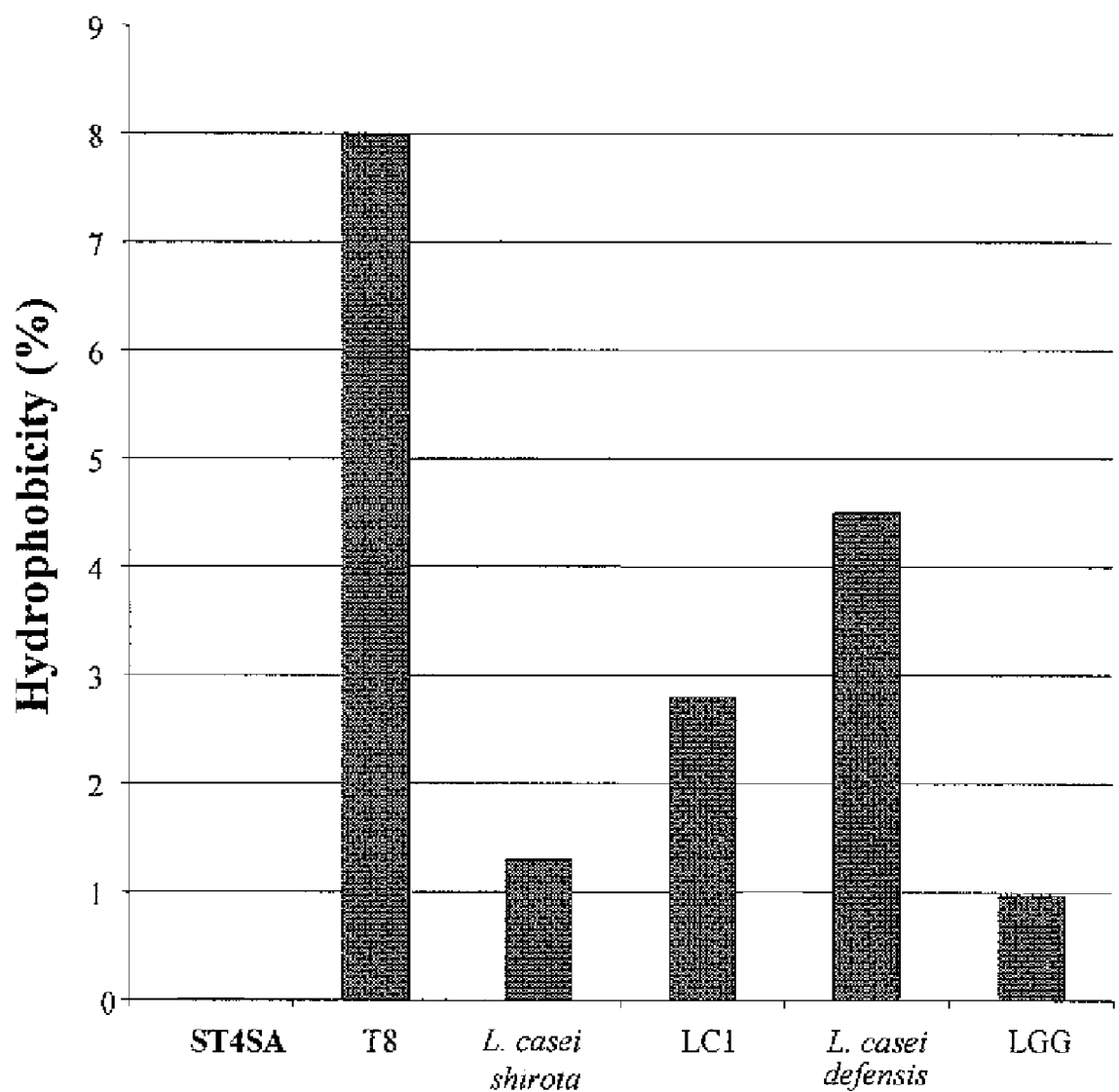
FIG. 28 shows a hydrophobicity plot of ST4SA.

From the results shown in FIG. 28 figure it is evident that strain ST4SA did not show signs of hydrophobicity. Accordingly, the cells do not stick permanently to surfaces in the GIT. The cells move freely (as planktonic cells) in the gut, which enhances the usefulness thereof as a good probiotic.

TABLE 14

| | Van A | Van B | Van C1/2/3 | Gel | Efa-Afm | Efa-Afs | AS | Ace | Cyl | Esp | Non-cyt |
|---|---|---|---|---|---|---|---|---|---|---|---|
| ST4SA | − | − | − | − | − | − | − | − | + | − | + |

Key:
VanA/VanB: Vancomycin resistance
Gel: Gelatinase production
EfaAfm: *E. faecium* endocarditis antigen
EfaAfs: *E. faecalis* endocarditis antigen
As: Aggregation substance
Ace: Adhesin to collagen from *E. faecalis*
Cyl: Cytolysin (β-hemolysin activity)
Esp: *Enterococcus* surface protein
Non-Cyt: non-cytolysin beta hemolysin III Production of Aggregation Substance (AS)

Production of AS was studied in a clumping assay in the presence of a sex pheromone. Sex pheromone was obtained by growing the pheromone producer, *Enterococcus faecalis* JH2-2, in MRS broth at 37° C. for 18 h. The supernatant of a pheromone producer, *E. faecalis* OG1X, was used in clumping assays in a microtiter plate. Two-hundred microliters were inoculated (0.5%, v/v) with strain ST4SA and microscopically examined for cell clumping after 2, 4, 8 and 24 h. No cell clumping was observed Adhesion of *E. Mundtii* ST4SA and *Listeria monocytogenes* to Caco-2 Cell Lines Caco-2 cells (Highveld Biological Sciences) were seeded at a concentration of $5 \times 10^5$ cells per well to obtain confluence. Adherence was examined by adding 100 µl of bacterial suspension ($1 \times 10^5$ cfu/ml of strain ST4SA and $1 \times 10^3$ cfu/ml of *L. monocytogenes*) to the wells. After incubation at 37° C. for 2 h, the cell lines were washed twice with PBS. The bacterial cells were lysed with Triton-X 100 and plated onto MRS and BHI agar, respectively. Adhesion was calculated from the initial viable counts and the cell lysates.

Competitive exclusion of strain ST4SA and *Listeria monocytogenes* was determined by inoculating 100 µl of each strain to the cell monolayer. After a 2 h incubation period the cells were lysed and plated out on *Enterococcus* and *Listeria* specific medium, respectively.

Caco-2 cell monolayers were prepared on glass coverslips in 12-well tissue culture plates. A suspension of ST4SA cells was added to the wells. After a 2 h adhesion period, the cell lines were washed twice with PBS, fixed with 10% formalin and gram-stained. Adherent bacteria were examined microscopically. The results are shown in Table 15 and Table 16.

TABLE 15

| Cfu/ml | Inoculum of ST4 | Adhesion of ST4 | Inoculum of *L. Monocytogenes* | Adhesion of *L. monocytogenes* |
|---|---|---|---|---|
| Experiment 1 | $1 \times 10^6$ | $2 \times 10^4$ | $1 \times 10^5$ | $3 \times 10^2$ |
| Experiment 2 | $1 \times 10^6$ | $1 \times 10^4$ | $3 \times 10^4$ | $1 \times 10^3$ |

TABLE 16

| Cfu/ml | Inoculum of ST4 | Adhesion of ST4 | Inoculum of *L. Monocytogenes* | Adhesion of *L. monocytogenes* |
|---|---|---|---|---|
| Experiment 1 | $1 \times 10^6$ | $8 \times 10^3$ | $1 \times 10^5$ | $4 \times 10^1$ |
| Experiment 2 | $1 \times 10^6$ | $1 \times 10^4$ | $3 \times 10^4$ | $3 \times 10^3$ |

From the results presented in Tables 15 and 16 it is clear that *E. mundtii* ST4SA cells prevented the adhesion of *Listeria* to Caco-2 cells and that the cells successfully competed against *Listeria* for recognition sites on the human cell line. Strain ST4SA is thus able to out-compete *Listeria*.

*L. monocytogenes* Challenged with ST4SA and Survival in an In Vitro Gastro-Intestinal (GIT) Model The antimicrobial activity of ST4SA against *L. monocytogenes* in an in vitro gastro-intestinal model was determined. ST4SA was inoculated in the stomach vessel as described hereinbefore. *L. monocytogenes* ($1 \times 10^4$) was inoculated in the duodenum vessel of the GIT. Samples were taken from each vessel and plated out on *Enterococcus* and *Listeria* specific medium, respectively. As control, only *L. monocytogenes* was inoculated in the GIT model.

Figure 29:
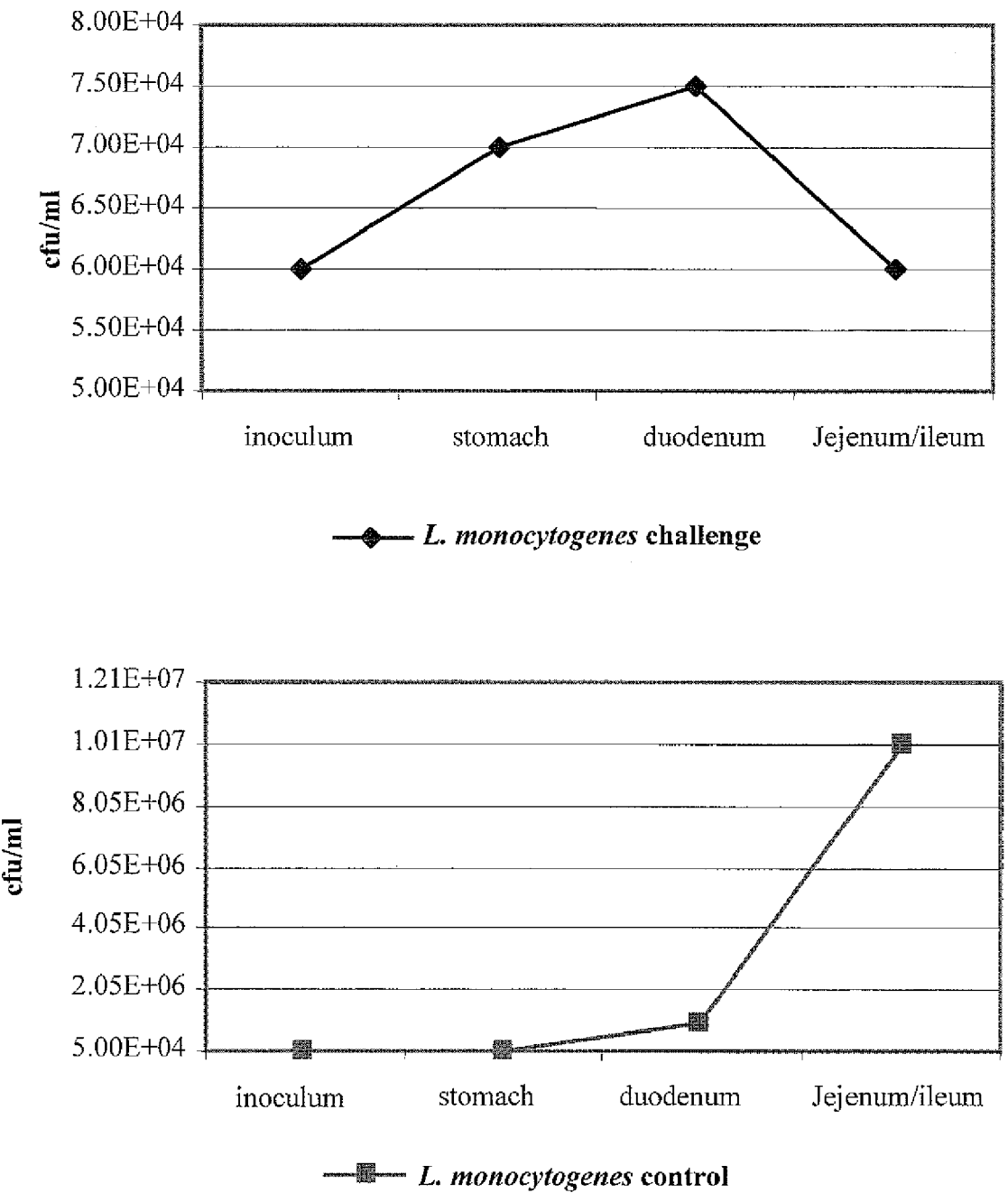
FIG. 29 shows the results of L. monocytogenes challenge with ST4SA and survival in an in vitro GIT model.

The *L. monocytogenes* challenge with ST4SA in the in vitro GIT model revealed that ST4 had an antimicrobial effect on *L. monocytogenes* (see graphs on next page). Growth was reduced from $8 \times 10^4$ to $2 \times 10^4$ in the jejunum vessel and *L. monocytogenes* was $1 \times 10^1$ cfu/ml lower in the ileum vessel when compared with the control, as shown in FIG. 29.

In Vivo Assessment of the Safety, Bacterial Translocation, Survival and Immune Modulation Capacities of Orally Administered *E. Mundtii* ST4SA: Comparison to Lactovita Materials and Methods Animals Ten male Wistar rats weighing between 318 g and 335 g were housed in groups of five in plastic cages with 12-hour light/dark cycle, in a controlled atmosphere (temperature 20° C.±3° C.). The animals were fed a standard diet, as well as autoclaved, reverse osmosis water either supplemented with probiotic or unsupplemented ad lib.

Bacterial Strains and Probiotic

Strain ST4SA was cultured in MRS Broth at 30° C. for 18 hours; the optical density was adjusted to 1.8 at 600 nm. Cells were harvested by centrifugation and washed in 20 mM phosphate buffer (pH 7.5). Washed cells were re-suspended in 100 mM sucrose, frozen in liquid nitrogen and lyophilized overnight. The cfu/ml value was determined by suspending a given mass of cells in 1 ml of phosphate buffer and spread plating dilutions on MRS solid media. Strain ST4SA was added to drinking water at a concentration of approximately $2 \times 10^8$ cfu/ml.

Three capsules containing a probiotic commercially available under the trade name Lactovita were opened and added to each bottle of drinking water. This resulted in approximately $3 \times 10^5$ cfu/ml being administered.

Experimental Design

Two separate studies were conducted. In each study 10 rats were randomly divided into two groups of five each. One group acted as a control and received unsupplemented water; the second group received water supplemented with either Lactovita capsules or lyophilized strain ST4SA. Each rat received a total of either $9.89 \times 10^{11}$ cfu of strain ST4 or $3.1 \times 10^9$ cfu of Lactovita over the study period. The rats were monitored daily for any abnormal activities, behaviours and general health status including ruffled coat, hunched posture, unstable movement, tremors or shaking, coughing or breathing difficulties, colour of extremities. Activity was monitored using a three-scale method: 1=lazy, moving slowly; 2=intermediate; 3=active moving or searching. Live weights and volume of water consumed were measured daily. The strain ST4SA study was conducted over 50 days and the Lactovita study over 108 days and the results are shown in Table 17.

TABLE 17

|  | Control | ST4 | Control | Lactovita |
|---|---|---|---|---|
| Increase (g) | 144 (7.22) | 150.60 (9.34) | 255.2 (21.88) | 246 (44.42) |
| Increase (%) | 69.46 (1.10) | 69.19 (1.05) | 56.04 (2.59) | 57.21 (5.60) |

β-Glucuronidase Activity

Rats were placed in single cages overnight at specified sampling points and the 24 h faecal samples were collected to determine bacterial counts and β-glucuronidase activity. Faecal samples were homogenized in 20 mM phosphate buffer at a concentration of 100 mg faeces/ml buffer. Samples were stored at −20° C. until analysis. The faecal samples were pelleted by centrifugation and resuspended in 1 ml GUS extraction buffer (50 mM NaHPO$_4$, 5 mM DTT, 1 mM EDTA, 0.1% Triton X-100), mixed and incubated at 22° C. for 10 minutes. Samples were frozen overnight at −20° C. and thawed before determining β-glucuronidase activity. β-Glucuronidase activity was assayed by incubating 100 µl of treated faecal suspension with 900 µl of reaction buffer (extraction buffer containing 1 mM ρ-nitrophenyl glucuronide) and incubating at 37° C. for 2 hours. The reaction was stopped by adding 2.5 ml 1M Tris, pH 10.4. The absorbance was determined at 415 nm and a standard curve was constructed using concentrations of 0.1, 0.2, 0.5, 1 and 10 mM ρ-nitrophenol.

Bacterial Translocation, Toxicological Study and Histology

After feeding with test strains for the specified time periods, animals were euthanized by pentobarbitone sodium overdose. Blood samples were obtained by cardiac puncture of the right ventricle. The gross anatomy of the visceral organs of each rat was checked and recorded. A sample of the liver, spleen, ileum, caecum and colon tissues was excised. The tissue samples were collected in cassettes and placed in a 4% formaldehyde (PBS) solution and then embedded in paraffin wax for histological analysis and FISH studies. A section of the ileum and colon were frozen in liquid nitrogen. Blood samples were spread plated on BHI solid media and incubated at 37° C. overnight.

Immune Modulation

Total RNA was extracted from the frozen ileum and colon samples using Trizol reagent. The concentration of RNA was determined by measuring the absorbance at 260 nm using a Nanodrop spectrophotometer, after DNase treatment had been completed. Each RNA sample was diluted to a concentration of 42 ng/µl. A total of 5 µg of each sample was transferred in triplicate onto a nylon membrane using a slot blot apparatus. The membrane was then probed with either a tumour necrosis factor (TNF), interferon γ (IFN) or β-actin DNA probe amplified from rat genomic DNA and labeled with DIG. The membrane was exposed to X-ray film overnight and developed.

Results

General Health Status and Weight Gain

Throughout the study period there were no noticeable behavioural or activity changes observed in the rats and there were no observable differences between experimental and control groups. No treatment-related illness or death occurred.

β-Glucuronidase Activity

Bacterial enzymes, including β-glucuronidase, are known to be involved in generating mutagens, carcinogens and tumour promoters from precursors found in the GIT and there presence may indicate toxicity of bacterial strains and can therefore be used as an indication of the safety of potential probiotics. Both strain ST4SA and a Lactovita suspension exhibited no β-glucuronidase activity in vitro (data not shown). However, rats given a Lactovita suspension showed an increase in β-glucuronidase activity in faecal samples compared to control rats (Table 18A). Control animals also showed a decrease in activity at day 107 of the study compared to activity at day 56, experimental animals showed slightly increase values at day 107 compared to day 56. Rats given a ST4 supplement showed higher β-glucuronidase activity compared to control groups (Table 18B), however, this activity was still lower at the end of the study compared to the values on day 0 of the study. The control group also showed lower activity at the end of the study compared to day 0.

TABLE 18

Table 18A

|  | Day 56 | Day 77 | Day 107 |
| --- | --- | --- | --- |
| Lactovita | 6.58 (0.34) | 7.49 (0.23) | 7.88 (0.36) |
| Control | 7.52 (0.26) | 8.17 (0.08) | 6.70 (0.32) |

Table 18B

|  | Day 0 | Day 14 | Day 30 | Day 50 |
| --- | --- | --- | --- | --- |
| ST4 | 6.43 (0.52) | 1.78 (0.45) | 5.25 (0.57) | 5.14 (0.83) |
| Control | 5.78 (0.50) | 2.40 (0.76) | 4.02 (0.62) | 2.68 (0.15) |

Bacterial Translocation, Toxicological Study and Histology

No bacteraemia was detected in any of the groups of animals. Macroscopic examination of the visceral organs indicated that the rats given strain ST4SA had significantly more pronounced MLN compared to control rats. The MLN were extremely difficult to identify in control rats. The spleen in the control group was narrower and both muscle mass and abdominal fat were less in the control group compared to the experimental group. In animals given Lactovita the MLN were less pronounced and the spleen smaller compared to the control group.

Lymphocytes enter the spleen and facilitate immune responses against blood antigens. An enlarged spleen may indicate increase immune system activity. This also correlates with pronounced MLN. MLN are also involved in immune function and may enlarge as a result of inflammation or infection. This enlargement is an indication that they are performing their function as expected. Therefore strain ST4SA may act as an immune stimulant. Rats receiving Lactovita supplements showed a smaller spleen and less pronounced MLN compared to the control rats. This indicates that Lactovita does not induce an immune reaction. However, the MLN and spleen of the control rats were enlarged and no symptoms of disease were observed in the absence of any immune stimulant.

Immune Modulation

Northern hybridization studies did not indicate any cytokine (TNF or IFN) expression in either the experimental ST4SA group or control group. Positive signals were detected of relatively the same intensity when RNA was probed with a β-actin DNA probe indicating the presence of RNA.

Cytokines are secreted proteins that mediate cell growth, inflammation, immunity, differentiation and repair. They often only require femtomolar concentrations to produce their required effects. Often they act in combination with cell surface receptors to produce changes in the pattern of RNA and protein synthesis. Because they are usually present in such low concentrations it may be more beneficial to determine the expression of additional genes that are under the influence of these proteins.

The results presented herein indicate that neither of the probiotics tested have any negative effects on the general health status of male Wistar rats.

In summary, strain ST4SA does not possess genes encoding vancomycin resistance. Genes encoding β-hemolysin activity and non-cytolysin beta hemolysin III were detected, but they remained silent (not expressed). Strain ST4SA has no bile salt hydrolytic (BSH) activity. This indicates that the strain would perform better in the lower sections of the GIT (ileum and colon). As shown above, the data indicate that E. mundtii strain ST4SA moves freely through the GIT and prevents the adhesion of Listeria to Caco-2 cells, while also successfully competing against Listeria from binding to receptors on human cells. Strain ST4SA had an antimicrobial effect on L. monocytogenes in gastro-intestinal model (GIM) studies. Strain ST4SA is not toxic, as shown with rat studies. No treatment-related illness or death occurred. Strain ST4SA also performed better than Lactovita as such, with rats being given Lactovita showing an increase in β-glucuronidase activity; strain ST4SA therefore stimulates the immune response in rats. Rats given Lactovita supplements showed a smaller spleen and less pronounced MLN compared to the control rats, which suggest that Lactovita does not induce an immune reaction.

As indicated above, peptide ST4SA inhibits the growth of a variety of bacteria and maximal production of peptide ST4SA (51 200 AU/ml) was recorded after 20 h of growth in MRS broth (Biolab), which was maintained throughout fermentation.

An 18-h-old culture of strain ST4SA was inoculated (2%, v/v, $OD_{600nm}$=2.0) into MRS broth (Biolab) and filtered MRS broth, respectively. MRS broth (Biolab) was filtered through a Minitan™ system (Millipore, BioSciences International), equipped with nitrocellulose membranes of 6000-8000 Da in pore size. The MRS filtrate (MRSf), containing proteins smaller than 8 000 Da was then autoclaved and inoculated as described before. Incubation in MRS broth and MRSf was at 30° C. and 37° C., without agitation, for 29 h. Peptide ST4SA activity was determined two-hourly.

Purification of Peptide ST4SA

One liter of MRSf was inoculated with *Enterococcus mundtii* ST4SA ($OD_{600nm}$=1.8) and incubated at 30° C. for 24 h. The cells were harvested by centrifugation (8 000×g, 4° C., 15 min) and the cell-free supernatant incubated at 80° C. for 10 min. Ammonium sulfate was gently added to the cell-free supernatant at 4° C. to a saturation level of 60%. After 4 h of slow stirring, the precipitate was collected by centrifugation (20 000×g, 1 h, 4° C.). The pellet was resuspended in one-tenth volume 25 mM ammonium acetate (pH 6.5) and desalted against sterile MilliQ water using a 1.0 kDa cut-off Spectra/Por dialysis membrane (Spectrum Inc., CA, USA). Further separation was by cation exchange chromatography in a 1 ml Resource S column (Amersham Biosciences) with an ÄKTApurifier (Amersham), as described hereinbefore.

Peptide ST4SA activity levels obtained after each purification step are indicated in Table 19.

TABLE 19

| Sample | Activity (AU/ml) | Total protein (µg/ml) | Specific activity (AU/µg protein) | Yield (%) | Purification Factor |
|---|---|---|---|---|---|
| Cell-free supernatant (450 ml) | 12 800 | 10.77 | 1 188.49 | 100 | 1 |
| Ammoniun sulphate precipitate (45 ml) | 102 400 | 82.31 | 1 244.08 | 80 | 1.1 |
| Dialysate (45 ml) | 102 400 | 35.77 | 2 862.73 | 80 | 2.4 |

Active fractions collected from the ÄKTApurifier corresponded to the ST4SA peak and produced a 42-amino acid peptide, the expected size of peptide ST4SA.

Iso-electric Focusing of Peptide ST4SA

Iso-electric focusing of peptide ST4SA was done by using the Rotofor® electro-focusing cell (Bio-Rad, Hercules, Calif., USA). One liter of cell-free supernatant, obtained from strain ST4SA cultured in MRSf, and prepared as described before, was lyophilized and resuspended in 50 ml sterile distilled water with ampholytes (pH-range 3 to 10, Bio-Rad), according to instructions of the manufacturer. A constant current of 12 W was applied for 5 h at 8° C. After separation, a small volume from each of the collected fractions was adjusted to pH 7.0 with 3 N NaOH or 3 N HCl and tested for antimicrobial activity against *Lactobacillus casei* LHS. The fractions that tested positive were pooled, resuspended in de-ionized water to a total volume of 50 ml, again subjected to electro-focusing, the fractions collected and tested for antimicrobial activity. Samples were stored at −20° C.

Cost reduction of cultivation media forms an important part of media optimization. Media costs can be lowered by using industrial media as a carbon and/or nitrogen source. Corn steep liquor (CSL), cheese whey powder (CWp) and molasses are regularly used as part of growth media. CSL is a by-product formed during the milling of corn. It is mainly a nitrogen source, but also contains sugars (mainly sucrose), vitamins and minerals. Cheese whey, a by-product in the diary industry, is the most common fermentation medium for lactic acid (LA) production, and contains mainly lactose, proteins and salts. Molasses is a by-product containing mainly sucrose with traces of other minerals.

Culture and Media

Strain ST4SA was cultured in MRS broth (Biolab) and inoculated (2% v/v) into CSL, CWp and molasses, respectively.

Fermentations

Fermentations were conducted in test tubes containing 10 ml of media. The pH was adjusted with NaOH before sterilization (121° C. for 15 min). The concentration of NaOH depended on the buffer capacity of the media. A 24-hour-old culture was used for inoculation (2% v/v). Batch fermentations were conducted in test tubes at 30° C. for 16 hours, pH 6.5-7.0. The pH was not controlled. Optical density (OD) was measured at 600 nm.

Molasses and CSL at 10, 20 and 50 $g \cdot l^{-1}$ were evaluated as possible media for peptide ST4SA production (Table 20). Although the pH in molasses dropped during fermentation (thus indicating cell growth), no peptide ST4SA activity was recorded in the supernatant. CSL, on the other hand, produced a supernatant with activity of up to 3200 $AU \cdot ml^{-1}$ at a minimum concentration of 20 $g \cdot l^{-1}$. As may be concluded from these results, a nitrogen source (CSL) is required to sustain peptide ST4SA production.

TABLE 20

| | | | pH | | |
|---|---|---|---|---|---|
| No. | Media | | Initial | End | $AU\ ml^{-1}$ |
| | | $g\ l^{-1}$ | | | |
| 1 | MRS (Control) | | 6.50 | 4.65 | 12800 |
| 2 | CSL | 10 | 6.50 | 4.38 | 1600 |
| 3 | | 20 | 6.50 | 4.41 | 3200 |
| 4 | | 50 | 6.50 | 4.56 | 3200 |
| 5 | Molasses | 10 | 6.50 | 4.82 | 0 |
| 6 | | 20 | 6.50 | 5.01 | 0 |
| 7 | | 50 | 6.50 | 4.97 | 0 |
| | | $g\ TS\ l^{-1}$ | | | |
| 8 | CWp | 10 | 6.27 | 4.14 | 800 |
| 9 | | 20 | 6.55 | 4.44 | 800 |
| 10 | | 50 | 6.47 | 4.82 | 1600 |

In follow-up experiments, CWp was added to the list of industrial media and fermented at 10, 20 and 50 $g\ TS \cdot l^{-1}$ (Table 20). Peptide ST4SA activity of up to 1600 $AU \cdot ml^{-1}$ was recorded in CWp (Table 20).

A full factorial design (FFD) with CSL and CWp as components was used to determine which media had the most significant effect on peptide ST4SA production (Table 21). The FFD would also give an indication as to whether there was any interaction between the nutrients.

TABLE 21

$2^2$ FED with CSL and CWp

| No. | CSL | CWp | pH Initial | pH End | AU ml$^{-1}$ |
|---|---|---|---|---|---|
| 1 | 1 | 1 | 6.490 | 5.510 | 12800 |
| 2 | -1 | 1 | 6.490 | 5.100 | 12800 |
| 3 | 1 | -1 | 6.450 | 5.430 | 12800 |
| 4 | -1 | -1 | 6.480 | 5.090 | 12800 |
| MRS | | | 6.86 | 4.53 | 51200 |
| CSL 5 g TS l$^{-1}$ | | | 6.51 | 5.04 | 12800 |
| CSL 10 g TS l$^{-1}$ | | | 6.47 | 5.12 | 12800 |

The utilization of sugars was determined by using the following methods:

Phenol-sulphuric Acid Assay for Total Sugars

Phenol (500 μl of a 5%, v/v) and concentrated sulphuric acid (2.5 ml) were added to 500 μl of diluted sample in a test tube. The solutions were thoroughly vortexed and absorbancy readings taken at 490 nm (room temperature). Sugar concentration (g glucose·l$^{-1}$) was calculated using a standard graph.

Dionex Determination of Monomer Sugars

A Dionex DX500 analyser with a CarboPac PA100 column was used to analyse the samples for monomer sugars. The eluent used was 250 mM NaOH, H$_2$O and 1M NaOAc at a flow rate of 1 ml·min$^{-1}$. The Dionex was equipped with an auto sampler and the injection volume was 10 μl.

Total sugar concentrations varied between 5 and 10 g TS·l$^{-1}$ (represented by "-1" and "1" respectively). The results (experiment performed in duplicate) suggested that the concentration of CSL and CWp had no effect on peptide ST4SA production (Table 21). CSL at 5 and 10 g TS·l$^{-1}$ yielded peptide ST4SA activity similar to that recorded in the CSL and CWp combination (Table 21) and four-fold higher than recorded with 50 g·l$^{-1}$ CSL (Table 20). As is evident from these results, CSL had the most significant effect on peptide ST4SA production.

Optimizing CSL

Peptide ST4SA activity of up to 12800 AU ml$^{-1}$ was recorded in pure CSL at a concentration of 10 g TS·l$^{-1}$. This was, however, low compared to peptide ST4SA activity recorded in MRS (51200 AU·ml$^{-1}$). In a preliminary experiment, MRS components (except glucose) were added to 10 and 40 g TS·l$^{-1}$ CSL and CWp, respectively (Table 22). A two-fold increase in activity was observed for 10 g TS·l$^{-1}$ CSL with supplements compared to pure CSL. In contrast, CSL at 40 g TS·l$^{-1}$ with supplements yielded low activity. A high concentration of CSL inhibited growth (small decrease in pH) and, subsequently, also peptide ST4SA production. This may be due to inhibiting components in CSL. The same experiment was done with CWp (Table 22). With an increase in CWp concentration (from 10 to 40 g TS·l$^{-1}$), no effect on peptide ST4SA production was recorded.

TABLE 22

CSL supplemented with MRS components

| No. | Carbon source | g TS l$^{-1}$ | pH Initial | pH End | AU ml$^{-1}$ |
|---|---|---|---|---|---|
| 1 | CSL | 10 | 6.52 | 5.47 | 25600 |
| 2 | | 40 | 6.55 | 6.26 | 800 |
| 3 | CWp | 10 | 6.51 | 4.92 | 12800 |
| 4 | | 40 | 6.50 | 5.07 | 12800 |

At 10 g TS·l$^{-1}$ CSL produced peptide ST4SA at twice the activity compared to CWp (25600 AU·ml$^{-1}$). CSL was therefore chosen as medium for future experiments.

As not all of the MRS components played a role in improving peptide ST4SA production, a screening experiment was done to identify the significant components. This screening experiment was done via a $2^{10-5}$ fractional factorial design (FrFD). The design made it possible to test 10 factors in only 32 runs, instead of the normal 1024 runs (Tables 23 and 24). It was also possible to determine if there were any interactions between components. Results were analyzed with ANOVA (Table 25).

TABLE 23

High and low concentrations of MRS components and CSL

| | Component | g l$^{-1}$ | MRS broth g l$^{-1}$ 1 | MRS broth g l$^{-1}$ -1 |
|---|---|---|---|---|
| A | Special peptone | 10 | 10 | 0 |
| B | Beef extract | 5 | 5 | 0 |
| C | Yeast extract | 5 | 5 | 0 |
| D | CSL | — | 6 | 3 |
| E | Potassium phosphate | 2 | 2 | 0 |
| F | Tween80 | 1 | 1 | 0 |
| G | tri-Ammonium citrate | 2 | 2 | 0 |
| H | MgSO$_4$ | 0.1 | 0.1 | 0 |
| J | MnSO$_4$ | 0.05 | 0.05 | 0 |
| K | Sodium acetate | 5 | 5 | 0 |

Linear model in terms of coded values:
Activity = -1431.2 * B + 956.2 * C + 3831.2 * D - 2781.3 * E - 2243.8 * G - 2006.2 * K + 7668.8 [Equation 2]
$R^2 = 0.73$ Peptide ST4SA production was described using a linear model. Although the linear model could not accurately predict the activity ($R^2 = 0.73$), it could still be used to evaluate the effect (positive or negative) of the components. Beef extract (B), potassium phosphate (E), tri-ammonium citrate (G) and sodium acetate (K) had negative coefficients in the linear model (equation 2) causing a decrease in the response variable. This reflected their negative effect on peptide ST4SA production. This meant that only yeast extract (YE) (C) and CSL (D) increased peptide ST4SA production.

TABLE 24

$2^{10-5}$ FrFD design

| No. | A | B | C | D | E | F = ABCD | G = ABCE | H = ABDE | J = ACDE | K = BCDE |
|---|---|---|---|---|---|---|---|---|---|---|
| 1 | -1 | -1 | -1 | -1 | -1 | 1 | 1 | 1 | 1 | 1 |
| 2 | 1 | -1 | -1 | -1 | -1 | -1 | -1 | -1 | -1 | 1 |
| 3 | -1 | 1 | -1 | -1 | -1 | -1 | -1 | -1 | 1 | -1 |
| 4 | 1 | 1 | -1 | -1 | -1 | 1 | 1 | 1 | -1 | -1 |

TABLE 24-continued $2^{10-5}$ FrFD design

| No. | A | B | C | D | E | F = ABCD | G = ABCE | H = ABDE | J = ACDE | K = BCDE |
|---|---|---|---|---|---|---|---|---|---|---|
| 5  | -1 | -1 | 1  | -1 | -1 | -1 | -1 | 1  | -1 | -1 |
| 6  | 1  | -1 | 1  | -1 | -1 | 1  | 1  | -1 | 1  | -1 |
| 7  | -1 | 1  | 1  | -1 | -1 | 1  | 1  | -1 | -1 | 1  |
| 8  | 1  | 1  | 1  | -1 | -1 | -1 | -1 | 1  | 1  | 1  |
| 9  | -1 | -1 | -1 | 1  | -1 | -1 | 1  | -1 | -1 | -1 |
| 10 | 1  | -1 | -1 | 1  | -1 | 1  | -1 | 1  | 1  | -1 |
| 11 | -1 | 1  | -1 | 1  | -1 | 1  | -1 | 1  | -1 | 1  |
| 12 | 1  | 1  | -1 | 1  | -1 | -1 | 1  | -1 | 1  | 1  |
| 13 | -1 | -1 | 1  | 1  | -1 | 1  | -1 | -1 | 1  | 1  |
| 14 | 1  | -1 | 1  | 1  | -1 | -1 | 1  | 1  | -1 | 1  |
| 15 | -1 | 1  | 1  | 1  | -1 | -1 | 1  | 1  | 1  | -1 |
| 16 | 1  | 1  | 1  | 1  | -1 | 1  | -1 | -1 | -1 | -1 |
| 17 | -1 | -1 | -1 | -1 | 1  | 1  | -1 | -1 | -1 | -1 |
| 18 | 1  | -1 | -1 | -1 | 1  | -1 | 1  | 1  | 1  | -1 |
| 19 | -1 | 1  | -1 | -1 | 1  | -1 | 1  | 1  | -1 | 1  |
| 20 | 1  | 1  | -1 | -1 | 1  | 1  | -1 | -1 | 1  | 1  |
| 21 | -1 | -1 | 1  | -1 | 1  | -1 | 1  | -1 | 1  | 1  |
| 22 | 1  | -1 | 1  | -1 | 1  | 1  | -1 | 1  | -1 | 1  |
| 23 | -1 | 1  | 1  | -1 | 1  | 1  | -1 | 1  | 1  | -1 |
| 24 | 1  | 1  | 1  | -1 | 1  | -1 | 1  | -1 | -1 | -1 |
| 25 | -1 | -1 | -1 | 1  | 1  | -1 | -1 | 1  | 1  | 1  |
| 26 | 1  | -1 | -1 | 1  | 1  | 1  | 1  | -1 | -1 | 1  |
| 27 | -1 | 1  | -1 | 1  | 1  | 1  | 1  | -1 | 1  | -1 |
| 28 | 1  | 1  | -1 | 1  | 1  | -1 | -1 | 1  | -1 | -1 |
| 29 | -1 | -1 | 1  | 1  | 1  | 1  | 1  | 1  | -1 | -1 |
| 30 | 1  | -1 | 1  | 1  | 1  | -1 | -1 | -1 | 1  | -1 |
| 31 | -1 | 1  | 1  | 1  | 1  | -1 | -1 | -1 | -1 | 1  |
| 32 | 1  | 1  | 1  | 1  | 1  | 1  | 1  | 1  | 1  | 1  |

TABLE 25

Analysis of Variance Table for a $2^{10-5}$ FrFD design

Response: Activity (AU ml$^{-1}$)

| Component | Df | F value | Pr (>F) |
|---|---|---|---|
| A | 1 | 0.950 | 0.334 |
| B | 1 | 8.858 | 0.004** |
| C | 1 | 3.954 | 0.052. |
| D | 1 | 63.474 | 1.435e-10*** |
| E | 1 | 33.450 | 4.221e-07*** |
| F | 1 | 0.162 | 0.689 |
| G | 1 | 21.770 | 2.191e-05*** |
| H | 1 | 0.207 | 0.651 |
| J | 1 | 0.008 | 0.928 |
| K | 1 | 17.405 | 0.000*** |
| Reproducibility | 1 | 1.338 | 0.253 |
| Residuals | 52 | | |

Signif. codes: 0 '*' 0.001 '' 0.01 '*' 0.05 '.' 0.1 ' ' 1

The concentrations of CSL and YE were set with a $2^2$ FFD (Table 26). The critical dilution method used for determination of peptide ST4SA activity did not yield accurate results. This made it impossible to fit a model relating the concentrations of CSL and YE to activity. Experimental results were used to fix the component concentrations. From Table 26 it can be seen that there was no clear effect when using low or high concentrations of CSL and YE. The average value was selected as the best, with a composition of CSL 7.5 g TS·l$^{-1}$ and YE 6.5 g·l$^{-1}$.

TABLE 26

$2^2$ FFD with 3 centre points for determination of CSL and YE concentrations

| | | | AU ml$^{-1}$ | | | g l$^{-1}$ | | |
|---|---|---|---|---|---|---|---|---|
| No. | C | D | Repl. 1 | Repl. 2 | Component | 1 | 0 | -1 |
| 1 | -1 | -1 | 25600 | 25600 | C  CSL | 10 | 6.5 | 3 |
| 2 | -1 | 1  | 25600 | 25600 | D  YE  | 10 | 7.5 | 5 |
| 3 | 1  | -1 | 36204 | 12800 | | | | |
| 4 | 1  | 1  | 25600 | 36204 | | | | |
| 5 | 0  | 0  | 25600 | 25600 | | | | |
| 6 | 0  | 0  | 25600 | 36204 | | | | |
| 7 | 0  | 0  | 51200 | 25600 | | | | |

Figure 30:
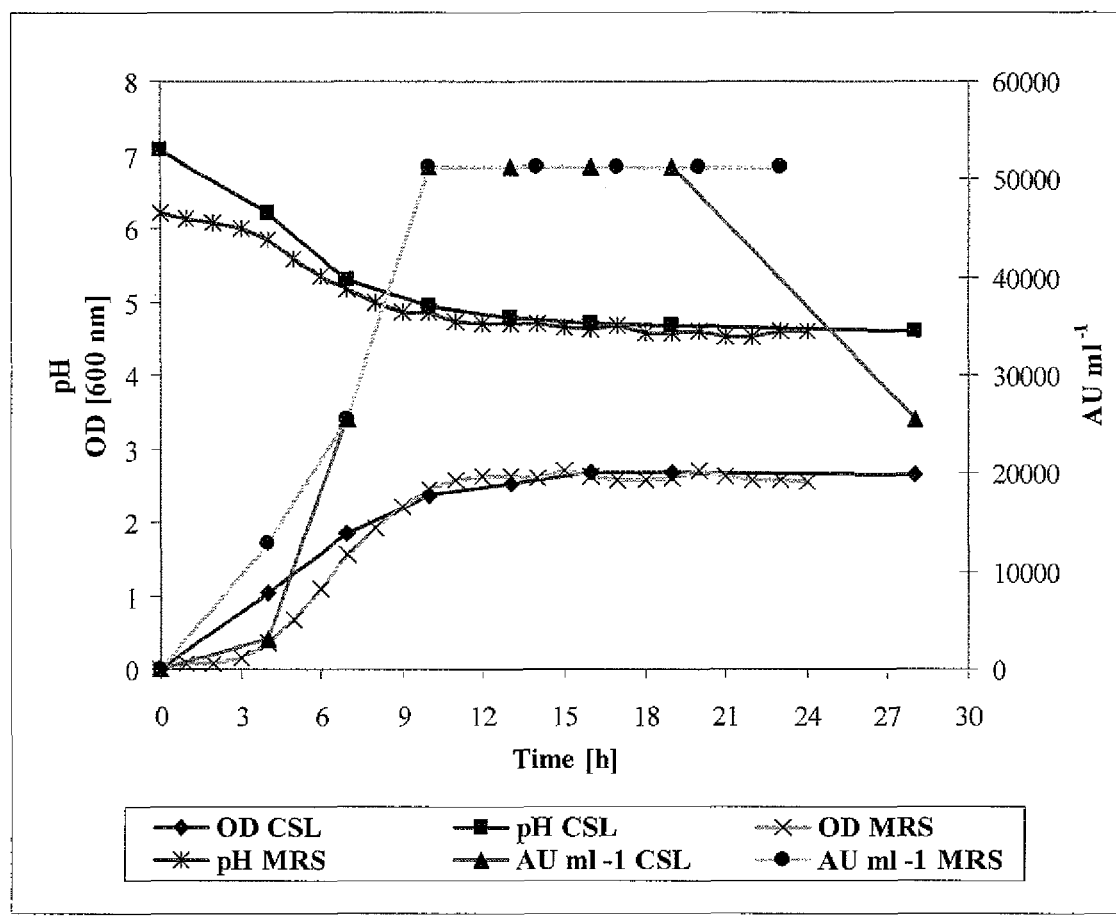
FIG. 30 shows growth curves of E. mundtii ST4SA in MRS broth and CSL media.

A growth curve with optimal media is shown in FIG. 30. CSL-based media and MRS yielded similar growth kinetics.

Batch to Batch Variation

The composition of CSL may vary on a daily basis, as it is a waste product. A difference in composition has the potential of significantly affecting results. This was investigated by performing the same experiments on a second batch of CSL. This time ANOVA analysis identified YE, CSL, Tween80, MnSO$_4$, and sodium acetate as the components having the most significant effect on bacteriocin production (P<0.1). Continued optimization showed that MnSO$_4$ was insignificant while sodium acetate caused a decrease in activity.

The final media consisted of the following three components: YE (C), CSL (D) and Tween80 (F). It was not surprising to find that yeast extract was once again one of the significant components. Tween80 has emulsifying properties. The final concentrations, as set in a $2^3$ FFD design, was: YE 7.5 g·l$^1$, CSL 10 g·l$^1$ and Tween80 2 g·l$^{-1}$.

Growth Limitations

The sugar content of the CSL medium was measured before and after fermentation. At the start of fermentation, CSL was made up to a concentration of 7.5 g TS·l$^{-1}$. The main monomer sugars present were glucose and fructose at a total concentration of 3.883 g·l$^{-1}$. Only about 51.8% of the total sugar was therefore in a fermentable form and not all sugars were metabolized during fermentation. At the end of fermentation (constant OD), the pH was 4.6 and the residual sugars left were 8.8%. Growth limitations were due to low pH and not due to a lack of nitrogen, minerals, vitamins or any other nutrients, and Table 27 shows the carbon uptake during fermentation.

TABLE 27

Carbon uptake during fermentation

| Time [h] | Glucose [g/l] | Fructose [g/l] | Total sugar [g/l] | % Sugar fermented |
|---|---|---|---|---|
| 0 | 1.747 | 2.136 | 3.883 | 0.0 |
| 10 | 0.391 | 0.899 | 1.290 | 66.8 |
| 19 | 0.041 | 0.301 | 0.342 | 91.2 |

Accordingly, it is evident that CSL supplemented with YE could match high peptide ST4SA levels obtained in commercial MRS broth. Advantageously, this has the potential of significantly reducing costs associated with cultivation media. CSL was selected as growth medium for industrial production of peptide ST4SA.

Development of *Enterococcus mundtii* ST4SA into a Probiotic

An important criterion for the selection of probiotic strains is adhesion to epithelial cells. Probiotic bacteria may also compete with pathogenic bacteria for adhesion sites. Caco-2 cells, which originate from human colon adenocarcinoma, were used as an in vitro model to investigate the adhesion and competitive exclusion abilities of *E. mundtii* ST4SA to epithelial cells.

The results are expressed as percentage of adherence compared to the inoculum. *E. mundtii* ST4SA and *L. monocytogenes* Scott A were able to adhere and both showed 5% adhesion to the Caco-2 cells. The adhesion of *E. mundtii* ST4SA was lowered to 1% when the incubation time was only 1 h. Food material stays in the small intestine for 2 h and therefore would allow sufficient time for *E. mundtii* ST4 to adhere to the epithelial cells. However, *E. mundtii* ST4SA did not have an effect on the adhesion of *L. monocytogenes* Scott A regardless of whether the strain was added before, during or after the incubation with the pathogen. In the exclusion and displacement tests, *L. monocytogenes* Scott A showed 5% adhesion. The competition test showed no competition for adhesion as the percentage adhesion stayed the same as in the control. This can be explained by the fact that *E. mundtii* ST4SA and *L. monocytogenes* Scott A might bind to different receptors on the epithelial cell. *E. mundtii* ST4SA and *L. monocytogenes* Scott A would, therefore, not compete for similar receptors.

Resistance of *E. Mundtii* ST4 Against Antibiotics and Anti-Inflammatory Drugs

*E. mundtii* ST4SA showed resistance against two antibiotics (Cefasyn and Utin) and the inflammatory medicaments Rheugesic, Coxflam and Pynmed. The results are shown in Table 28. Antibiotics with the greatest growth inhibition on *E. mundtii* ST4SA are Promoxil, Cipadur, Roxibidd and Doximal.

Promoxil, Doximal, Cefasyn and Utin had no effect on the adhesion of ST4SA cells to Caco-2 cells compared to the control. Adhesion decreased with 10% in the presence of Cipadur, Roxibudd and Ibugestic syrup and 14% with a higher concentration of Cefasyn, as may also be seen in Table 29.

TABLE 28

| Medicament | Strain ST4SA |
|---|---|
| Ibuprofen, 5 mg/ml | ++ |
| Aspirin, 5 mg/ml | + |
| Promoxil, 100 mg/ml | ++++ |
| Cipadur, 50 mg/ml | +++ |
| Cefasyn, 100 mg/ml | − |
| Roxibidd, 30 mg/ml | +++ |
| Doximal, 20 mg/ml | +++ |
| Ciploxx, 100 mg/ml | + |
| Utin, 80 mg/ml | − |
| Rheugesic, 4 mg/ml | − |
| Coxflam, 1.5 mg/ml | − |
| K-fenak, 5 mg/ml | ++ |
| Preflam, 3 mg/ml | + |
| Ibugesic | ++ |
| Pynmed | − |

− = no zones;
+ = diameters between 1 mm and 11 mm;
++ = diameters between 12 mm and 16 mm;
+++ = diameters of 17 mm and more.

TABLE 29

| Medicament | Strain ST4SA adhesion |
|---|---|
| Inoculum | $1 \times 10^7$ |
| Control | $5 \times 10^4$ |
| Cipadur (5 mg/ml) | $6 \times 10^3$ |
| Roxibidd (10 mg/ml) | $3 \times 10^3$ |
| Promoxil (8 mg/ml) | $1.25 \times 10^4$ |
| Doximal (2 mg/ml) | $1 \times 10^4$ |
| Cefasyn (10 mg/ml) | $1.2 \times 10^4$ |
| Cefasyn (50 mg/ml) | $7 \times 10^2$ |
| Utin (8 mg/ml) | $4 \times 10^4$ |
| Utin (40 mg/ml) | $3 \times 10^4$ |
| Ibugestic syrup (100 µl) | $6 \times 10^3$ |
| K-fenak (0.5 mg/l) | $3 \times 10^4$ |

In Vivo Assessment of the Safety, Toxicity, Bacterial Translocation and Survival, Immune Modulation Capacities and Efficacy of Orally Administered *E. Mundtii* ST4SA Cells—Comparisons with Lactovita.

Animals

Thirty six male Wistar rats weighing between 150 g and 180 g were housed in groups of six in plastic cages with 12-hour light/dark cycle, in a controlled atmosphere (temperature 20±3° C.). The animals were fed a standard diet and ad lib.

Bacterial Strains and Probiotic

*E. mundtii* strain ST4SA was cultured in MRS Broth at 30° C. for 18 hours; the optical density was adjusted to 1.8 at 600 nm. Cells were harvested by centrifugation and washed in 20 mM phosphate buffer (pH 7.5). Washed cells were resuspended in 100 mM sucrose, frozen at −80° C. and lyophilized overnight. The cfu/vial values were determined by suspending a given mass of cells in 1 ml of phosphate buffer and spread plating dilutions on MRS solid media. Lyophilized cells were resuspended in sterile skim milk (10%) and 2×10$^8$ cfu strain ST4SA was administered via intragastric gavage.

Lactovita capsules were emptied into a vial and resuspended in sterile skim milk (10%) and 2×10$^8$ cfu was administered via intragastric gavage.

*Listeria monocytogenes* Scott A was cultured in BHI Broth at 37° C. for 18 hours. Cells were harvested by centrifugation and washed in 20 mM phosphate buffer (pH 7.5). Washed cells were resuspended in 100 mM sucrose, frozen at −80° C. and lyophilized overnight. The number of cfu/vial was determined as described above. Lyophilised cells were resuspended in sterile skim milk (10%) and $10^4$ cfu were administered via intragastric gavage.

Experimental Design

Two groups of animals received strain ST4 via intragastric gavage, two groups received Lactovita and the remaining two control groups received water for 7 consecutive days. On day 8, both control groups were infected with *Listeria monocytogenes* and one group from each of the strain ST4SA and Lactovita groups was also infected with *L. monocytogenes* via intragastric gavage. At this time the animals also received *E. mundtii* strain ST4SA, Lactovita or water. Probiotic or water was administered again on day 9 and 10. When the control groups began presenting symptoms, *E. mundtii* strain ST4SA was administered via intragastric gavage to one of the groups. This group was then monitored for alleviation of symptoms.

Animals were monitored twice daily for symptoms of listeriosis. Animals were sacrificed on day 11 (except the control group now receiving *E. mundtii* strain ST4SA). Blood was sampled from the right ventricle. Total blood counts were determined by a pathologist laboratory, a sample of blood was inoculated onto BHI solid media and *Listeria* selective agar base and the cfu/ml was determined. Plasma was collected and endotoxin levels as well as cytokine (IL-6 and IFN-α) levels were determined. The liver, spleen and sections of the gastrointestinal tract were excised and fixed in formaldehyde prior to paraffin embedding.

Figure 31:
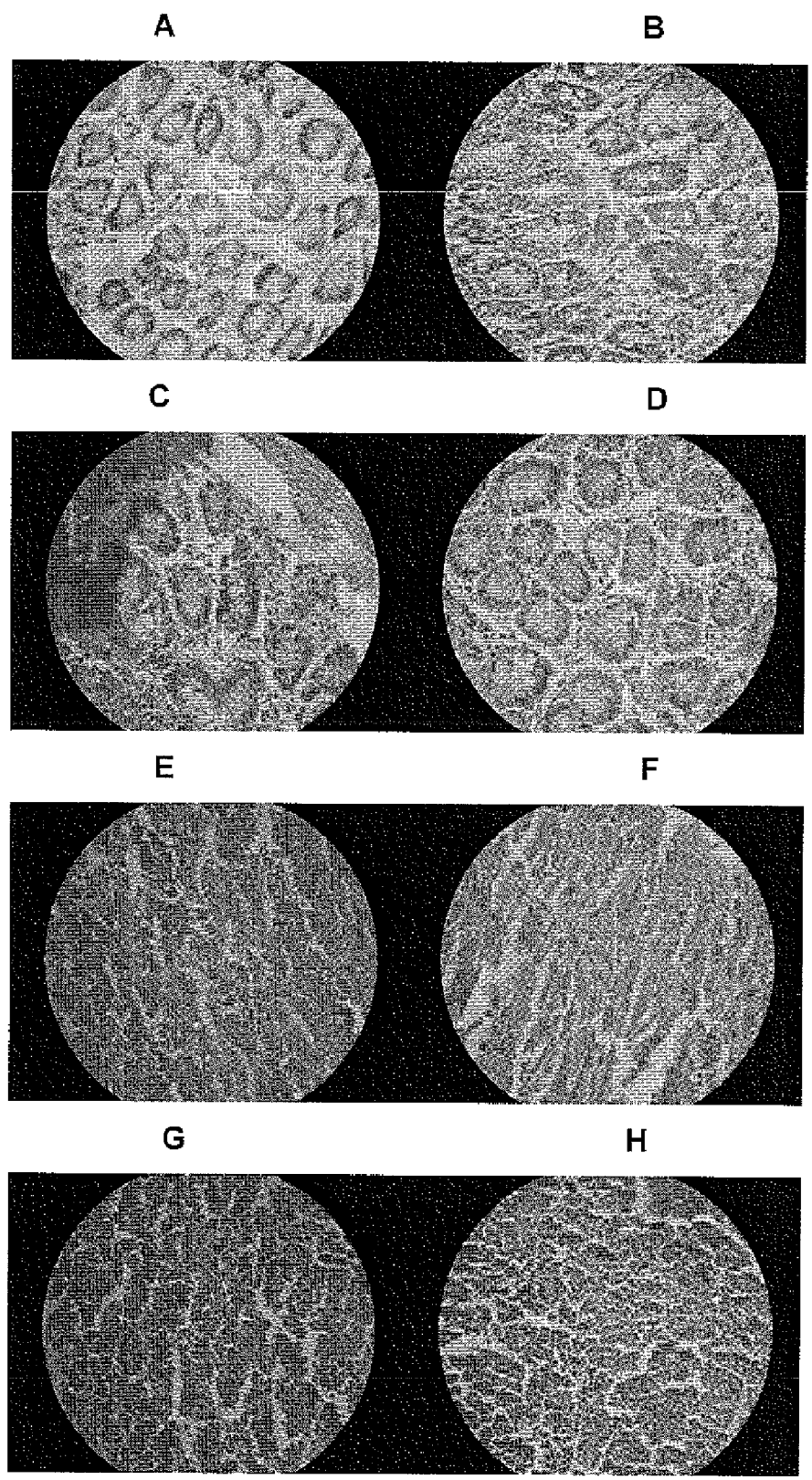
FIG. 31 shows hemolysin and eosin stained sections of (A) Control Colon (B) Strain ST4SA fed colon (C) Control Ileum (D) Strain ST4SA fed Ileum (E) Control Liver (F) Strain ST4SA fed liver (G) Control Spleen (H) Strain ST4SA Spleen at 60× magnification.

Sections were stained with hemolysin and eosin for histological analysis. The hemolysin and eosin analysis indicated that oral administration of strain ST4SA does not result in any structural damage to the liver, spleen or GIT (see FIG. 31). No differences were observed between animals that had been administered strain ST4SA and those receiving only unsupplemented water.

As described herein, the *Enterococcus mundtii* strain, ST4SA, isolated from soy bean extract, has been found by the Applicant to produce a useful antibacterial peptide, peptide ST4SA, which is active against a number of pathogenic organisms such as those isolated from human middle-ear infections and the human intestine. Advantageously, peptide ST4SA is not cytotoxic. The *Enterococcus mundtii* ST4SA strain has been distinguished by the Applicant from other strains of *E. mundtii* by sugar fermentation reactions, a number of biochemical tests, the presence of two plasmids (pST4SA1 and pST4SA2), and a unique gene (AdhST4SA), encoding adhesion to intestinal epithelial cells and mucus. Peptide ST4SA has been purified and sequenced, and contains two large hydrophobic regions. The Applicant has isolated and sequenced the nucleic acid sequence encoding peptide ST4SA, as well as the nucleic acid sequence encoding the transport of peptide ST4SA across the cell membrane, which serves to render immunity to the producer cell against its own peptide. All latter genes are located on the genome, since curing of the strain of its plasmids did not lead to loss in antimicrobial activity. Furthermore, transformation of the plasmids to a strain of *Enterococcus faecalis* did not convert the recipient into a peptide ST4SA producer, which is further evidence that the genes are not located on the plasmids. Loss in antimicrobial activity after treating the peptide with proteolytic enzymes confirmed that the activity is due to the peptide structure and not lipids or carbohydrates linked to the molecule. Surprisingly, the peptide remained active after 30 min of incubation in buffers between pH 2.0 and 12.0, and after 90 min at 100° C. Even more surprisingly, treatment with EDTA, SDS, Tween 20, Tween 80 and Triton X-100 did not lead to loss in antimicrobial activity. Strain ST4SA survives low pH conditions (pH 2.5), grows in medium adjusted from pH 4.0 to 9.6 in the presence of 6.5% NaCl, and is resistant to 1.0% (w/v) bile salts and pancreatic juice. Growth of strain ST4SA occurs at 10° C. (although slowly) and at 45° C., with optimal growth at 37° C. Only L(+)-lactic acid is produced from glucose. These strain characteristics, the rapid and stable production of peptide ST4SA, even when the strain is exposed to environmental stress, the fact that the peptide is non-cytotoxic, and that it is produced by an organism with GRAS (generally regarded as safe) status, renders the strain a useful probiotic.

The peptide also has use as an antimicrobial agent in a liquid formulation, as a topical treatment for, for example, middle-ear infections. This liquid formulation may be applied to the ear using an ear drop applicator. The liquid formulation is also included in a liquid form of the probiotic of *Enterococcus mundtii* for use as a liquid supplement to meals. The peptide further finds use as an antimicrobial agent in either a liquid or aspirated form in a nasal spray for treatment in, for example, sinus infections or sinusitis. The peptide is also used as an antimicrobial agent encapsulated in a polymer. This polymer is then used in a formulation for topical treatment of infections such as, for example, skin infections, or it may be used for incorporation in implants such as, for example, ear grommets, or for incorporation in wound dressings. The encapsulation of the antimicrobial peptide in the polymer leads to a slow release of the antimicrobial peptide and an extended period of treatment of a microbial infection. The peptide also finds use as an antimicrobial agent by being incorporated into ointment, lotion, or cream formulations and used to treat infections. The peptide may also further be used as an antimicrobial agent by being incorporated into liquid formulations such as, for example, contact lens rinsing fluid, or it may be incorporated into the contact lenses themselves. The peptide may also be used as an antimicrobial agent by being incorporated into packaging material such as plastic, for use in the manufacture of aseptic packaging. In an even further form of the invention the peptide may be used as part of a broad-spectrum probiotic of *Enterococcus mundtii* in a tablet form or in a capsule form or it may be in an edible form such as, for example, a sweet or chewing gum.

Sequence Listing

```
Enterococcus mundtii strain ST4SA (ATCC PTA-7278)
ribosome subunit 16S gene primers
SEQ. ID. NO. 1: Forward primer
AACGAGCGCAACCC SEQ. ID. NO. 2: Reverse primer
GACGGGCGGTGTGTAC Enterococcus mundtii strain ST4SA (ATCC PTA-7278)
structural gene primers
SEQ. ID. NO. 3: Forward primer
SG-a: TGAGAGAAGGTTTAAGTTTTGAAGAA SEQ. ID. NO. 4: Reverse primer
SG-b: TCCDACTGAAATCCATGAATGA Enterococcus mundtii strain ST4SA (ATCC PTA-7278)
ABC transporter gene primers
SEQ. ID. NO. 5: Forward primer
ABC1-a: TGATGGATTTCAGTGGAAGT SEQ. ID. NO. 6: Reverse primer
ABC1-b: ATCTCTTCTCCGTTTAATCG
```

SEQ. ID. NO. 7: Forward primer
ABC2-a: GTCATTGTTGTGGGGATTAT

SEQ. ID. NO. 8: Reverse primer
ABC2-b: TCTAGATACGTATCAAGTCC

*Enterococcus mundtii* strain ST4SA (ATCC PTA-7278) immunity gene primers
SEQ. ID. NO. 9: Forward primer
Immun-a: TTCCTGATGAACAAGAACTC SEQ. ID. NO. 10: Reverse primer
Immun-b: GTCCCCACAACCAATAACTA SEQ. ID. NO. 11
Polynucleotide encoding *Enterococcus mundtii* (ATCC PTA-7278) antimicrobial peptide ST4SA
ATGTCACAAGTAGTAGGTGGAAAATACTACGGTAATGGAGTCTCATGTAA
TAAAAAAGGTGCAGTGTTGATTGGGGAAAAGCTATTGGCATTATTGGAAA
TAATTCTGCTGCGAATTTAGCTACTGGTGGAGCAGCTGGTTGGAAAAGTT
AA SEQ. ID. NO. 12
Polypeptide encoded by *Enterococcus mundtii* (ATCC PTA-7278) antimicrobial peptide ST4SA
MSQVVGGKYYGNGVSCNKKGCSVDWGKAIGIIGNNSAANLATGGAAGWKS SEQ. ID. NO. 13
Polynucleotide encoding *Enterococcus mundtii* ST4SA (ATCC PTA-7278) ABC transporter gene
ATGCAGATGATTTTAAATAATTTTCATTCATGGATTTCAGTGGAAGTTTT
AAGAGACTTAACTGAAACCGATTCTGAAGGTACCTGTGCATTAGGTATAG
TTAACGGATTTGCTAAATTAGGAATAAATTGTGAAGCCTATAAAGCTAAT
AGTGATGTATGGAAAGAAAATGAGTTCAATTATCCCGTAATTGCTAATAT
AGTAACGAATAATCAATTTCTTCATTATTGTATTGTATATGGTGTGAAAA
AAGAGAAATTGTTAATAGCTGACCCTGCGATTGGAAAATACAAAGAATCA
ATAGAAAAGTTCAACAACAAATGGACTGGTGTTATTTTAGTTGCTGAAAA
GACTCCTGATTTCCAACCCATAAATAATACAAAAAAAAGTTTTTTTCTT
CAATAAGTTTATTAAAAGATCAATATAAAAAATTTTATTGGTGATATTA
TCTTCATTAATAATAACAATTATAGGAATACTATCAAGTTACTATTTTAG
AATTTTAATAGATTGGTTACTTCCTGAAAAAGACTTTTTAAATCTATTTA
TGATATCAATTAGCTATATCATAGGCATTTTTTATAACAAGTATATTTGAA
ATTACCAGAAGATATAATTTAGAAAAGCTAGGACAAGATGTAGGTAGAAG
CATTTTATTTAAATATTTAGAACATATTTTCATTTTACCAGCTTCCTTTT
TTTCTAAAAGAAAAACTGGAGATATTGTCTCTAGATTTTCTGATGCTAAT
AAAATTATAGAAGCTTTAGCTAGCTTTACTATATCTATTTTTTTAGATTT
AAGTTCAGTCATTGTTGTGGGGATTATATTGATCAATATTAATAAACAAT
TATTTTTAATAACGTTAAGTTCTATTCCATTTTATATACTAATTATATTA
GGATCAAATAAAAAAATGAGTCGATTAAACGGAGAAGAGATGCAAACAAA
TTCAATAGTTGATTCTAATTTTATTGAAGGATTAAACGGAATATATACTA
TAAAAGCACTTTGTAGTGAGAATAAGATTGTAAATCAAATATATAGAAGT
TTAAATAAATTTTTTGATGTATCACTAAAGAGAAATATGTATGATTCTAT
AATTCAAAATTTAAAAATTTTGGTTTCTCTTTTAACCTCGGCTTTTGTAT
TATGGCTTGGTTCGTATTATGTTATCAATGGAGAAATTACAATAGGAGAA
CTAATAACTTTCAATTCATTATCTATATTTTTTCTACACCTCTACAAAA
TATAATAAATCTACAAGAAAAATTCCAAAAAGCACAAGTTGCAAATAATC
GGCTTAACGATGTATTTCTATAAATAATGAAAATAAAGACAAGTTTATT
CATTTGGCTAAATTAACTGAAAAAGCAACGATTACATTTGAAAATGTATA
TTTTAGTTATTCTACTAAATATCCTAATGTGTTAGATAATATGAGTTTTT
CTCTACCTGTGAGTAAAAATAGGAATAAAAGGTGATAGTGGTGCTGGGG
AAATCAACTTTAGCACAACTTCTAGCTGGATTTTACTCTCCAGATAATGG
AAGAATTTGTATAAATGAGCAAATATTGAAAATATTAATAGAAAAGATT
TACGTAAGTTGATTACCTATGTGCCTCAAGAATCTTTTATTATGAGTGGA
ACTATTAAAGACAATTTATTTTTAGGTTTAGAAAGTATTCCTGATGAACA
AGAACTCGAAAAAGTACTGAAAGATACTTGTTTATGGAGTTATATTACTG
CGCCTCCTCTAGGACTTGATACGTATCTAGAAGAAAATGGTGCGAATTTA
TCAGGTGGTCAAAAGCAAAGAATTGCTTTAGCAAGAGTTTTATTATTAGG
AAGTAAAATTTTATTATTAGATGAAGCTACGAGTGCTCTAGATTCTAAAA
CTGAAATGCTGATTTTAGAAAAATTTATTAAAGTACCCTAATAAGTCAATC
ATTATGATATCTCATAATGATAAATTAATAGACAAGTGTGACTTAATCAT
TGATTTAGACGAAAGGGATTCATAA SEQ. ID. NO. 14
Polypeptide encoded by *Enterococcus mundtii* ST4SA (ATCC PTA-7278) ABC transporter gene
MQMILNNFHSWISVEVLRDLTETDSEGTCALGIVNGFAKLGINCEAYKAN
SDVWKENEFNYPVIANIVTNNQFLHYCIVYGVKKEKLLIADPAIGKYKES
IEKFNNKWTGVILVAEKTPDFQPINNTKKSFFSSISLLKDQYKKILLVIL
SSLIITIIGILSSYYFRILIDWLLPEKDFLNLFMISISYIIGIFITSFE
ITRRYNLEKLGQDVGRSILFKYLEHIFILPASFFSKRKTGDIVSRFSDAN
KIIEALASFTISIFLDLSSVIVVGIILININKQLFLITLSSIPFYILIIL
GSNKKMSRLNGEEMQTNSIVDSNFIEGLNGIYTIKALCSENKIVNQIYRS
LNKFFDVSLKRNMYDSIIQNLKILVSLLTSAFVLWLGSYYVINGEITIGE
LITFNSLSIFFSTPLQNIINLQEKFQKAQVANNRLNDVFSINNENKDKFI
HLAKLTEKATITFENVYFSYSTKYPNVLDNMSFSLPVSKNIGIKGDSGAG
KSTLAQLLAGFYSPDNGRICINEQNIENINRKDLRKLITYVPQESFIMSG
TIKDNLFLGLESIPDEQELEKVLKDTCLWSYITAPPLGLDTYLEENGANL
SGGQKQRIALARVLLLGSKILLLDEATSALDSKTEMLILEKLLKYPNKSI
IMISHNDKLIDKCDLIIDLDERDS SEQ. ID. NO. 15
Polynucleotide encoding *Enterococcus mundtii* ST4SA (ATCC PTA-7278) immunity gene
ATGAGTAATTTAAAGTGGTTTTCTGGTGGAGACGATCGACGTAAAAAAGC
AGAAGTGATTATTACTGAATTATTAGATGATTTAGAGATAGATCTTGGAA
ATGAATCTCTTCGAAAAGTATTAGGCTCCTATCTTGAAAAGTGAAAAATG
AAGGAACTTCAGTTCCATTAGTTTTAAGTCGTATGAATATAGAGATATCT
AATGCAATAAAAAAAGACGGTGTATCGTTAAATGAAAATCAATCTAAAAA
ATTAAAAGAACTCATATCTATATCTAATATTAGATATGGATATTAG SEQ. ID. NO. 16
Polypeptide encoded by *Enterococcus mundtii* ST4SA immunity gene
MSNLKWFSGGDDRRKKAEVIITELLDDLEIDLGNESLRKVLGSYLEKLKN
EGTSVPLVLSRMNIEISNAIKKDGVSLNENQSKKLKELISISNIRYGY SEQ. ID. NO. 17
Polypeptide encoded by *Enterococcus mundtii* (ATCC PTA-7278) antimicrobial peptide ST4SA Fragment 1
KYYGNGVSCNKKGCSVDWGKAIGIIGNNS SEQ. ID. NO. 18
Polypeptide encoded by *Enterococcus mundtii* (ATCC PTA-7278) antimicrobial peptide ST4SA Fragment 2
KAIGIIGNNSAANLATGGAAGWKS SEQ. ID. NO. 19
Polynucleotide encoded by *Enterococcus mundtii* ST4SA (ATCC PTA-7278) Fragment 1
AAATACTACGGTAATGGAGTCTCATGTAATAAAAAAGGGTGCAGTGTTG
ATTGGGGAAAAGCTATTGGCATTATTGGAAATAATTCT SEQ. ID. NO. 20
Polypeptide encoded by *Enterococcus mundtii* ST4SA (ATCC PTA-7278) Fragment 2
AAAGCTATTGGCATTATTGGAAATAATTCTGCTGCGAATTTAGCTACTG
GTGGAGCAGCTGGTTGGAAAAGT

---

The invention claimed is:

1. A method of treating a bacterial infection caused by any one or more of *Acinetobacter baumanii*; *Bacillus cereus*; *Clostridium tyrobutyricum*; *Enterobacter cloacae*; *Escherichia coli*; *Klebsiella pneumoniae*; *Listeria innocua*; *Pseudomonas auringinosa*; *Staphylococcus aureus*; *Staphylococcus carnosus*; *Streptococcus caprinus*; *Streptococcus (Enterococcus) faecalis*; or *Streptococcus pneumoniae* in an animal or human, the method including the step of exposing an infected area of the animal or human to a substance or composition including a therapeutically effective amount of a substantially pure culture of *Enterococcus mundtii* strain ST4SA deposited with the ATCC under the assigned number PTA-7278, said culture capable of producing peptide ST4SA in a recoverable quantity upon fermentation in a nutrient medium containing assimilable sources of carbon, nitrogen, and inorganic substances.

2. The method as claimed in claim 1, wherein the cultured strain is included in a concentration of approximately $10^6$ to $10^9$ cfu (colony forming units) per ml.

3. The method as claimed in claim 2, wherein the cultured strain is included in a concentration of approximately $10^8$ cfu (colony forming units) per ml.

* * * * *